United States Patent

Namekawa et al.

[11] Patent Number: 5,368,771
[45] Date of Patent: Nov. 29, 1994

[54] OPTICALLY ACTIVE TETRAHYDROPYRANE DERIVATIVES, LIQUID CRYSTAL COMPOSITION AND LIQUID CRYSTAL DEVICE CONTAINING THE SAME

[75] Inventors: Masaaki Namekawa; Shinichi Nayuki; Keizou Itoh; Mitsunori Takeda; Yoshinobu Murayama, all of Ibaraki, Japan

[73] Assignee: Kashima Oil Company, Tokyo, Japan

[21] Appl. No.: 107,717

[22] PCT Filed: Dec. 15, 1992

[86] PCT No.: PCT/JP92/01628

§ 371 Date: Aug. 24, 1993

§ 102(e) Date: Aug. 24, 1993

[87] PCT Pub. No.: WO93/13088

PCT Pub. Date: Jul. 8, 1993

[30] Foreign Application Priority Data

Dec. 26, 1991 [JP] Japan .................. 3-344202
May 11, 1992 [JP] Japan .................. 4-117488
Jul. 28, 1992 [JP] Japan .................. 4-201189

[51] Int. Cl.$^5$ .................. C09K 19/52; C07D 309/10; G02F 1/13
[52] U.S. Cl. .................. 252/299.1; 549/356; 359/103
[58] Field of Search .................. 252/299.61, 299.01; 549/356; 359/103

[56] References Cited

FOREIGN PATENT DOCUMENTS 62-226974 10/1987 Japan .

Primary Examiner—Shean Wu
Attorney, Agent, or Firm—Oblon, Spivak, McClelland, Maier & Neustadt

[57] ABSTRACT

There are disclosed a novel optically active tetrahydropyrane derivatives (for example, (2R,5R,6R)-tetrahydro-6-trifluoromethyl-2-hexyloxy-5-(4"-hexyloxybiphenyl)-4'-carbonyloxy)pyrane; (2S,5R,6R)-tetrahydro-6-trifluoromethyl-2-hexyloxy-5-(4"-hexyloxybiphenyl)-4'-carbonyloxy)pyrane, etc. may be mentioned.) represented by the formula (I):

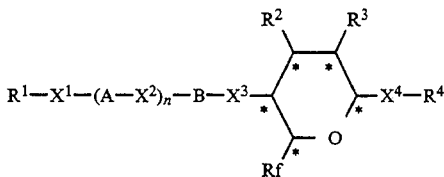

or (I'):

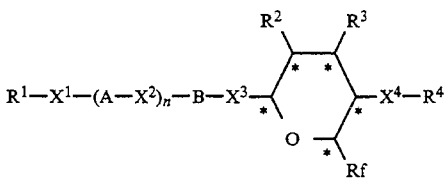

wherein symbols in the formula are as described in the specification, which is available as a liquid crystal material used for a display device or an electro-optic device, a liquid crystal composition and a liquid crystal device containing the same.

The optically active tetrahydropyrane derivative of the present invention can improve high speed response particularly when it is made a composition, and is available as a compositional component for a ferroelectric liquid crystal which induces a large spontaneous polarization.

7 Claims, No Drawings

OPTICALLY ACTIVE TETRAHYDROPYRANE DERIVATIVES, LIQUID CRYSTAL COMPOSITION AND LIQUID CRYSTAL DEVICE CONTAINING THE SAME

TECHNICAL FIELD

This invention relates to an optically active tetrahydropyrane derivative, a liquid crystal composition and a liquid crystal device containing the same, more specifically, a novel optically active tetrahydropyrane derivative available as a liquid crystal material used for a display device or an electro-optic element, a liquid crystal composition and a liquid crystal device containing the same.

BACKGROUND ART

In recent years, applicable fields of liquid crystals such as various kinds of display devices, electronic optical devices, liquid crystal sensors, etc. have markedly been enlarged, and accompanying these situation, liquid crystal compounds having various structures have been proposed. In liquid crystal materials particularly used for display devices, nematic liquid crystals are at present in main stream, and a TN type or a STN type simple matrix system using the same and a TFT type active matrix system in which a thin film transistor is provided to respective picture elements have been used. However, a driving force of the nematic liquid crystal is based on weak interaction between anisotropy of dielectric constant of a liquid crystal material and an electric field so that it has a drawback that a response speed is essentially late (msec order). Thus, it is disadvantageous as a material for a display device with a large sized screen in which high speed response is required.

To the contrary, a ferroelectric liquid crystal which has firstly been synthesized by R. B. Meyer et al. in 1975 has a spontaneous polarization and this acts directly on an electric field so that the liquid crystal has a large driving force. Since N. A. Clark et al. has reported in 1980 about a high speed response with micro-second order and memory effect of a surface stabilized ferroelectric liquid crystal device (SSFLCD), it has been attracted to attention and many ferroelectric liquid crystal compounds have been synthesized.

When the ferroelectric liquid crystal compound is used as a material for a display device, the following conditions are generally required. (1) It has a chiral smectic C phase (SmC* phase) in a wide temperature range including room temperature. (2) Electro-optic response speed is high. (3) Alignment quality is good. Until now, it is difficult to satisfy all the conditions with a single compound.

Accordingly, there has been employed a method in which several kinds of compounds having SmC* phases are mixed or an optically active compound is added to an achiral host mixture having a smectic C phase (SmC phase) which has a low viscosity whereby a ferroelectric liquid crystal composition having desired characteristics and exhibiting SmC* phase is obtained.

In the latter case, a chiral dopant to be added may, itself, have BmC* phase or may not have the phase, and it is required to have good compatibility with the achiral host mixture, induce a high magnitude of spontaneous polarization and not increase the viscosity.

It is well known that a response time of a ferroelectric liquid crystal is expressed by the following equation; $\tau = \eta/(Ps.E)$. Here, $\eta$ represents a rotational viscosity, Ps represents a spontaneous polarization, and E represents an electric field intensity. From this equation, in order to obtain a high speed response, a liquid crystal material having a low viscosity and a large spontaneous polarization has been aimed to be developed.

The spontaneous polarization has been considered to be caused by the result that free rotation of a dipole moment perpendicular to a molecular long axis is restricted around it by the effect of an asymmetric carbon. Accordingly, in order to increase spontaneous polarization, many attempts have been made by the methods that (1) a dipole portion is allowed to come near a skeleton portion which is a so-called core, (2) a dipole portion and an asymmetric carbon are allowed to place near position, and (3) a sterically large substituent is attached to an asymmetric carbon whereby free rotation around a molecular long axis is restricted, etc.

Further, it has recently been reported that a compound having a structure that a dipole portion and an asymmetric carbon are directly bonded to a 5-membered lactone effectively inhibits free rotation whereby having a large spontaneous polarization (Japanese Journal of Applied Physics, vol. 29, No. 6, ppL 981 to L 983).

When a ferroelectric liquid crystal mixture is aligned by a rubbing method which has conventionally been carried out in a nematic liquid crystal, its alignment quality is different depending on a phase sequences of a liquid crystal material, and it is preferred to have the phase sequences of an isotropic phase (Iso phase)→ a cholesteric phase (N* phase)→ a smectic A phase (SmA phase)→ a chiral smectic C phase (SmC* phase).

Here, in the N* phase, it is necessary to have a sufficiently long helical pitch.

Thus, in order to unwind the helix in the N* phase or the SmC* phase, there has been employed a method of elongating the helical pitch by mixing a ferroelectric liquid crystal having a reverse helical sense (Japanese Patent Applications Laid-Open No. 117488/1992 and No. 220289/1991).

DISCLOSURE OF INVENTION

Under such circumstances, the present inventors have intensively studied.

As a result, the present inventors have found that a novel compound in which an asymmetric carbon atom on a tetrahydropyrane ring has a fluoroalkyl group having itself a large electrophilic property has a liquid crystal phase by itself, or does not have the phase but induces a large spontaneous polarization, exhibits a high speed response and easily gives good orientation when it is mixed in a composition whereby it can be an excellent chiral dopant.

The present invention has been accomplished based on such findings.

That is, the present invention is to provide an optically active tetrahydropyrane derivative represented by the formula (I):

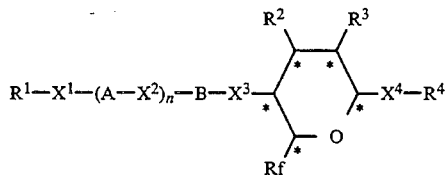

or (I'):

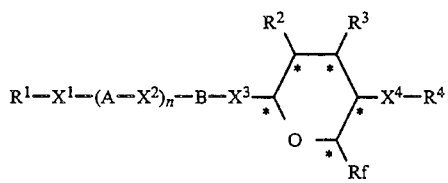

wherein Rf represents a fluoroalkyl group having 1 or 2 carbon atoms, $R^1$ represents a straight or branched alkyl group having 3 to 20 carbon atoms, $R^2$, $R^3$ and $R^4$ each independently represents a hydrogen, a straight or branched alkyl group having 1 to 15 carbon atoms, an alkenyl group having 2 to 15 carbon atoms or an aralkyl group having 7 to 10 carbon atoms, $X^1$ represents —COO—, —OCO—, —O— or a single bond, $X^2$ represents —COO—, —OCO—, —CH$_2$O—, —OCH$_2$— or a single bond, $X^3$ represents —COO—, CH$_2$O— or —O—, $X^4$ represents —O— or —OCO—, * represents an asymmetric carbon, A and B each independently represents

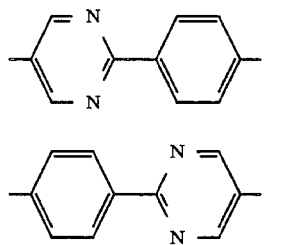

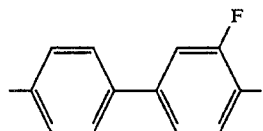

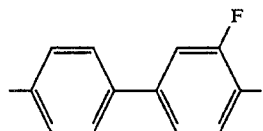

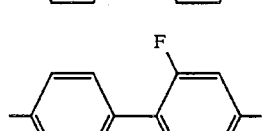

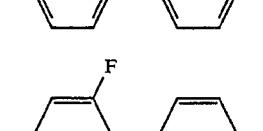

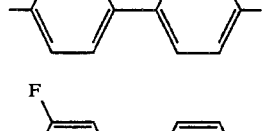

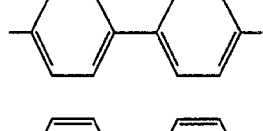

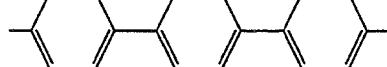

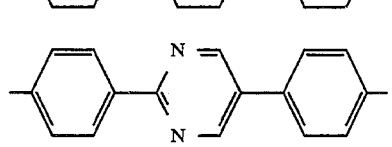

and n represents 0 or 1.

BEST MODE FOR CARRYING OUT THE INVENTION

In the formula (I) or (I'), the aforesaid Rf represents a fluoroalkyl group having 1 or 2 carbon atom, more specifically, it may be a trifluoromethyl group, a difluoromethyl group, a chlorodifluoromethyl group, a pentafluoroethyl group, etc., preferably a trifluoromethyl group.

Also, $R^1$ represents a straight or branched alkyl group having 3 to 20 carbon atoms, for example, an n-propyl group, an isopropyl group, an n-butyl group, an isobutyl group, a sec-butyl group, a tert-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, etc. Among these, a group which is a branched alkyl group and has an asymmetric carbon is an optically active group.

Further, $R^2$, $R^3$ and $R^4$ each independently represents a hydrogen or a straight or branched alkyl group having 1 to 15 carbon atoms such as a methyl group, an ethyl group, an n-propyl group, an isopropyl group, an n-butyl group, a sec-butyl group, a tert-butyl group, an n-pentyl group, an isopentyl group, a 1-methylbutyl group, an n-hexyl group, an n-heptyl group, a 1-methylheptyl group, an n-octyl group, a 1-ethylheptyl group, a 1-methyloctyl group, an n-nonyl group, a 1-ethyloctyl group, a 1-methylnonyl group, an n-decyl group, an n-undecyl group, an n-dodecyl group, an n-tridecyl group, an n-tetradecyl group, an n-pentadecyl group, etc.

Also, as the alkenyl group having 2 to 15 carbon atoms, there may be mentioned a vinyl group, an allyl group, a 1-propenyl group, an isopropenyl group, a 1-butenyl group, a 2-butenyl group, a 2-methylallyl group, a 1-pentenyl group, a 1-hexyenyl group, a 1-heptenyl group, a 1-octenyl group, a 2-octenyl group, a 1-nonenyl group, a 2-nonenyl group, a 1-decenyl group, a 2-decenyl group, a 1-undecenyl group, a 2-undecenyl group, a 1-dodecenyl group, a 2-dodecenyl group, a 1-tridecenyl group, a 2-tridecenyl group, a 1-tetradecenyl group, a 2-tetradecenyl group, a 1-pentadecenyl group, a 2-pentadecenyl group, etc. As the aralkyl group with 7 to 10 carbon atoms, there may be mentioned a benzyl group, a phenethyl group, a phenylpropyl group, a phenylbutyl group, etc.

The compound of the formula (I) according to the present invention can be produced by various methods, but it may be produced, for example, by the following procedures.

(1) The case where $X^2$=single bond and $X^3$=—COO—

The compound of the above formula (I) can be obtained by reacting a compound represented by the following formula (II):

$$R^1-X^1-A-B-COHal \qquad (II)$$

wherein $R^1$, $X^1$, A and B are the same as mentioned above. Hal represents a halogen such as chlorine, bromine, iodine, etc., and a compound represented by the following formula (III):

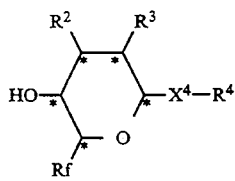

wherein Rf, $R^2$, $R^3$, $R^4$, $X^4$ and * are the same as mentioned above.

The reaction can be carried out in the presence of an organic base such as pyridine, triethylamine, etc., in a solvent such as toluene, benzene, methylene chloride, etc. in a temperature range of —20° to 80° C.

(2) The case where $X^2$=ingle bond and $X^3$=—CH$_2$O—

The compound of the above formula (I) can be obtained by reacting a compound represented by the following formula (IV):

$$R^1-X^1-A-B-CH_2Z \qquad (IV)$$

wherein $R^1$, $X^1$, A and B are the same as mentioned above, and Z represents chlorine, bromine, iodine or a tosyl group, and a compound represented by the above formula (III). The reaction can be carried out by allowing a base represented by an alkali metal hydride, sodium hydroxide or potassium hydroxide to act on the compound of the formula (III), and then adding the compound of the formula (IV).

(3) The case where $X^2$=—COO— and $X^3$=—COO—

By reacting a compound represented by the following formula (V):

$$BzO-B-COHal \qquad (V)$$

wherein B and Hal are the same as mentioned above and Bz represents a benzyl group, and the compound represented by the above formula (III), a compound represented by the formula (VI):

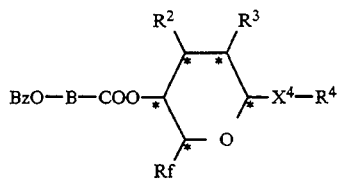

wherein Rf, Bz, B, $X^4$, $R^2$, $R^3$, $R^4$ and * are the same as mentioned above,
can be obtained. The reaction can be carried out in the presence of an organic base such as pyridine, triethylamine, etc., in a solvent such as toluene, benzene, methylene chloride, etc. in a temperature range of —20° to 80° C.

Next, when the benzyl group in the resulting compound of the formula (VI) is eliminated by a conventional method, a compound represented by the following formula (VII):

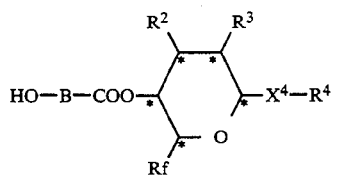

wherein Rf, B, $X^4$, $R^2$, $R^3$, $R^4$ and * are the same as mentioned above,
can be formed. This debenzylation reaction can be carried out, for example, by subjecting to hydrogenolysis in the presence of a Pd/C catalyst by using an alcoholic solvent such as methanol, ethanol, propanol, ere. or acetic acid under normal pressure.

Further, when the obtained compound represented by the formula (VII) is reacted with a compound represented by the following formula (VIII):

$$R^1-X^1-A-COHal \qquad (VIII)$$

wherein $R^1$, $X^1$, A and Hal are the same as mentioned above, the compound of the above formula (I) can be obtained. The reaction can be carried out in the presence of an organic base such as pyridine, triethylamine, etc., in a solvent such as toluene, benzene, methylene chloride, etc. in a temperature range of —20° to 80° C.

(4) The case where $X^2$=—COO— and $X^3$=—CH$_2$O—

By reacting a compound represented by the formula (IX):

$$ThpO-B-CH_2Z \qquad (IX)$$

wherein Thp represents (tetrahydropyranyl group), B and Z are the same as mentioned above,
and a compound represented by the above formula (III), a compound represented by the following formula (X):

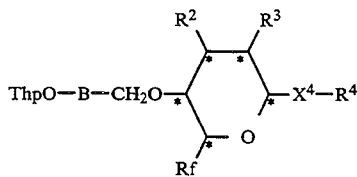

wherein Rf, Thp, B, $X^4$, $R^2$, $R^3$, $R^4$ and * are the same as mentioned above,
can be obtained. The reaction can be carried out by allowing a base represented by an alkali metal hydride, sodium hydroxide or potassium hydroxide to act on the compound represented by the formula (III), and then adding the compound of the formula (IX).

Next, when the Thp in the resulting compound of the formula (X) is eliminated by a conventional method, a compound represented by the following formula (XI):

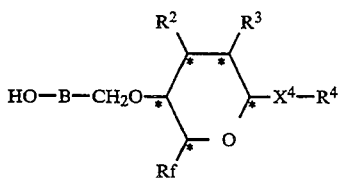

wherein Rf, B, $X^4$, $R^2$, $R^3$, $R^4$ and * are the same as mentioned above,
can be obtained. The elimination of the tetrahydropyranyl group can be carried out in the presence of an acid catalyst such as hydrochloric acid, sulfuric acid and paratoluene sulfonic acid, etc. in a solvent such as toluene, benzene, methylene chloride, etc. in a temperature range of $-20°$ to $80°$ C.

(5) The case where $X^2=$—COO— and $X^3=$—O—

By reacting a compound represented by the following formula (XII):

ThpO—B—Hal  (XII)

wherein Thp, B and Hal are the same as mentioned above, and the compound represented by the above formula (III), a compound represented by the following formula (XIII):

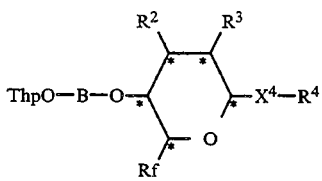

wherein Rf, Thp, B, $X^4$, $R^2$, $R^3$, $R^4$ and * are the same as mentioned above,
can be obtained. The reaction can be carried out by allowing a base represented by an alkali metal hydride, sodium hydroxide to act or potassium hydroxide on the compound represented by the formula (III), and then under refluxing conditions such as dimethylformamide, dimethylsulfoxide, etc., the compound represented by the formula (XII) is reacted by using cuprous iodide as a catalyst.

Next, when the tetrahydropyranyl group in the resulting compound represented by the formula (XIII) is eliminated by a conventional method, a compound represented by the following formula (XIV):

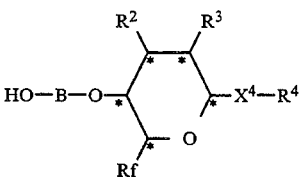

wherein Rf, B, $X^4$, $R^2$, $R^3$, $R^4$ and * are the same as mentioned above,
can be obtained.

The elimination of the tetrahydropyranyl group can be carried out in the presence of an acid catalyst such as hydrochloric acid, sulfuric acid and paratoluene sulfonic acid, etc. in a solvent such as ether, tetrahydrofuran, chloroform, etc.

By reacting the compound of the formula (XIV) obtained here with the compound represented by the above formula (VIII), the compound of the above formula (I) can be obtained. The reaction can be carried out in the presence of an organic base such as pyridine, triethylamine, etc., in a solvent such as toluene, benzene, methylene chloride, etc. in a temperature range of $-20°$ to $80°$ C.

(6) The case where $X^2=$—CH$_2$O— and $X^3=$—COO—

By reacting the compound represented by the above formula (VII) and a compound represented by the following formula (XV):

$R^1$—$X^1$—A—CH$_2$Z  (XV)

wherein $R^1$, $X^1$, A and Z are the same as mentioned above,
the compound of the above formula (I) can be obtained. The reaction can be carried out by allowing a base represented by an alkali metal hydride, sodium hydroxide or potassium hydroxide on to act the compound represented by the formula (VII), and then reacting the compound of the formula (XV).

(7) The case where $X^2=$—OCH$_2$— and $X^3=$—COO—

By reacting the compound represented by the following formula (XVI).

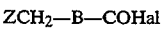

ZCH$_2$—B—COHal  (XVI)

wherein Z, B and Hal are the same as mentioned above, and the compound represented by the above formula (III), a compound represented by the following formula (XVII).

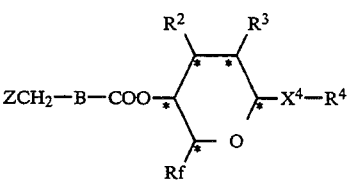

wherein RF, Z, B, $X^4$, $R^2$, $R^3$, $R^4$ and * are the same as mentioned above, can be obtained. The reaction can be carried out in the presence of an organic base such as pyridine, triethylamine, etc., in a solvent such as toluene, benzene, methylene chloride, etc. at a temperature range of −20° to 80° C.

Then, to the compound represented by the following formula (XVIII):

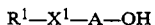    XVIII)

wherein $R^1$, $X^1$ and A are the same as mentioned above, is reacted the above compound (XVII), the compound of the above formula (I) can be obtained. The reaction can be carried out by allowing a base represented by an alkali metal hydride, sodium hydroxide to act or potassium hydroxide on the compound represented by the formula (XVIII), and then the compound represented by the formula (XVII) is added thereto.

Also, the compound of the formula (I') according to the present invention can be produced by various methods, and for example, it can be produced by the following procedures.

(1') The case where $X^3 = -COO-$, $X^4 = -OCO-0$ and $n = 0$

By reacting a compound represented by the following formula (XIX):

    (XIX)

wherein $R^1$, $X^1$, B and Hal are the same as mentioned above,
and a compound represented by the following formula (XX):

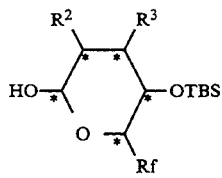

wherein Rf, $R^2$, $R^3$ and * are the same as mentioned above. TBS represents a t-butyldimethylsilyl group,
a compound represented by the formula (XXI):

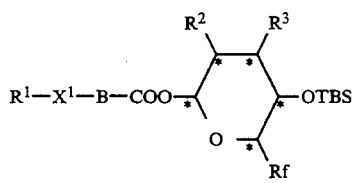

wherein RF, $R^1$, $R^2$, $R^3$, B, X1, TBS and * are the same mentioned above,
can be obtained. The reaction can be carried out in the presence of an organic base such as pyridine, triethylamine, etc., in a solvent such as toluene, benzene, methylene chloride, etc. at a temperance range of −20° to 80° C.

Next, by carrying out desilylation of the resulting compound represented by the Formula (XXI), a compound represented by the formula (XXIII):

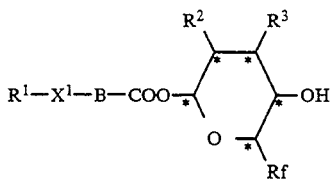

wherein Rf, $R^1$, $R^2$, $R^3$, B, $X^1$, and * are the same as mentioned above,
can be obtained. The desilylation reaction can be carried out by various methods, and it may be carried out, For example, in a tetrahydrofuran solvent, by using tetra-n-butylammonium Fluoride as a catalyst in a temperature range of 0° to 50° C.

Incidentally, the compound represented by the above Formula (XXIII) is a mixture of two kinds of diastereomers and it can be easily separated by silica gel column chromatography.

By reacting the compound represented by the formula (XXIII) with a compound represented by the formula (XXIV):

    (XXIV)

wherein $R^4$ and Hal are the same as mentioned above, the desired compound represented by the above formula (I') can be obtained. The reaction can be carried out in the presence of an organic base such as pyridine, triethylamine, etc., in a solvent such as toluene, benzene, methylene chloride, etc. in a temperature range of −20°0 to 80° C.

(2') The case where $X^3 = -COO-$, $X^4 = -O-0$ and $n = 0$

By reacting a compound represented by the following formula (XXV):

    (XXV)

wherein $R^5$ represents a straight or branched alkyl group having 1 to 15 carbon atoms, an alkenyl group having 2 to 15 carbon atoms or an aralkyl group having 7 to 10 carbon atoms, and the compound represented by the above formula (XX), a compound represented by the following formula (XXVI):

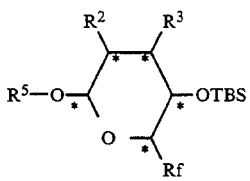

wherein Rf, $R^2$, $R^3$, $R^5$, TBS and * are the same as mentioned above,
can be obtained. The reaction can be carried out without any solvent or in a solvent such as tetrahydrofuran, etc. by using an acid catalyst such as paratoluene sulfonic acid, etc. in a temperature range of 0° to 50 ° C.

Next, by carrying out desilylation of the resulting compound represented by the formula (XXVI), a compound represented by the formula (XXVII):

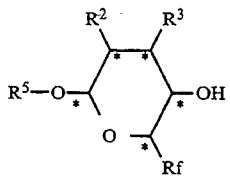

wherein Rf, $R^2$, $R^3$, $R^5$ and * are the same as mentioned above, can be obtained. The desilylation reaction can be carried out by various methods, and it may be carried out, for example, at a tetrahydrofuran solvent, by using tetra-n-butylammonium fluoride as a catalyst at a temperature range of 0° to 50° C.

Then, by reacting a compound represented by the formula (XXVIII):

$$R^4—Z \qquad \text{(XXVIII)}$$

wherein $R^4$ and Z are the same as mentioned above, and the compound represented by the above formula (XXVII), a compound represented by the following formula (XXIX):

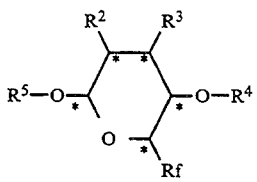

wherein Rf, $R^2$, $R^3$, $R^4$, $R^5$ and * are the same as mentioned above, can be obtained. The reaction can be carried out by allowing a base such as an alkali metal hydride, sodium hydroxide or potassium hydroxide to act on the compound represented by the formula (XXVII), and then adding the compound represented by the formula (XXVIII) thereto.

Further, by reacting the resulting compound represented by the formula (XXIX) in the presence of an acid catalyst, a compound represented by the formula (XXX):

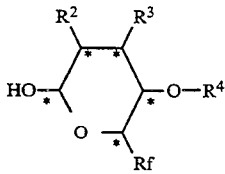

wherein Rf, $R^2$, $R^3$, $R^4$ and * are the same as mentioned above, can be obtained. The reaction can be carried out in the presence of water at a solvent such as tetrahydrofuran, ether, toluene, etc. by using an acid catalyst such as paratoluene sulfonic acid, hydrochloric acid, sulfuric acid, etc. at a temperature range of 0° to 100° C.

By reacting the compound represented by the formula (XXX) and the compound represented by the above formula (XIX), a desired compound represented by the above formula (I') can be obtained. The reaction can be carried out in the presence of an organic base such as pyridine, triethylamine, etc., in a solvent such as toluene, benzene, methylene chloride, etc. in a temperature range of −20°0 to 80° C.

(3') The case where $X^3$=—$CH_2O$—, $X^4$=—OCO— and n=0

By reacting a compound represented by the following formula (XXXI):

$$R^1—X^1—B—CH_2Z \qquad \text{(XXXI)}$$

wherein $R^1$, $X^1$, B and Z are the same as mentioned above, and the compound represented by the above formula (XXI), a compound represented by the following formula (XXXII):

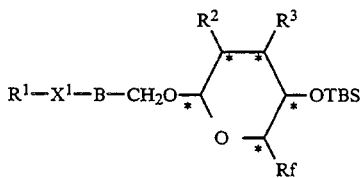

wherein Rf, $R^1$, $R^2$, $R^3$, $X^1$, B, TBS and * are the same as mentioned above, can be obtained. The reaction can be carried out by using an acid catalyst such as paratoluene sulfonic acid, hydrochloric acid, sulfuric acid, etc. in a solvent such as tetrahydrofuran, diethyl ether, methylene chloride, toluene, etc. at a temperature of 0° to 100° C.

Next, by carrying out desilylation of the resulting compound represented by the formula (XXXII) to obtain a compound represented by the formula (XXXIII):

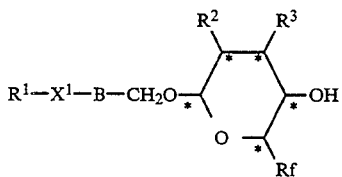

wherein Rf, $R^1$, $R^2$, $R^3$, $X^1$, B and * are the same as mentioned above, can be obtained. The desilylation reaction can be carried out by various methods, and it may be carried out, for example, in a tetrahydrofuran solvent, by using tetra-n-butylammonium fluoride as a catalyst at a temperature of 0° to 50° C.

Incidentally, the compound represented by the above formula (XXXIII) is a mixture of two kinds of diastereomers and it can be easily separated by silica gel column chromatography.

By reacting the compound represented by the formula (XXXIII) with the compound represented by the above formula (XXIV), the desired compound represented by the above formula (I') can be obtained. The reaction can be carried out in the presence of an organic base such as pyridine, triethylamine, etc., in a solvent such as toluene, benzene, methylene chloride, etc. at a temperature range of −20°0 to 80° C.

(4') The case where $X^3$=—$CH_2O$— $X^4$=—O— and n=0

By reacting the compound represented by the above formula (XXXIII) and the compound represented by the above formula (XXVIII), the desired compound of the above formula (I') can be obtained. The reaction can be carried out by allowing a base such as an alkali metal hydride, sodium hydroxide or potassium hydroxide, etc. to act on the compound represented by the formula (XXXIII), and then adding the compound of the formula (XXVIII) thereto.

(5') The case where $X^2 = -COO-$, $X^3 = -COO-$, $X^4 = -O-$ and $n = 1$

By reacting a compound represented by the following formula (XXXIV):

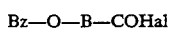

wherein Bz represents a benzyl group, and B and Hal are the same as mentioned above, and the compound represented by the above formula (XXX), a compound represented by the following formula (XXXV):

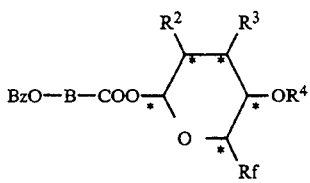

wherein Rf, $R^2$, $R^3$, $R^4$, B, Bz and * are the same as mentioned above, can be obtained. The reaction can be carried out at the presence of an organic base such as pyridine, triethylamine, etc., in a solvent such as toluene, benzene, methylene chloride, etc. at a temperature range of $-20°0$ to $80°$ C.

Next, by carrying out debenzylation reaction of the obtained compound represented by the formula (XXXV), a compound represented by the formula (XXXVI):

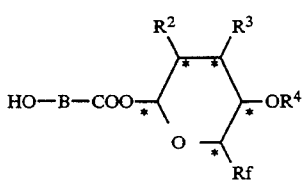

wherein Rf, $R^2$, $R^3$, $R^4$, B and * are the same as mentioned above, can be obtained. This debenzylation reaction can be carried out, for example, by subjecting to hydrogenolysis in the presence of a Pd/C catalyst by using an alcoholic solvent such as methanol, ethanol, propanol, etc. or acetic acid under normal pressure.

By reacting the compound represented by the formula (XXXVI) and a compound represented by the formula (XXXVII):

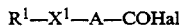

wherein $R^1$, $X^1$, A and Hal are the same as mentioned above, the desired compound represented by the above formula (I') can be obtained. The reaction can be carried out in the presence of an organic base such as pyridine, triethylamine, etc., in a solvent such as toluene, benzene, methylene chloride, etc. in a temperature range of $-20°0$ to $80°$ C.

Also, in order to produce the compound represented by the formula (I) of the present invention, the compound represented by the formula (III) to be used as a starting material can be produced by various methods.

As representative ones of the compound represented by the formula (III), there may be mentioned, for example,

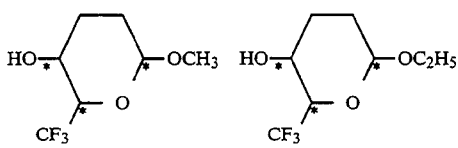

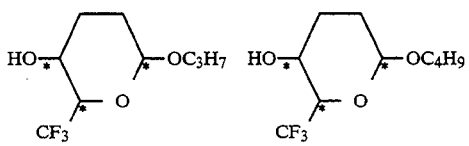

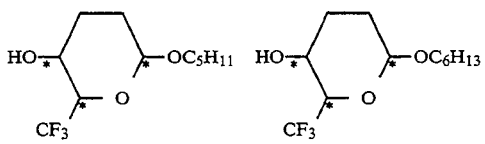

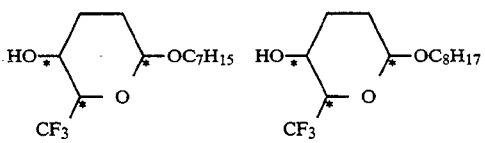

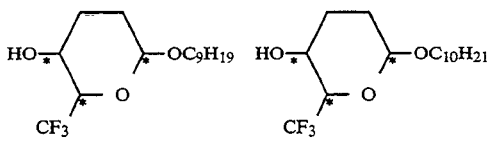

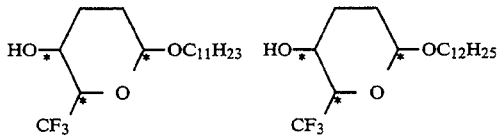

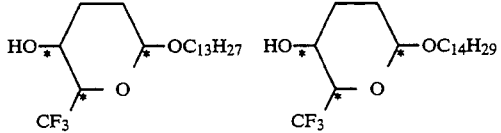

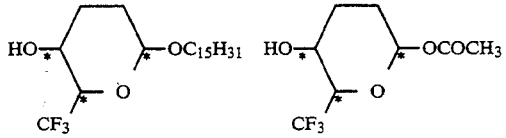

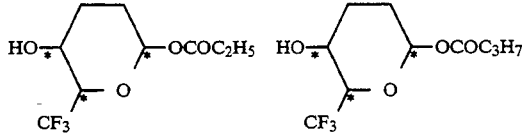

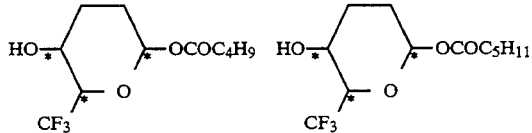

-continued
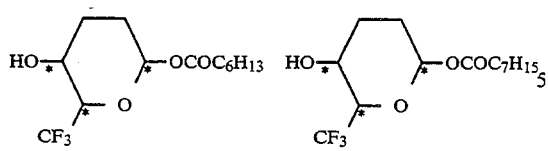
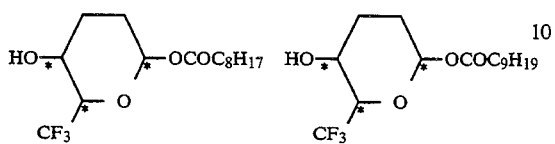
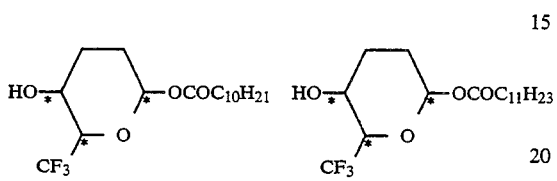
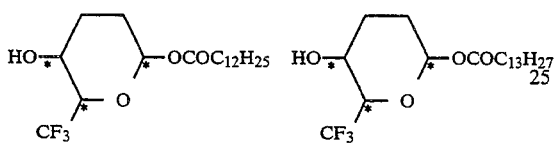
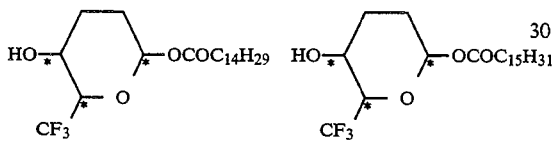
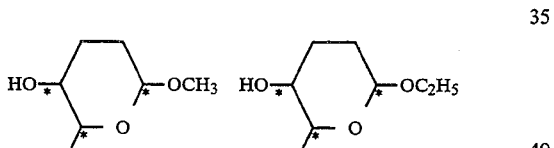
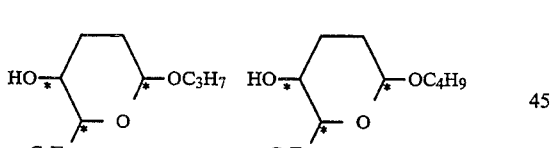
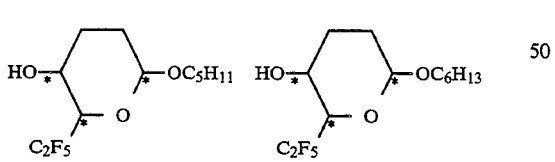
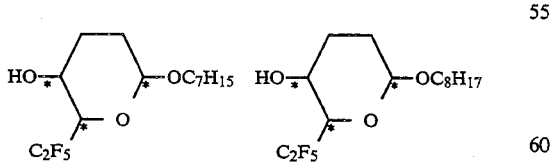
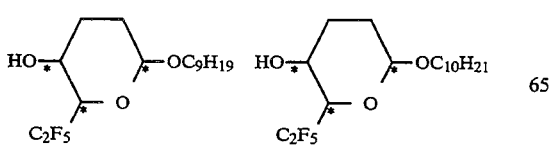
-continued
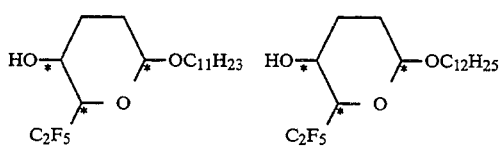
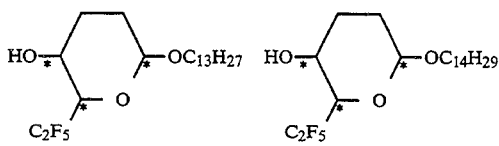
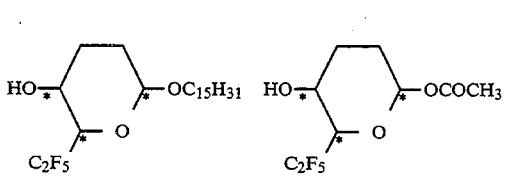
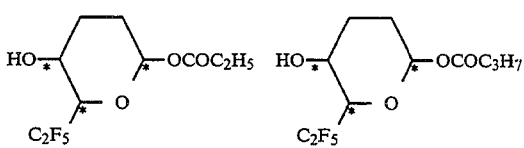
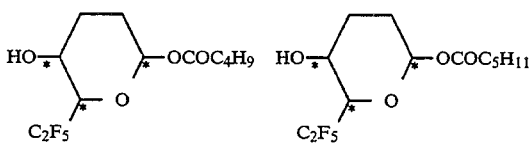
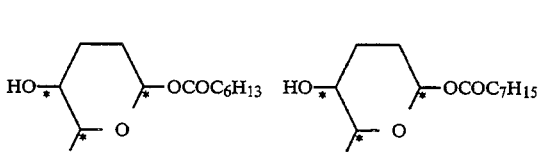
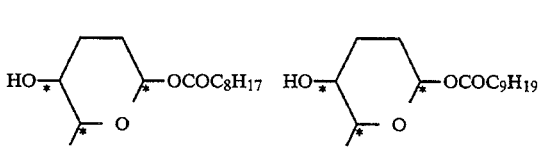
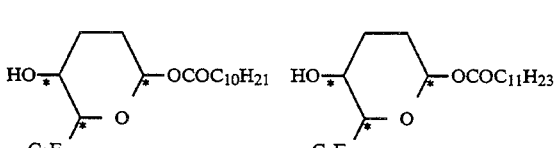
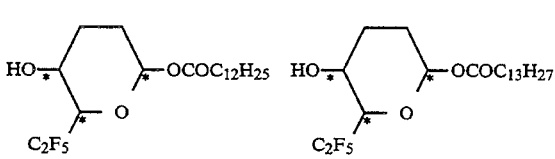
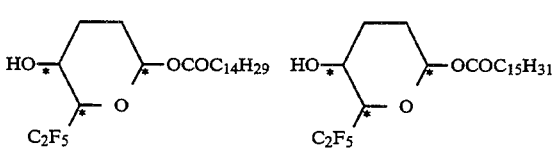

-continued
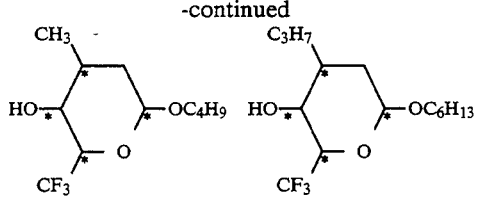
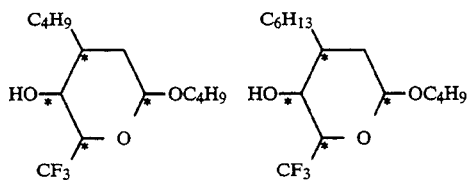
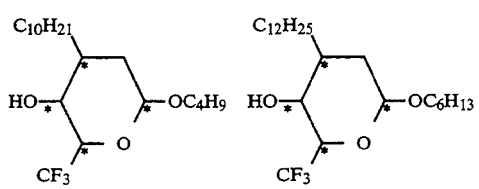
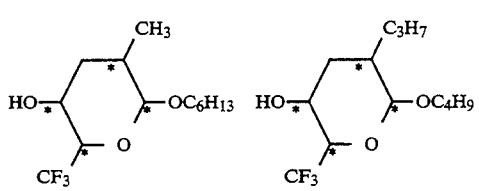
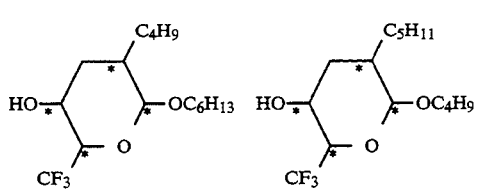
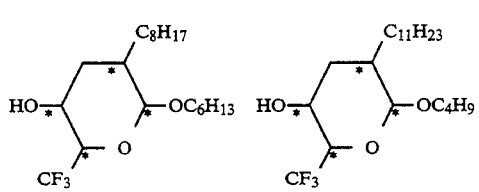
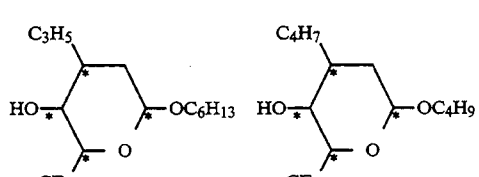
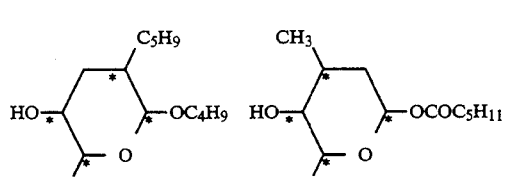
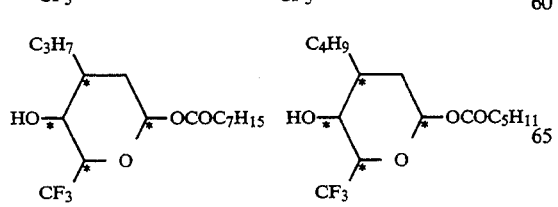
-continued
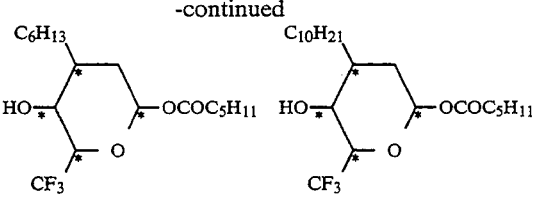
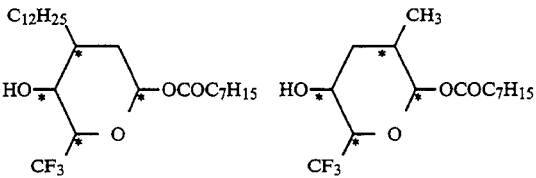
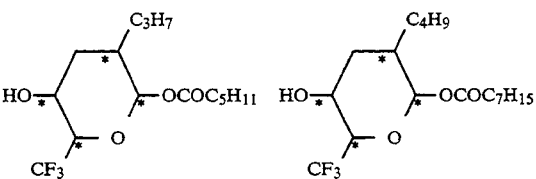
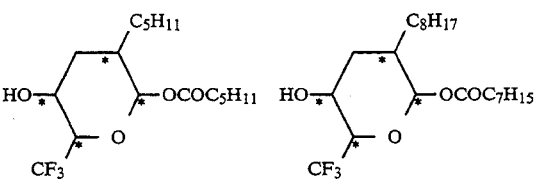
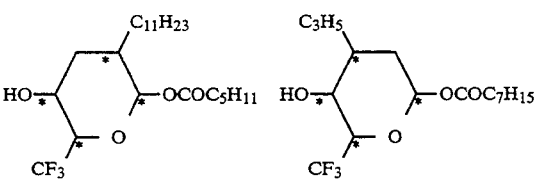
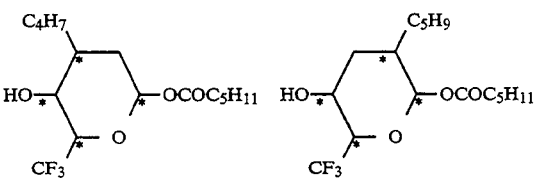
Also, as representative ones of the compounds represented by the formulae (XX) and (XXX) to be used as a starting material for producing the compound represented by the formula (I'), there may be mentioned, for example,
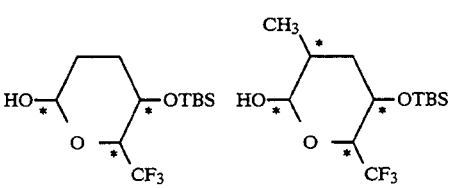
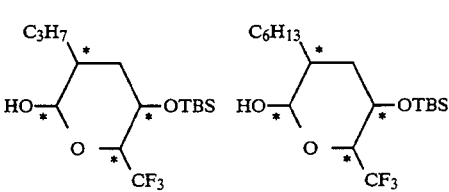

-continued
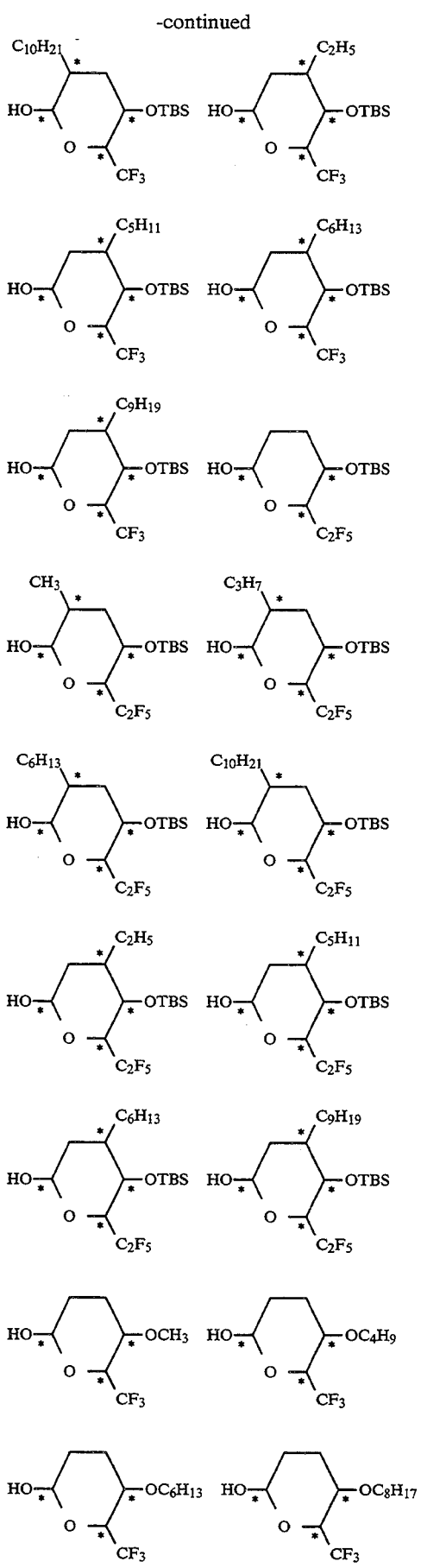
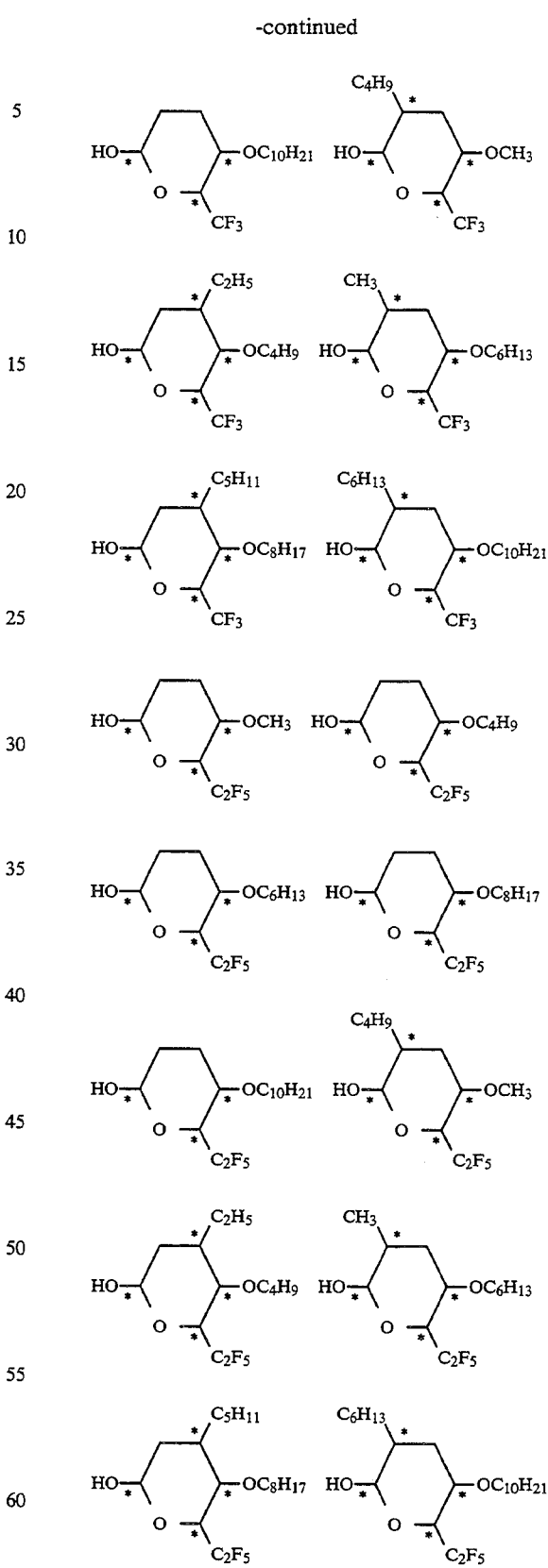
As the compound of the formula (I) of the present invention obtained as mentioned above, there may be mentioned, for example,

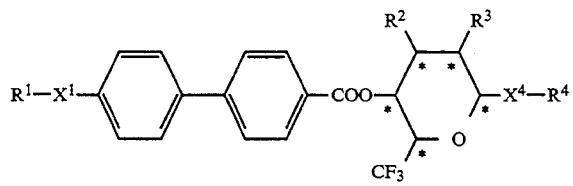
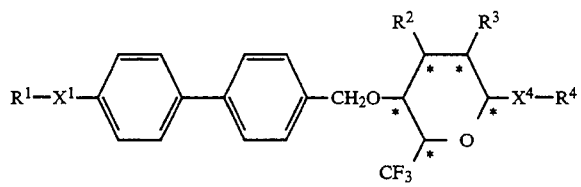
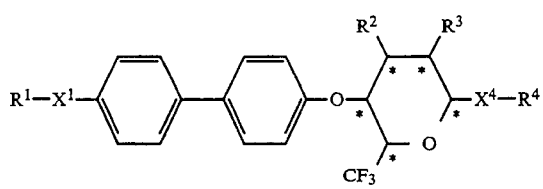
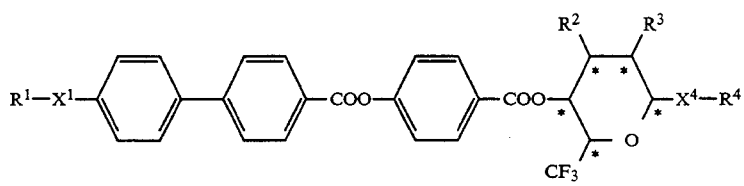
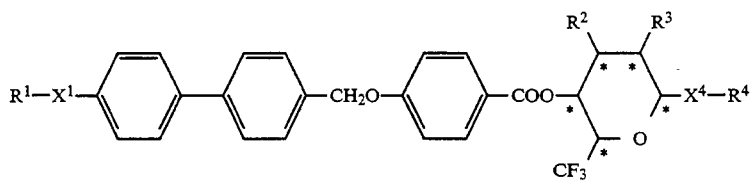
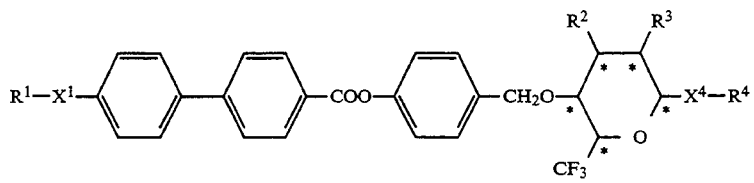
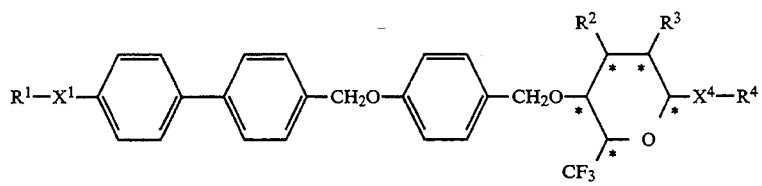
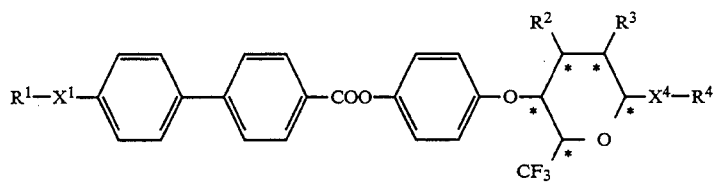

-continued
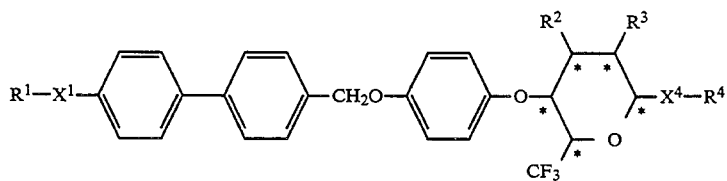
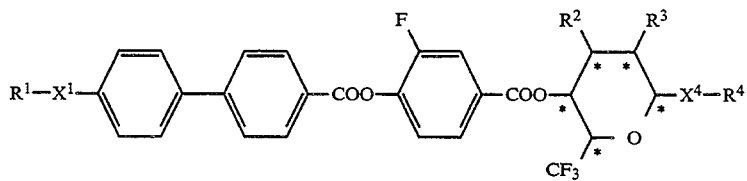
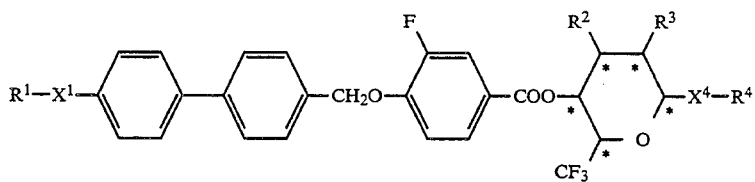
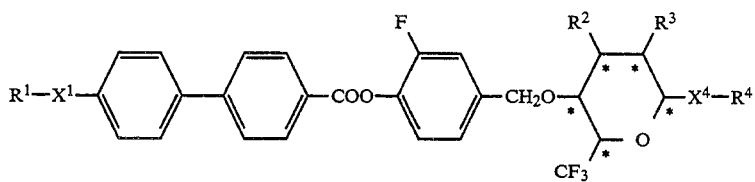
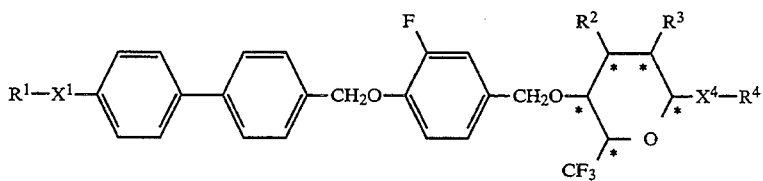
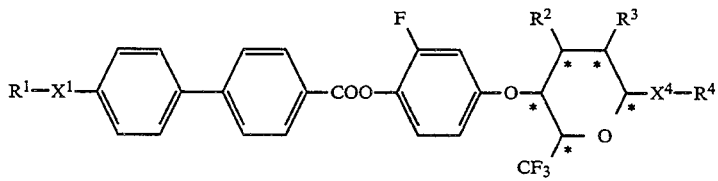
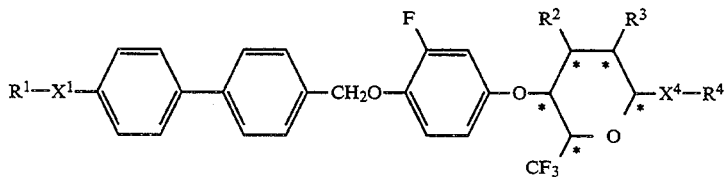
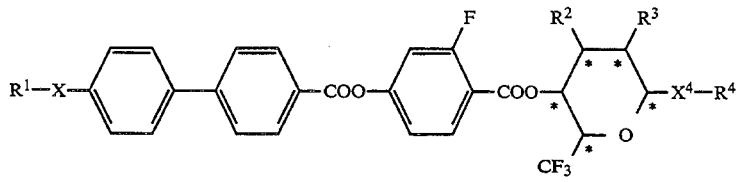

-continued
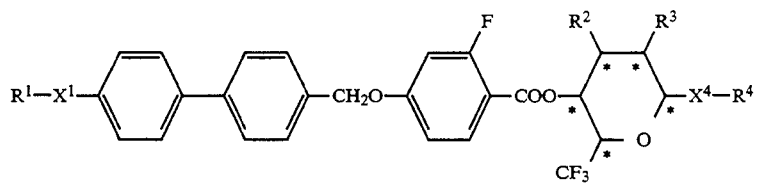
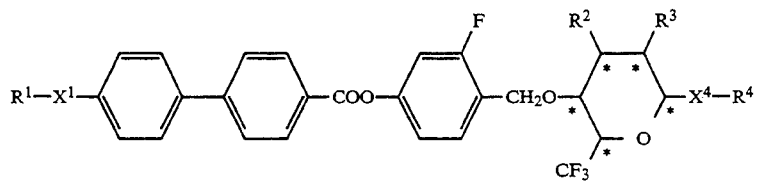
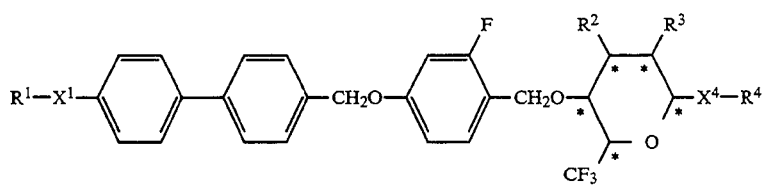
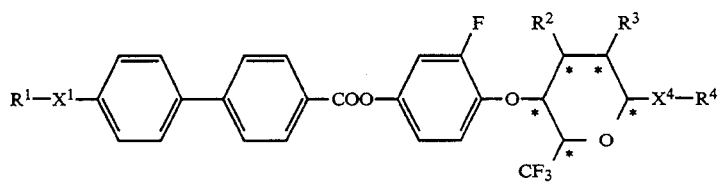
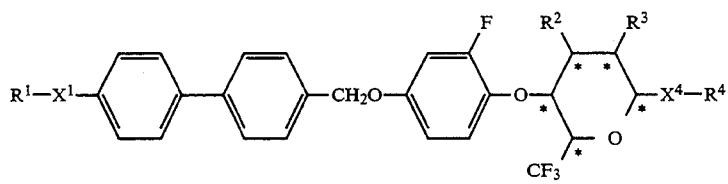
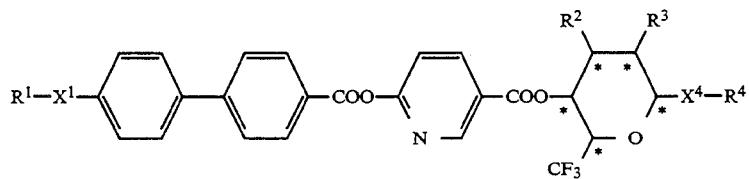
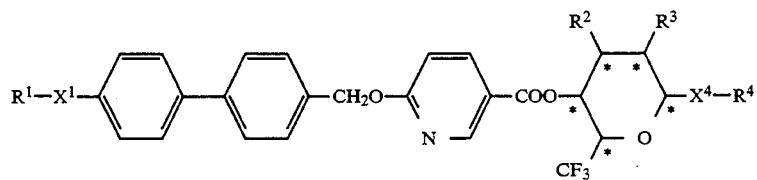
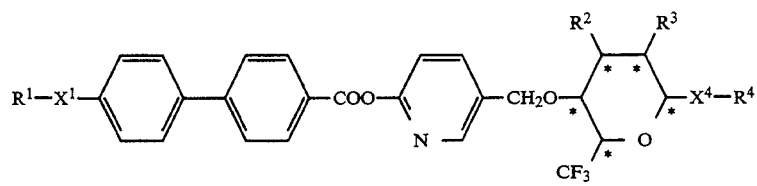

-continued
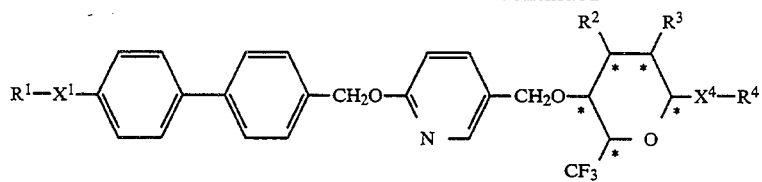
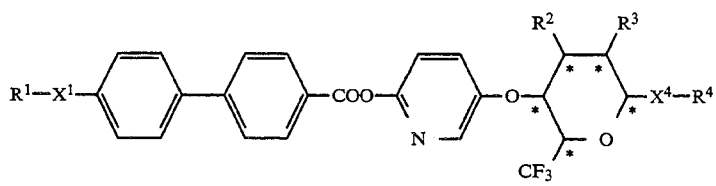
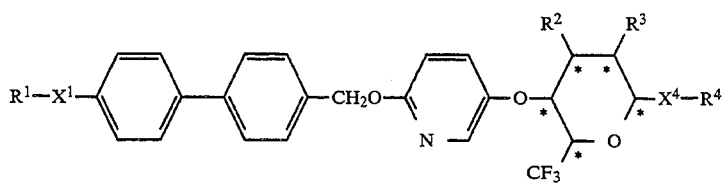
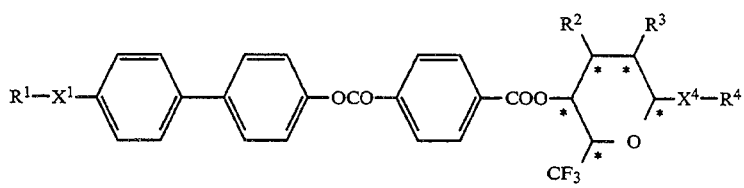
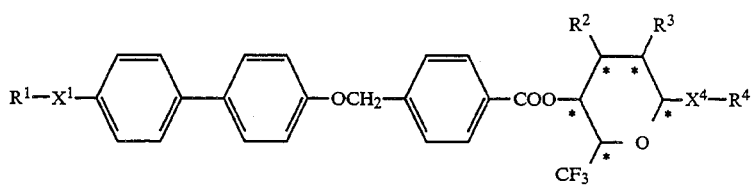
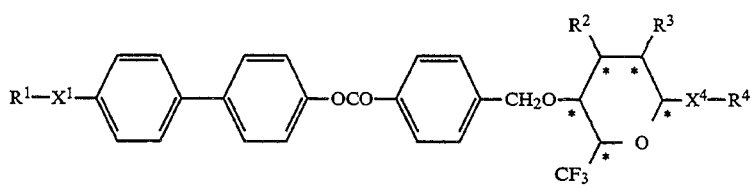
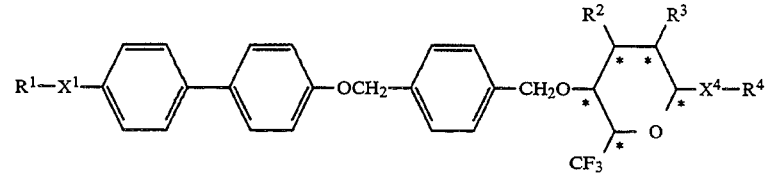
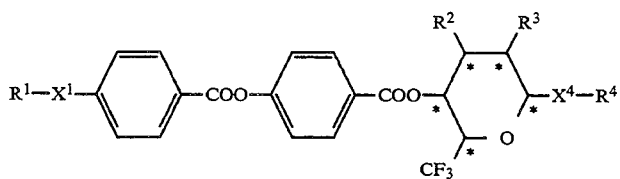
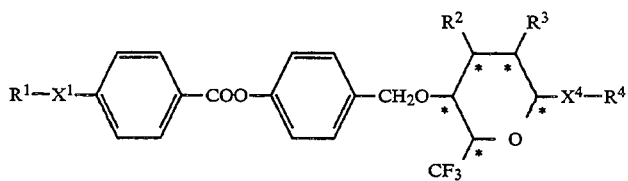

-continued
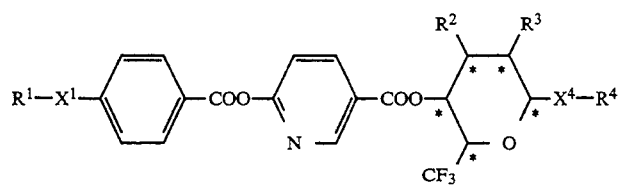
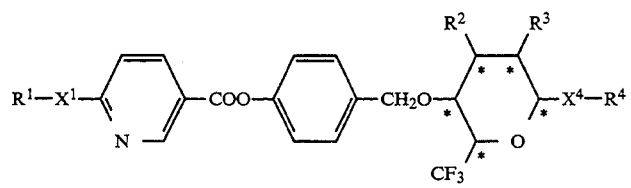
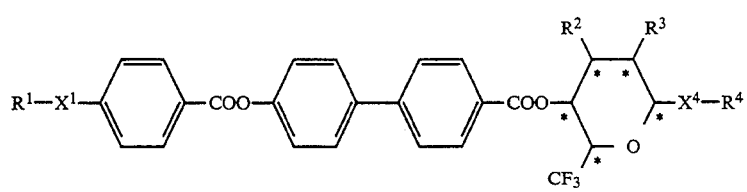
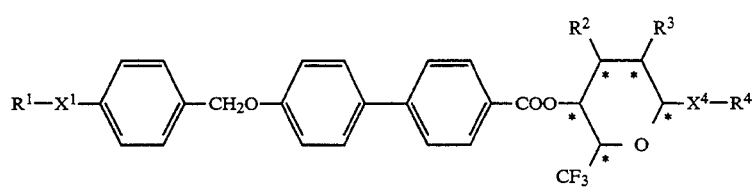
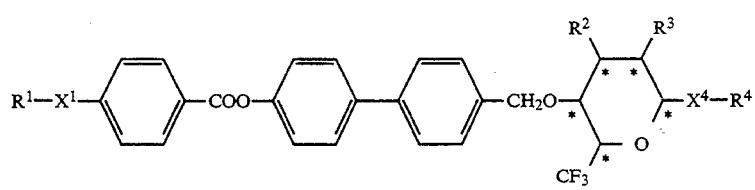
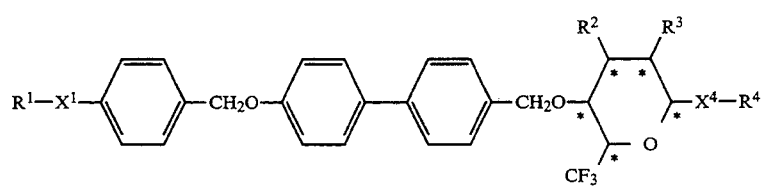
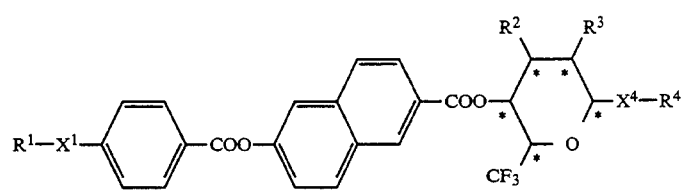
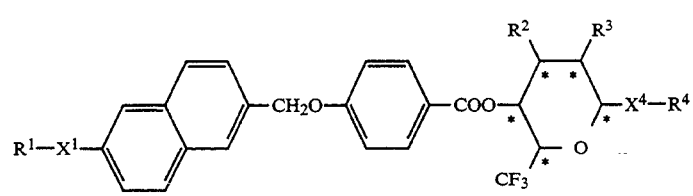

-continued
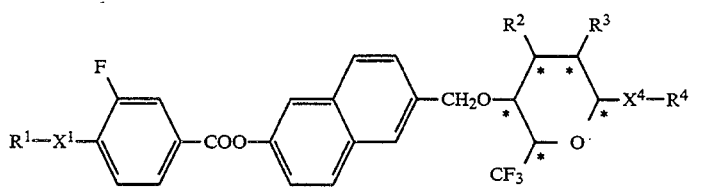
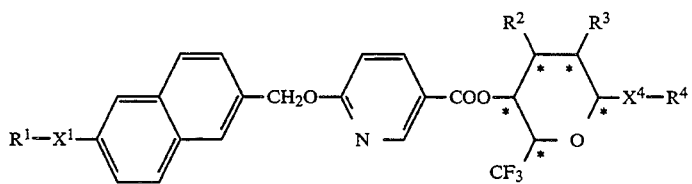
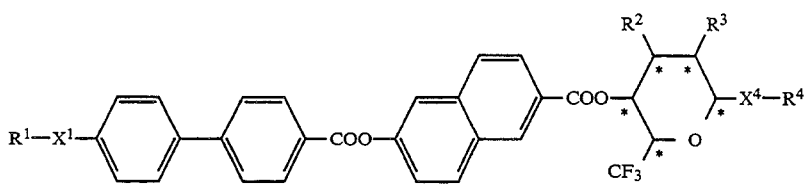
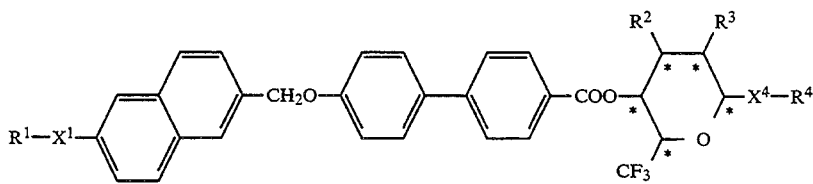
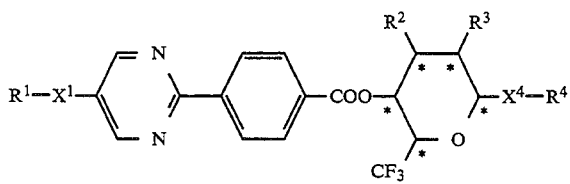
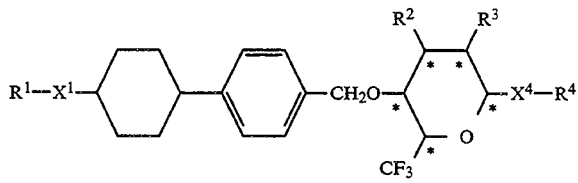
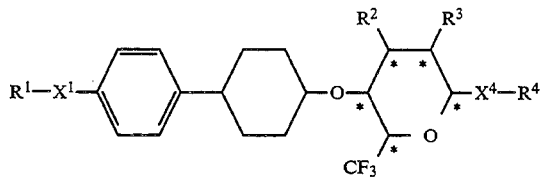
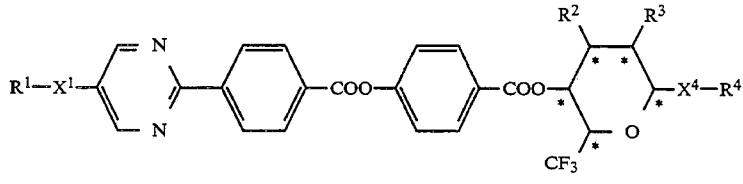

-continued
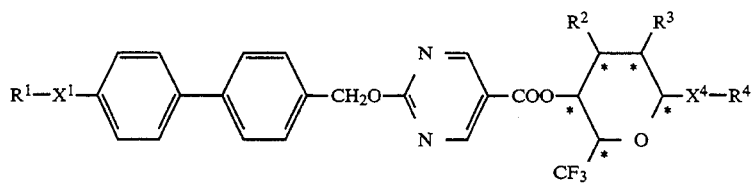
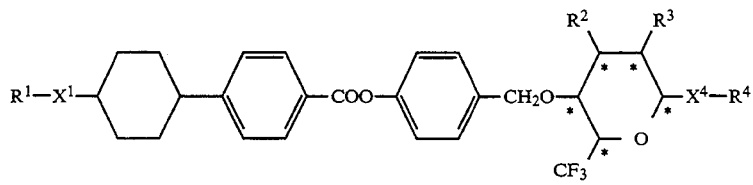
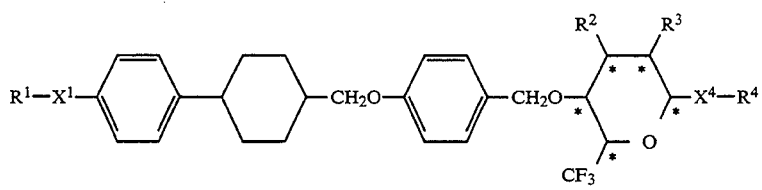
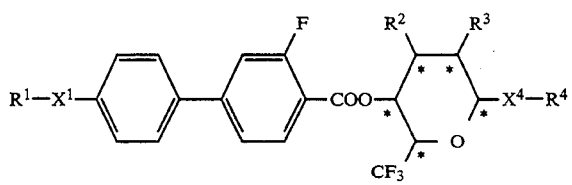
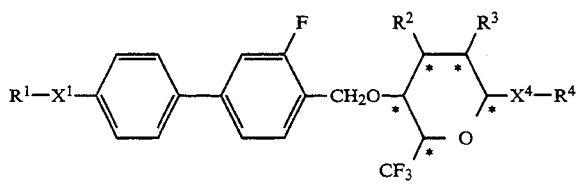
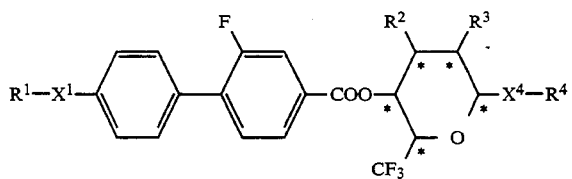
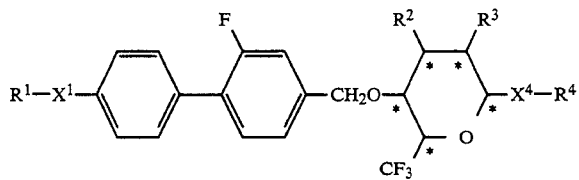
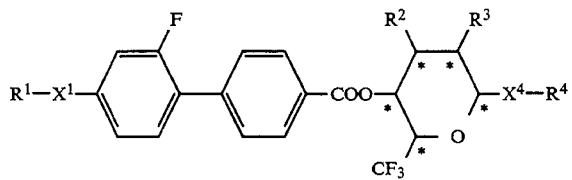

-continued
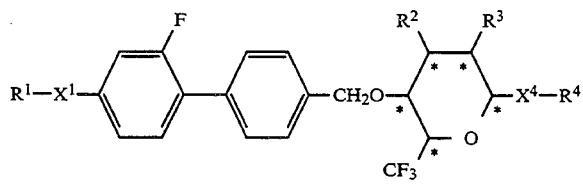
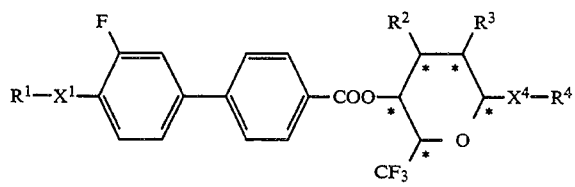
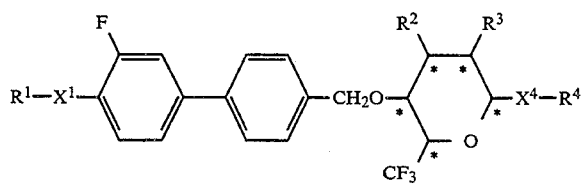
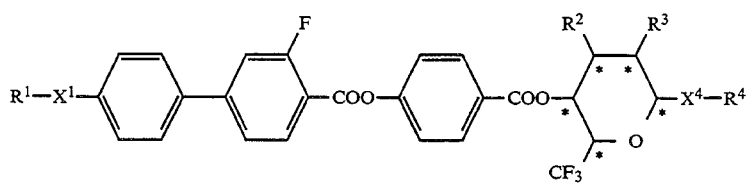
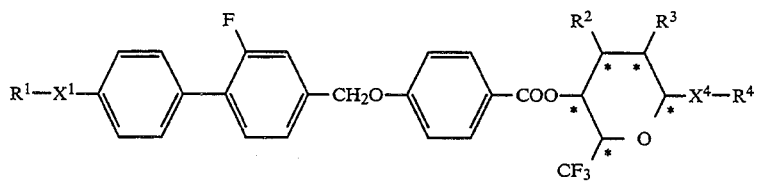
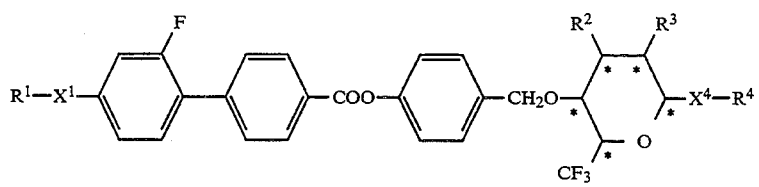
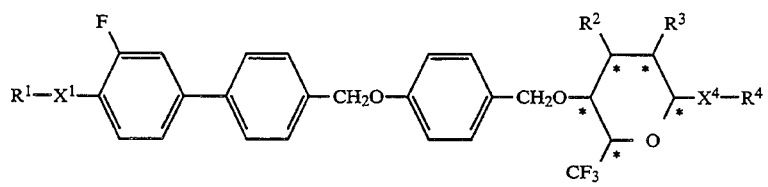
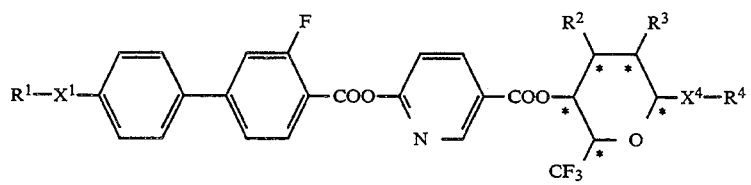

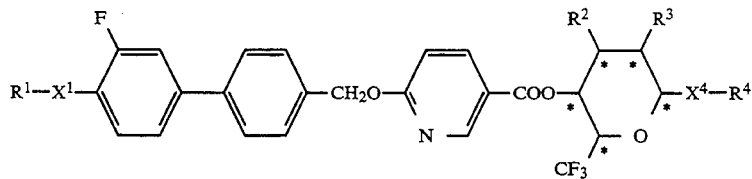
wherein $R^1$, $X^1$, $X^4$, $R^2$, $R^3$, $R^4$ and * are the same as mentioned above, etc.
Also, as the compound represented by the formula (I') of the present invention, there may be mentioned, for example,
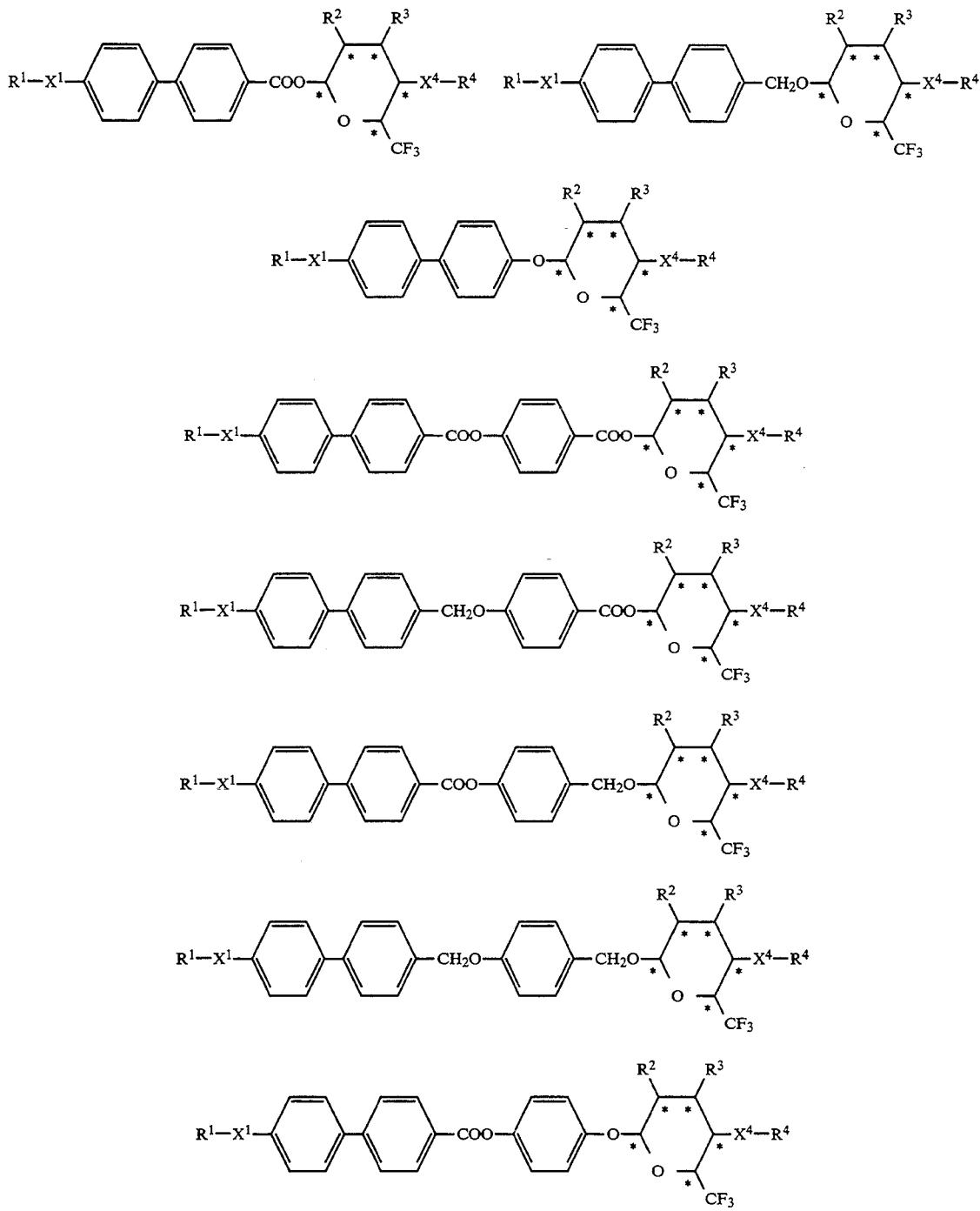

-continued
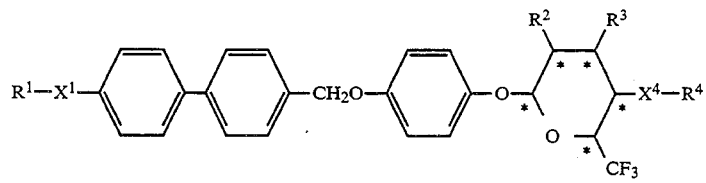
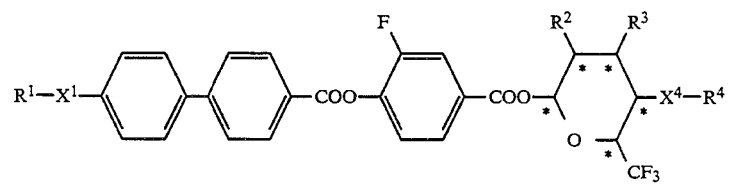
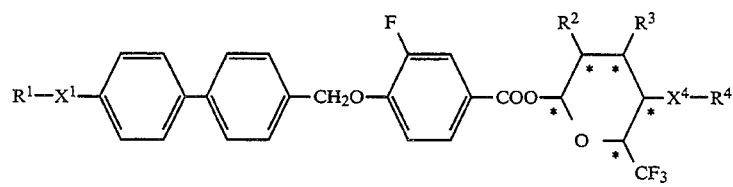
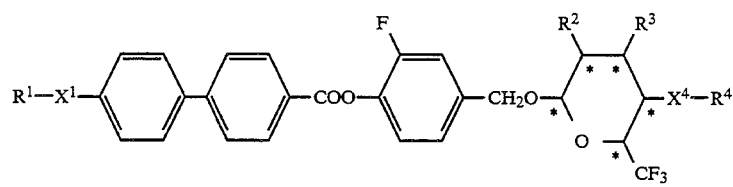
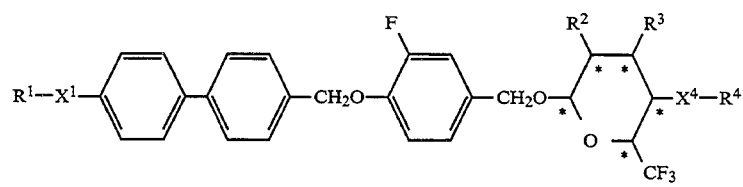
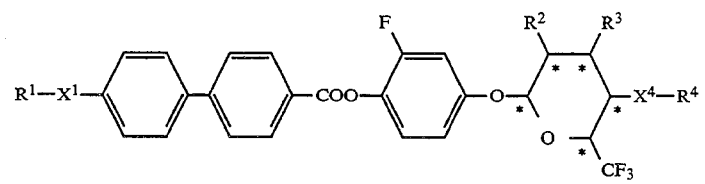
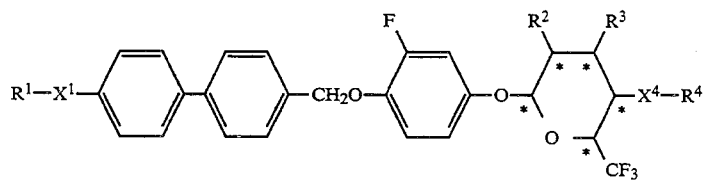
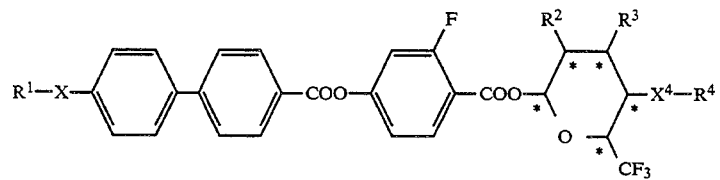

-continued
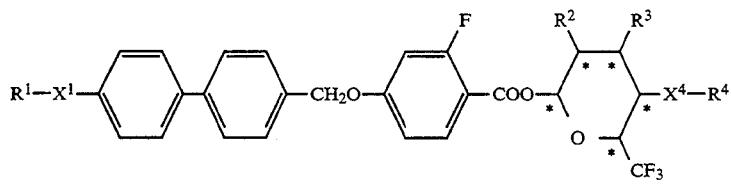
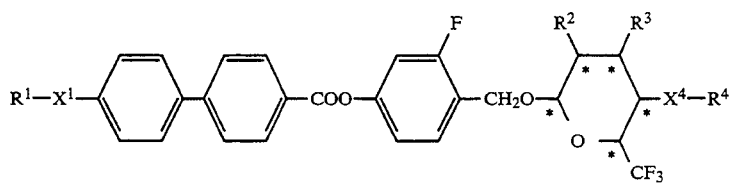
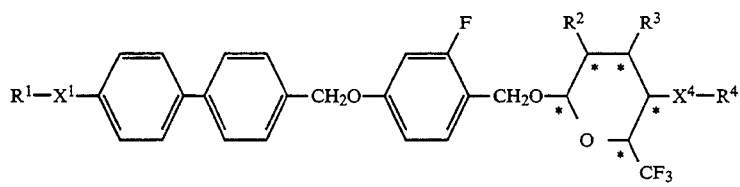
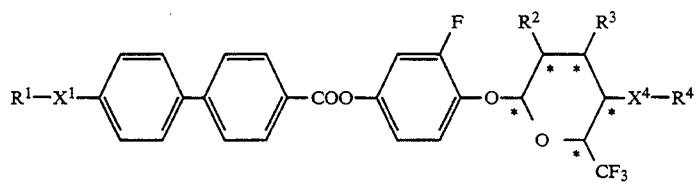
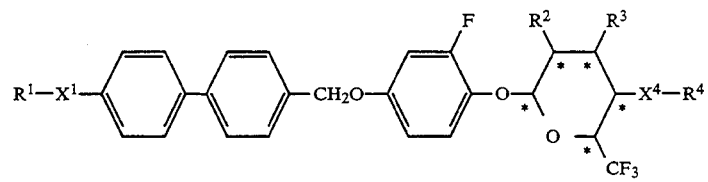
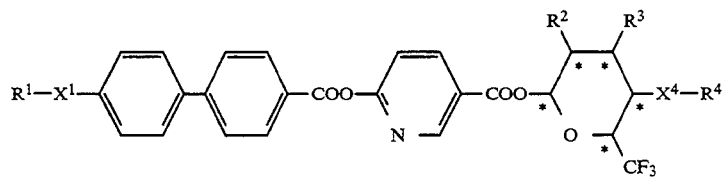
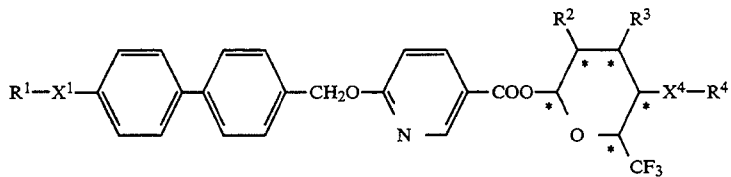
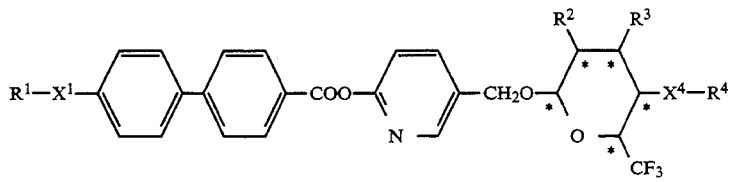

-continued
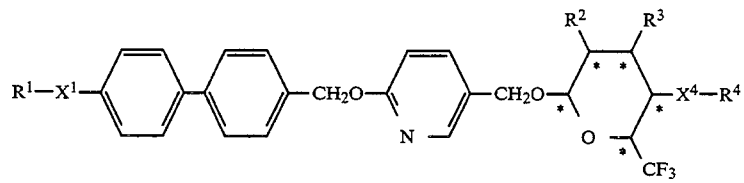
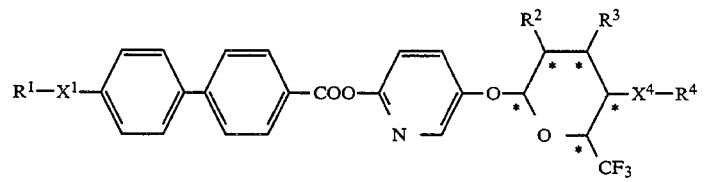
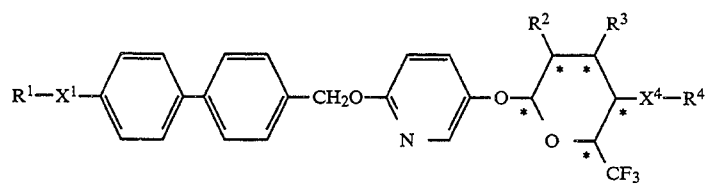
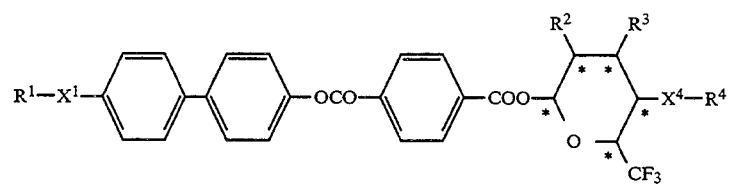
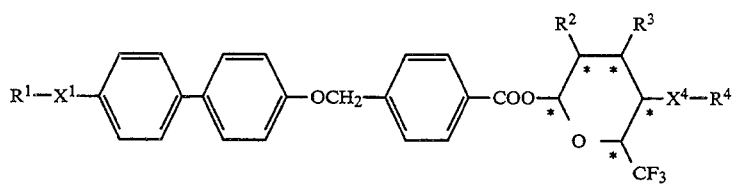
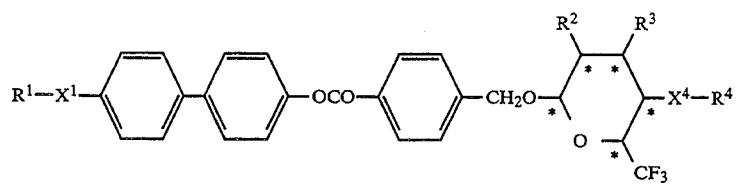
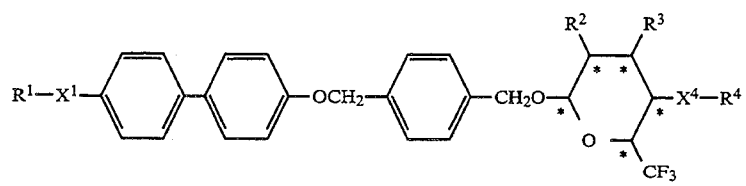
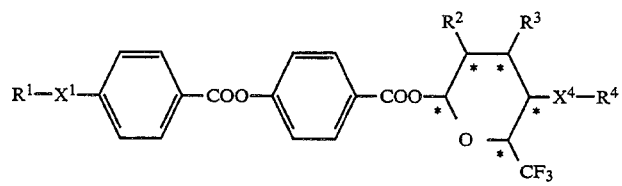

-continued
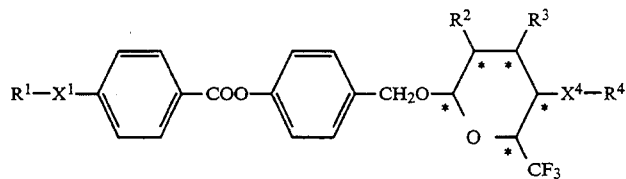
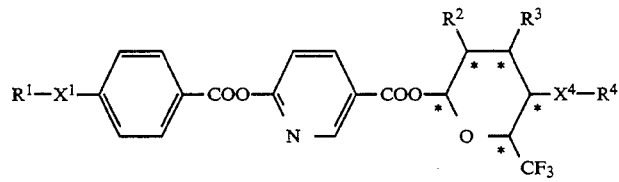
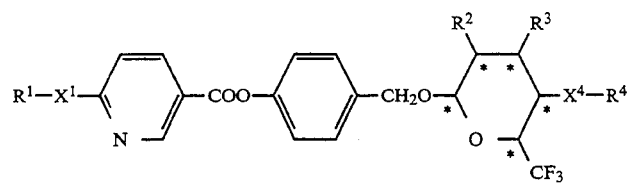
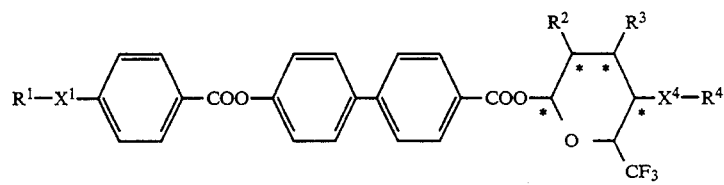
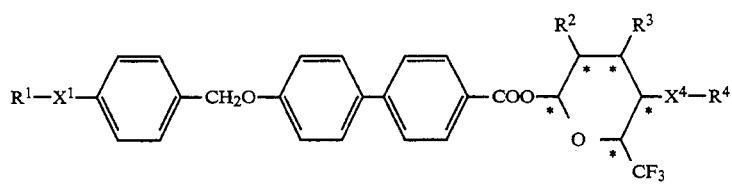
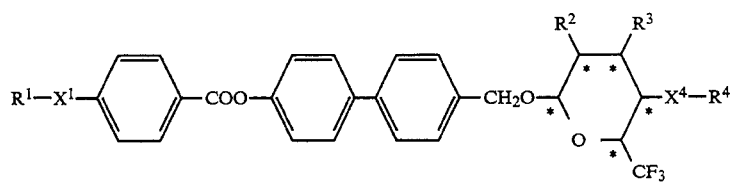
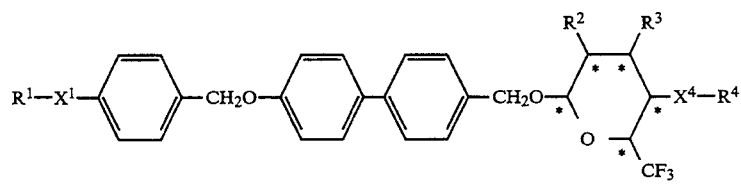
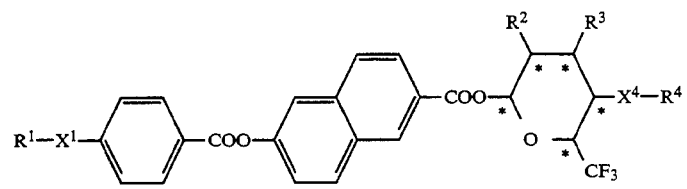

-continued
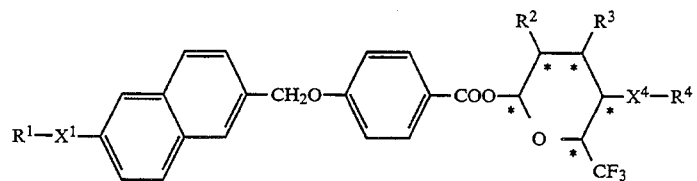
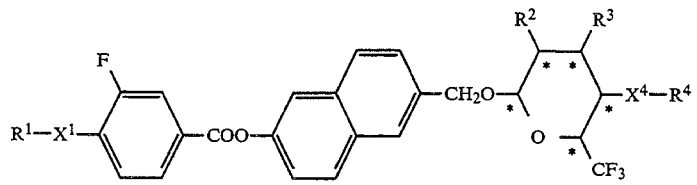
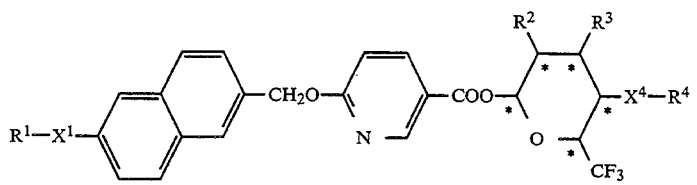
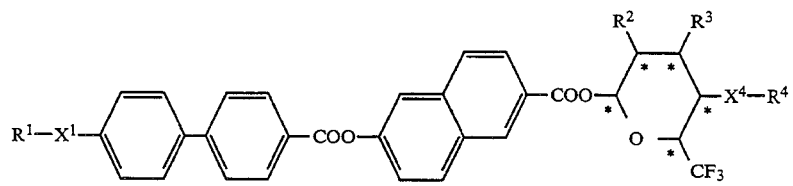
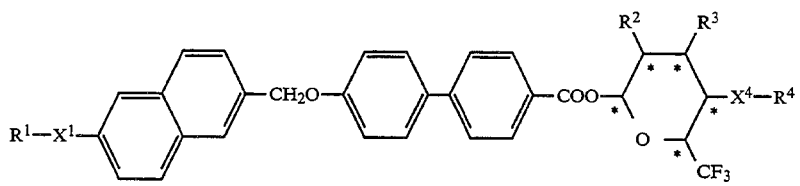
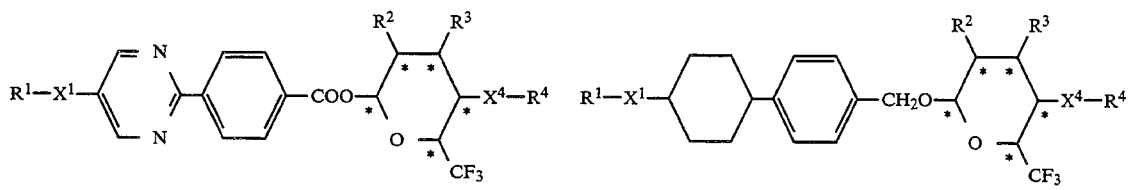
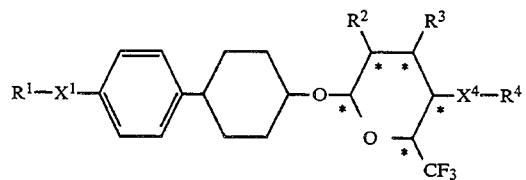
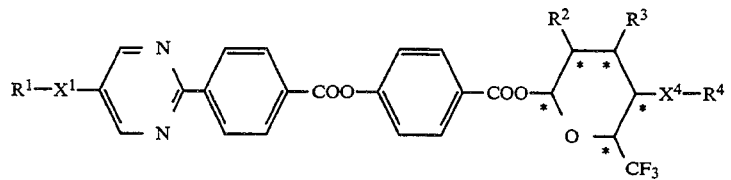

-continued
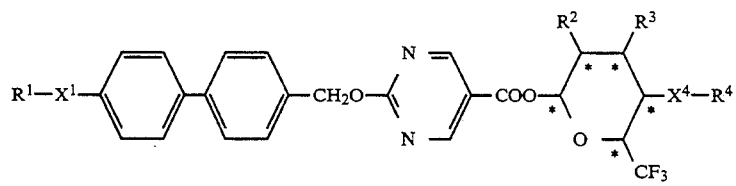
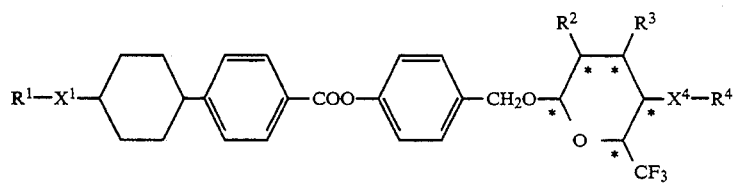
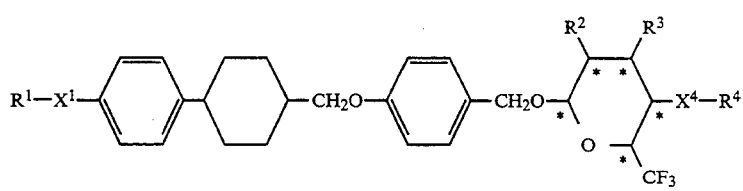
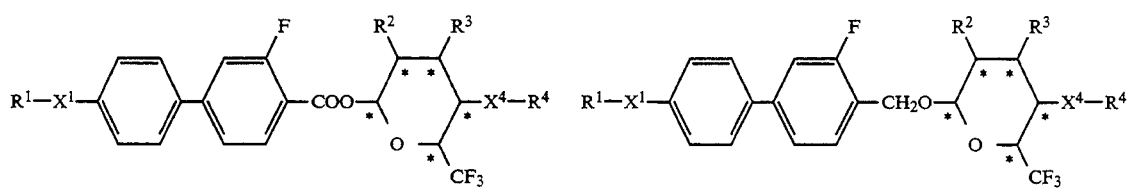
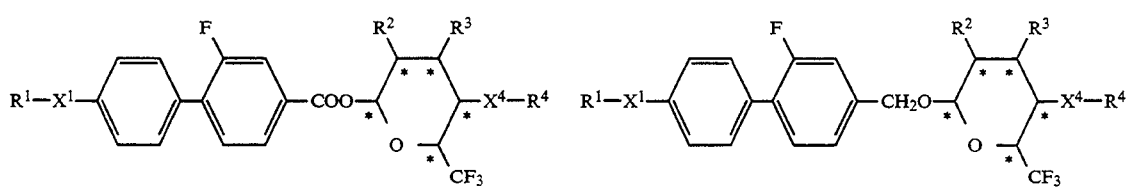
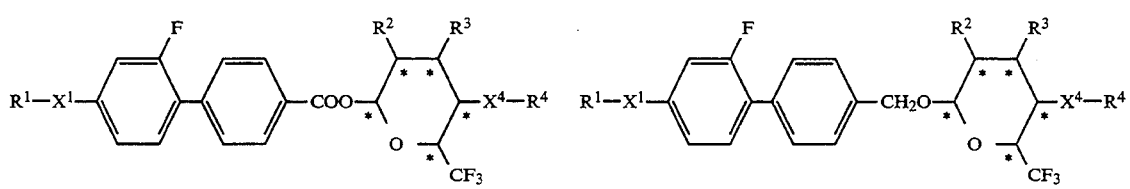
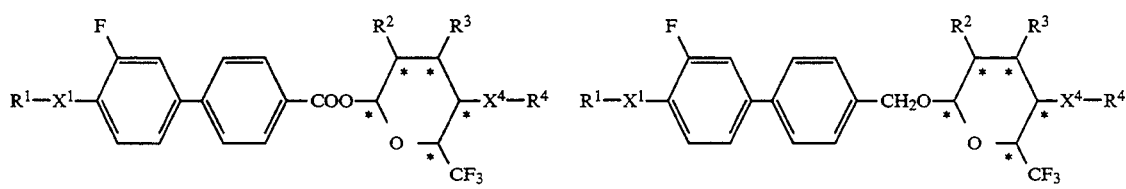
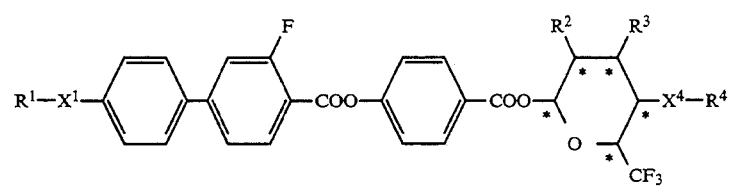

-continued

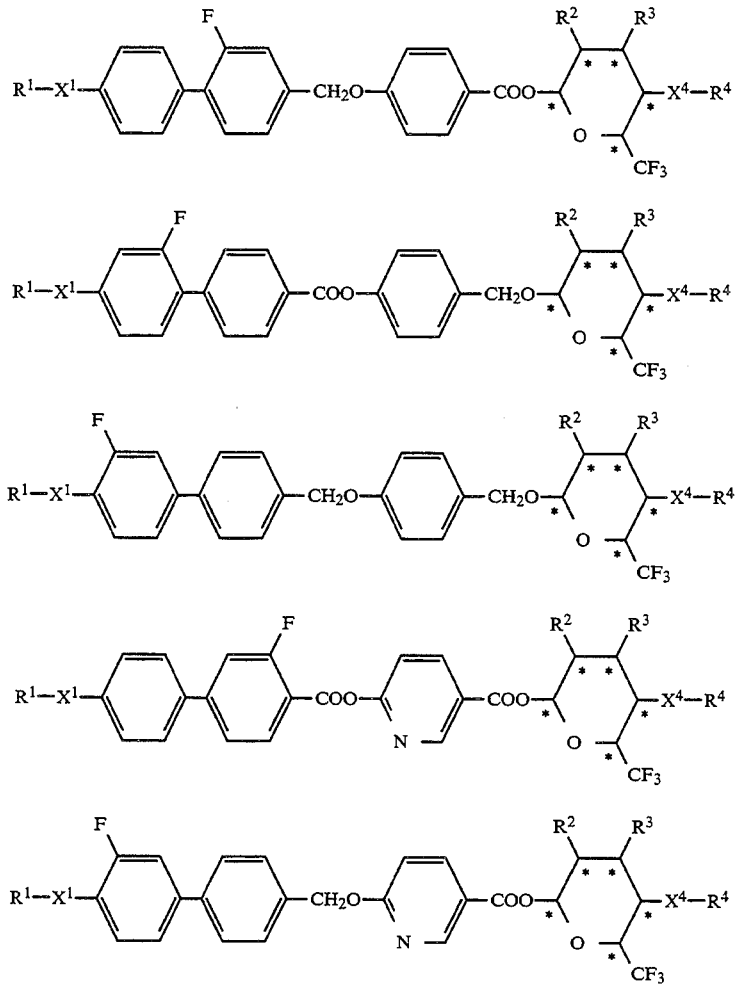

wherein $R^1$, $X^1$, $X^4$, $R^2$, $R^3$, $R^4$ and * are the same as mentioned above. etc.

In the optically active compound represented by the formula (I) or (I') of the present invention, various stereoisomers exist since it possesses 3 to 5 asymmetric carbons. Accordingly, a sign of the spontaneous polarization induced when it is added to an achiral host mixture and a helical sense of the N* phase are different depending on an optically active compound, and various types as shown in Table 1 exist.

In order to obtain a good orientation, it is necessary to unwind the helix of the N* phase, and, for example, when a cell generally having 2 μm-thick is used, it is preferred that a helical pitch (P) of the N* phase is 8 μm (4-fold of the cell thickness) or more. This helical pitch (P) becomes small in inverse proportion to an amount of the optically active compound to be added so that particularly when an amount of the optically active compound is large, it is necessary to regulate the pitch. At this time, in order for not impairing high speed response, it is preferred to mix compounds having the same sign of spontaneous polarization and reverse sense of helix of the N * phase. In particular, as optically active tetrahydropyrane derivatives, it is preferred to use at least two kinds of compounds having the same sing of spontaneous polarization and reverse sense of helix of the N* phase.

Here, helical pitch (P) of a mixed liquid crystal can be given by $$1/P = \Sigma(Ci/Pi).$$

Pi: helical pitch of a component i of an optically active component

Ci: a concentration of the component i.

Thus, by using the compounds of the present invention with various combinations, helical pitch of the N* phase can be easily regulated and a liquid crystal composition having good alignment quality can be obtained.

TABLE 1

| | | Helical sense of the N* phase | | |
|---|---|---|---|---|
| | | + | | − |
| Polarity of spontaneous polarization | + | Ia (2S,5S,6S) | Ia | (2S,5R,6R) |
| | | Ib (2S,5S,6S) | Ib | (2R,5S,6S) |
| | | I'a (2S,5S,6S) | Ib | (2R,5S,6R) |
| | | I'a (2S,5R,6R) | Ib | (2S,5S,6R) |
| | | I'b (2S,5R,6R) | I'b | (2S,5R,6S) |
| | − | Ia (2R,5S,6S) | Ia | (2R,5S,6R) |
| | | Ib (2S,5R,6R) | Ib | (2R,5R,6R) |
| | | Ib (2S,5R,6S) | I'a | (2R,5R,6R) |
| | | Ib (2R,5R,6S) | I'a | (2R,5R,6R) |
| | | I'b (2R,5S,6R) | I'b | (2R,5S,6S) |

TABLE 1-continued

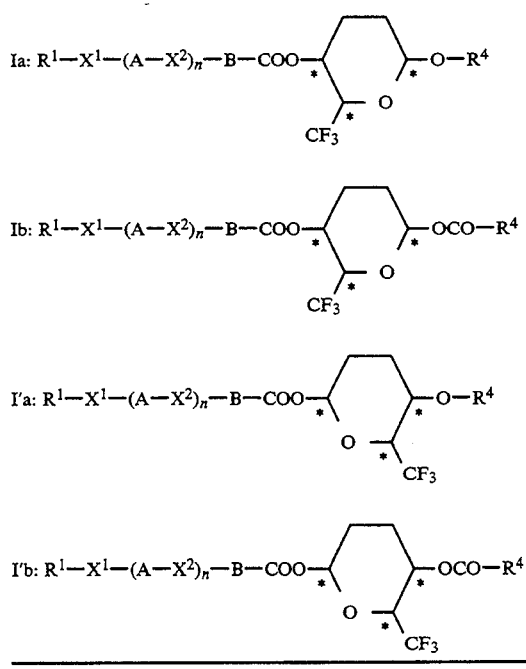

The liquid crystal composition of the present invention can be obtained by formulating
(a) at least one kind of the compound represented by the formula (I) or (I'),
(b) a compound having a chiral smectic C phase (SmC* phase) other than (a) or a mixture thereof and/or
(c) a compound having a smectic C phase (SmC phase) other than (a) or a mixture thereof.

In this case, an amount of the compound represented by the formula (I) or (I') to be formulated may be optionally selected depending on various situations, but preferably 0.1 to 99% by weight, particularly preferably 1 to 90% by weight based on the resulting liquid crystal composition.

Also, as other embodiment of the liquid crystal composition of the present invention, there may be mentioned a liquid crystal composition comprising at least two kinds of the compounds represented by the formula (I) or (I').

As the compound of the above (b) or (c) or the mixture thereof, various substances conventionally known can be used.

As the compound of the above (b), more specifically, there may be mentioned, for example, compounds described in "Structure and Physical Properties of Ferrodielectric Liquid Crystal", written by Fukuda, Takezoe, published by Corona Co. (1990), p.229, Table 7.1.

As the compound of the above (c), preferably a compound represented by the formula (A):

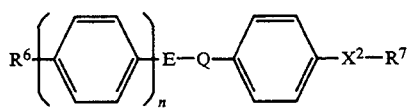

wherein $R^6$ represents an alkyl group or an alkoxy group each may have a substituent and having 1 to 15 carbon atoms, $R^7$ represents an alkyl group which may have a substituent and having 1 to 15 carbon atoms, Q represents —O—, —COO—, —OCO—, —OCOO— or a single bond, E represents

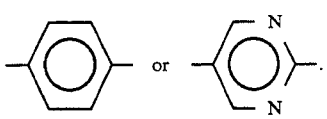

Also, $X^2$ and n are the same as mentioned above may be mentioned. More specifically, the following compounds may be mentioned.

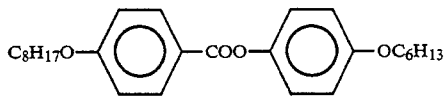

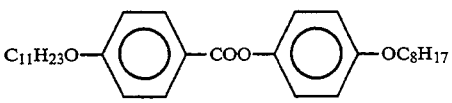

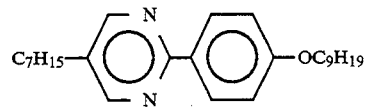

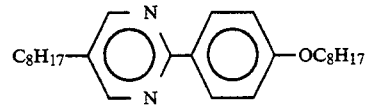

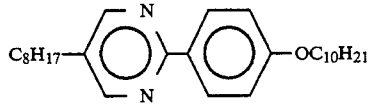

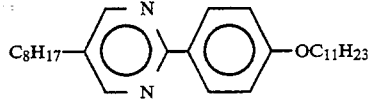

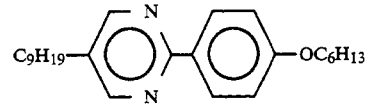

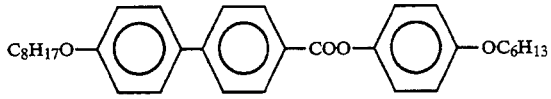

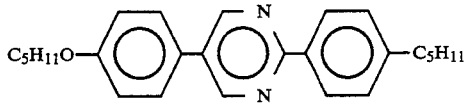

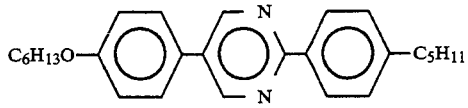

Also, the liquid crystal device of the present invention comprises providing the compound of the above formula (I) or (I') or the above liquid crystal composition between a pair of electrode substrates. The liquid crystal device can be obtained, for example, by bonding two pairs of substrates in which an orientation control film comprising a polyvinyl alcohol, polyimide, etc. on a transparent substrate having a transparent electrode comprising InO3, SnO2, ITO (mixed oxide of indium oxide and tin oxide), etc. to prepare a cell and then providing polarization plates on the both surfaces of the cell. This device can be used as a display device or an electro-optic device by utilizing a double refraction mode.

Next, the present invention will be explained more specifically by referring to Reference examples and Examples, but the present invention is not limited by them. Also, in the following respective Examples, indications of R and S of the optically active compound represented by the formula (I) or (I') of the present invention are carried out based on the positional numbers of the following formula:

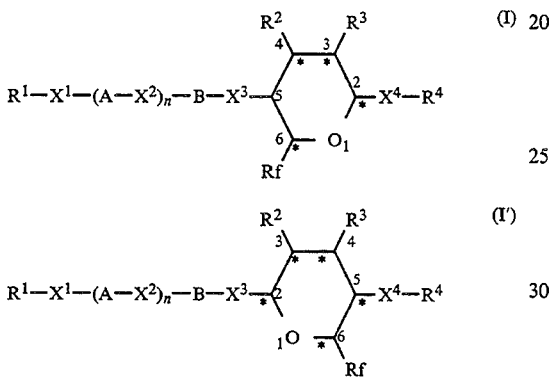

wherein $R^1$, $R^2$, $R^3$, $R^4$, $X^1$, $X^2$, $X^3$, $X^4$, A, B n and * are the same as mentioned above.

Reference Example 1

Synthesis of
(2R,5S,6S)-tetrahydro-6-trifluoromethyl-2-hexyloxy-5-hydroxypyrane and
(2S,5S,6S)-tetrahydro-6-trifluoromethyl-2-hexyloxy-5-hydroxypyrane

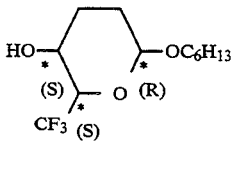

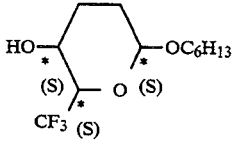

(a) Under nitrogen atmosphere, 13.6 g (200 mmol) of furan was added to 150 ml of tetrahydrofuran, and 133 ml (200 retool) of a 1.5 mol/liter n-butyl lithium-hexane solution was added dropwise at $-20°$ C. to the mixture and the mixture was reacted for one hour. Then, 21.7 g (200 mmol) of trimethylsilyl chloride was added dropwise and the mixture was stirred at $-20°$ C. for one hour. After reaction was carried out at $-20°$ C. for one hour by adding 133 ml (200 mmol) of a 1.5 mol/liter n-butyl lithium-hexane solution, 28.4 g (200 mmol) of ethyl trifluoroacetate was added dropwise at $-78°$ C., and the mixture was reacted at $-78°$ C. for one hour and at room temperature for further one hour. To the reaction mixture was added 3N hydrochloric acid to stop the reaction and the mixture was extracted with ethyl acetate. Then, the extract was washed successively with a saturated sodium hydrogen carbonate solution and brine, and dried over anhydrous magnesium sulfate.

Ethyl acetate was removed under reduced pressure to obtain a crude product of a furan derivative.

(b) To 100 ml of dried ethanol was added 2.3 g (60 mmol) of sodium borohydride, and the crude product of the furan derivative obtained by the above reaction was added dropwise at 0° C. over 30 minutes. After reaction was carried out at room temperature for 2 hours, ethanol was removed under reduced pressure, the reaction was stopped by adding 3N hydrochloric acid and the reaction mixture was extracted with ethyl acetate.

Then, the extract was washed successively with a saturated sodium hydrogen carbonate solution and brine, and dried over anhydrous magnesium sulfate. After ethyl acetate was removed under reduced pressure, distillation was carried out under reduced pressure to obtain 40.5 g (170 mmol) of an alcohol compound.

(c) In 200 ml of methylene chloride were added 23.8 g (100 mmol) of the alcohol compound obtained by the reaction as mentioned above (b) and 8.9 ml (110 mmol) of pyridine, and then 8.6 g (110 mmol) of acetyl chloride was added dropwise to the mixture at 0° C. and reacted at room temperature for 12 hours. Then, the reaction was stopped by adding 3N hydrochloric acid and the reaction mixture was extracted with methylene chloride. Then, the extract was washed successively with a saturated sodium hydrogen carbonate solution and distilled water, and dried over anhydrous magnesium sulfate. After methylene chloride was removed under reduced pressure, distillation was carried out under reduced pressure to obtain 27.5 g (98 mmol) of an ester compound.

(d) To 1000 ml of distilled water was added 28.0 g (100 mmol) of the ester compound obtained in the aforesaid reaction, and the mixture was stirred in a mini-jar fermentor at 40° C. To the mixture was added 20 g of Lipase PS and the mixture was reacted for 20 hours. The reaction was stopped by adding 3N hydrochloric acid, and the reaction mixture was cooled to 0° C. and filtered by using Celite. The filtrate was extracted with ethyl acetate, the extract was washed with brine, dried over anhydrous magnesium sulfate and ethyl acetate was removed under reduced pressure. Then, the residue was separated and purified by silica gel column chromatography to obtain 11.7 g (49 mmol) of an optically active alcohol compound and 13.2 g (47 mmol) of an optically active ester compound. Incidentally, the resulting alcohol compound had an optical purity of 97.5 % e.e.

(e) In 100 ml of methylene chloride was dissolved 11.7 g (49 mmol) of the optically active alcohol compound obtained in the aforesaid reaction, and 4.0 g (59 mmol) of imidazole and 8.9 g (59 mmol) of t-butyldimethylsilyl chloride were added to the solution at 0° C. and the mixture was stirred for 15 minutes and reacted at room temperature for 16 hours. The reaction was stopped by adding distilled water and the reaction mixture was extracted with methylene chloride. Then, the extract was washed with distilled water and dried over anhydrous magnesium sulfate. After removing methylene chloride under reduced pressure, the residue was separated and purified by column chromatography to obtain 16.6 g (47 mmol) of a silyl ether compound.

(f) Under nitrogen atmosphere, to 120 ml of acetic acid were added ]4.1 g (40 mmol) of the silyl ether compound obtained in the aforesaid reaction and 23.2 g (60 mmol) of magnesium monoperoxyphthalate, and the mixture was reacted at 80° C. for 12 hours. After removing acetic acid under reduced pressure, a saturated sodium hydrogen carbonate solution was added to the residue and the mixture was extracted with ethyl acetate. After removing ethyl acetate under reduced pressure, the residue was separated and purified by column chromatography to obtain 4.7 g (16 mmol) of a (4S,1'S)butenoride compound and 3.0 g (10 mmol) of a (4R,1'S)butenoride compound. Incidentally, 4.2 g (12 mmol) of the starting material was also recovered.

(g) In 40 ml of ethanol were dissolved 13.7 g (46 mmol) of the (4S,1'S) and (4R,1'S)butenoride compounds without separation, and 1.4 g of a 10% Pd/C (containing 10 % by weight of Pd) was added to the solution and under hydrogen atmosphere, the mixture was reacted at room temperature for 15 hours. After the reaction mixture was filtered and the solvent was removed under reduced pressure, the residue was separated and purified by silica gel column chromatography to obtain 8.2 g (29 mmol) of a (4S,1'S)butenoride compound and 3.6 g (12 mmol) of a (4R,1'S) butenoride compound.

(h) Under nitrogen atmosphere, to 40 ml of diethyl ether was added 7.5 g (25 mmol) of (4S,1'S)butanoride compound obtained in the aforesaid reaction, and then 32 ml (30 mmol) of a 0.93 mol/liter diisobutyl aluminum hydride dissolved in n-hexane solution was added dropwise to the mixture at −78° C. and reacted for 3 hours. The reaction was stopped by adding distilled water, and the reaction mixture was neutralized by adding 1N hydrochloric acid and extracted with diethyl ether.

The extract was washed with brine and then dried over anhydrous magnesium sulfate, and diethyl ether was removed under reduced pressure. Then, the residue was purified by silica gel column chromatography to obtain 7.3 g (24 mmol) of a lactol compound.

(i) Under nitrogen atmosphere, to 50 ml of tetrahydrofuran was added 7.3 g (24 mmol) of the lactol compound obtained in the aforesaid reaction, and 10 ml of tetrahydrofuran solution containing 3.0 g (27 mmol) of potassium t-butoxide was added dropwise to the mixture at −78° C. and reacted for 3 hours. The reaction was stopped by adding distilled water, and the reaction mixture was neutralized by adding 1N hydrochloric acid and extracted with diethyl ether. The extract was washed with brine and then dried over anhydrous magnesium sulfate, and diethyl ether was removed under reduced pressure. Then, the residue was purified by silica gel column chromatography to obtain 6.4 g(21 mmol) of a pyranose compound.

(j) In 40 ml of hexanol was dissolved 6.4 g (21 mmol) of the pyranose compound obtained in the aforesaid reaction, and 0.1 g of para-toluenesulfonic acid was added to the solution and reacted at room temperature for 18 hours. The reaction mixture was purified by silica gel column chromatography without any treatment to obtain 8.0 g (21 mmol) of an acetal compound. Also, the resulting compound was a diastereomer mixture but used in the subsequent reaction without isolation.

(k) In 20 ml of tetrahydrofuran was dissolved 8.0 g (21 mmol) of the acetal compound obtained in the aforesaid reaction, and 10 ml of a 1.0 mol/liter tetra-n-butyl ammonium fluoride dissolved in tetrahydrofuran solution was added to the mixture and reacted at 0° C. for one hour and at room temperature for 40 hours. The reaction was stopped by adding distilled water and the reaction mixture was extracted with diethyl ether.

Then, the extract was washed with brine and dried over anhydrous magnesium sulfate. After removing diethyl ether under reduced pressure, the residue was separated and purified by silica gel column chromatography to obtain desired 3.0 g (11 mmol) of (2R,5S,6S)-tetrahydro-6-trifluoromethyl-2-hexyloxy-5-hydroxypyrane and 2.3 g (8 mmol) of (2S,5S,6S)-tetrahydro-6-trifluoromethyl-2-hexyloxy-5-hydroxypyrane. Physical properties of the resulting compounds are shown below.

(1) (2R,5S,6S) isomer

Molecular formula: $C_{12}H_{21}F_3O_3$ $^1$H-NMR (proton nuclear magnetic resonance method); δ (ppm) 0.88 (t, J=6.5 Hz, 3H) 1.20∼1.39 (m, 6H) 1.50∼1.71 (m, 4H) 1.83∼2.04 (m, 2H) 2.13∼2.22 (m, 1H) 3.46 (dt, J=9.4, 6.9 Hz, 1H) 3.66 (dq, J=8.9, 6.3 Hz, 1H) 3.81∼3.93 (m, 2H) 4.52 (dd, J=2.0, 8.7 Hz, 1H)

$^{19}$F-NMR (nuclear magnetic resonance method using isotope fluorine, standard: CFCl$_3$); δ (ppm) −75.13 (d, J=6.3 Hz)

IR (infrared absorption: cm$^{-1}$) 3450, 1275, 1170, 1130, 1145, 1090, 940

Mass analysis m/e (M$^+$+H)

Calculated 271.1521

Found 271.1512

$[\alpha]_D^{25}$=−36.0° (C (concentration)=1.05, solvent: methanol).

(2) (2S,5S,6S) isomer

Molecular formula: $C_{12}H_{21}F_3O_3$ $^1$H-NMR; δ (ppm) 0.90 (t, J=7.3 Hz, 3H) 1.23∼1.45 (m, 6H) 1.52∼1.67 (m, 2H) 1.76∼2.00 (m, 5H) 3.42 (dt, J=9.7, 6.4 Hz, 1H) 3.68 (dt, J=9.7, 6.8 Hz, 1H) 3.79∼3.98 (m, 2H) 4.86 (m, 1H)

$^{19}$F-NMR (standard: CFCl$_3$) δ (ppm) −75.17 (d, J=6.2 Hz)

IR (cm$^{-1}$) 3400, 1270, 1175, 1130, 1045, 945

Mass analysis m/e (M$^+$+H)

Calculated 271.1521

Found 271.1493

$[\alpha]_D^{25}$+86.5 ° (C=1.08, solvent: methanol)

Reference Example 2

Synthesis of
(2R,5S,6S)-tetrahydro-2-butoxy-6-trifluoromethyl-5-hydroxypyrane and
(2S,5S,6S)-tetrahydro-2-butoxy-6-trifluoromethyl-5-hydroxypyrane

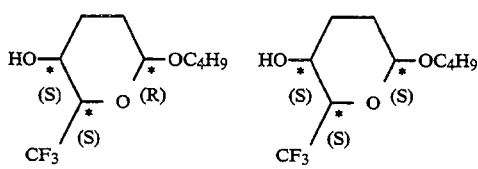

(a) In 15 ml of butanol was dissolved 1.7 g (5.7 mmol) of the pyranose compound obtained by Reference example 1 (i), and the same procedures as in Reference example 1 (j) were carried out to obtain 1.9 g (5.3 mmol) of an acetal compound. The resulting compound was a diastereomer mixture but used in the subsequent reaction without isolation.

(b) By using 1.9 g (5.3 mmol) of the acetal compound obtained in the aforesaid reaction, the same procedures as in Reference example 1 (k) were carried out to obtain a desired 0.64 g (2.6 mmol) of (2R,5S,6S)-tetrahydro-2-butoxy-6-trifluoromethyl-5-hydroxypyrane and 0.59 g (2.4 mmol) of (2S,5S,6S)-tetrahydro-2-butoxy-6-trifluoromethyl-5-hydroxypyrane.

Physical properties of the obtained compounds are shown below.

(1) (2R,5S,6S) isomer

Molecular formula: $C_{10}H_{17}F_3O_3$ $^1$H-NMR; δ (ppm) 0.92 (t, J=7.3 Hz, 3H) 1.30~1.45 (m, 2H) 1.52~1.65 (m, 4H) 1.88~2.22 (m, 3H) 3.47 (dt, J=9.5, 6.8 Hz, 1H) 3.67 (dq, J=9.0, 6.2 Hz, 1H) 3.79~3.96 (m, 2H) 4.52 (dd, J=2.0, 8.6 Hz, 1H)

$^{19}$F-NMR (standard: CFCl$_3$); δ (ppm) −75.17 (d, J=6.3 Hz)

IR (cm$^{-1}$) 3450, 1270, 1170, 1145, 1090, 940

Mass analysis m/e (M+ +H)
Calculated 243.1208
Found 243.1204

$[\alpha]_D^{26}$= −40.8° (C (concentration)=1.07, solvent: methanol)

(2) (2S,5S,6S) isomer

Molecular formula: $C_{12}H_{21}F_3O_3$ $^1$H-NMR; d (ppm) 0.94 (t, J=7.3 Hz, 3H) 1.32~1.47 (m, 2H) 1.53~1.66 (m, 2H) 1.77~2.03 (m, 5H) 3.43 (dt, J=9.7, 6.3 Hz, 1H) 3.69 (dt, J=9.7, 6.7 Hz, 1H) 3.82~3.93 (m, 2H) 4.86 (m, 1H)

$^{19}$F-NMR (standard: CFCl$_3$); d (ppm) −75.20 (d, J=6.2 Hz)

IR (cm$^{-1}$) 3400, 1270, 11V5, 1135, 1050, 945

Mass analysis m/e (M+ +H)
Calculated 243.1208
Found 243.1237

$[\alpha]_D^{25}$= +101.8° (C (concentration)=1.06, solvent: methanol)

Example 1

Synthesis of
(2R,5R,6R)-tetrahydro-6-trifluoromethyl-2-hexyloxy-5-(4″-hexyloxybiphenyl-4′-carbonyloxy)pyrane
(Compound 15)

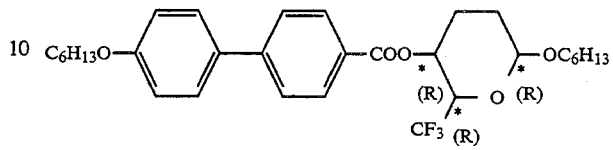

One ml of anhydrous pyridine was added to 5 ml of a toluene solution containing 0.32 g (1.0 mmol) of 4′-hexyloxy-4-biphenyl carboxylic acid chloride and 0.23 g (0.8 mmol) of (2R,5R,5R)-tetrahydro-6-trifluoromethyl-2-hexyloxy-5-hydroxypyrane obtained by the same manner as in Reference example 1, and the mixture was reacted at room temperature for 24 hours. To the reaction mixture was added distilled water to stop the reaction and the mixture was extracted with ether. Then, the extract was washed with a saturated saline solution and dried over anhydrous magnesium sulfate. After removing ether under reduced pressure, the residue was purified by silica gel column chromatography to obtain 0.25 g (0.5 mmol) of a desired compound (2R,5R,6R)-tetrahydro-6-trifluoromethyl-2-hexyloxy-5-(4″-hexyloxybiphenyl-4′-carbonyloxy)pyrane.

Physical properties of the resulting compound are shown below.

Molecular formula: $C_{31}H_{41}F_3O_5$ $^1$H-NMR; δ (ppm) 0.87~1.02 (m, 6H) 1.26~2.24 (m, 20H) 3.48 (dt, J=9.7, 6.5 Hz, 1H) 375 (dt, J=9.7, 6.8 Hz, 1H) 4.00 (t, J=6.5 Hz, 2H) 4.30 (dq, J=9.8, 6.3 Hz, 1H) 4.94 (m, 1H) 5.25 (ddd, J=5.3, 9.7, 9.8 Hz, 1H) 6.98 (d, J=8.7 Hz, 2H) 7.55 (d, J =8.7 Hz, 2H) 7.62 (d, J =8.4 Hz, 2H) 8.06 (d, J =8.3 Hz, 2H)

$^{19}$-NMR (standard: CFCl$_3$); δ (ppm) −75.98 (d, J=6.3 Hz)

IR (cm$^{-1}$) 1725, 1605, 1495, 1260, 1170, 1030

Mass analysis m/e (M+)
Calculated 550.2906
Found 550.2908

$[\alpha]_D^{27}$= −66.9° (C (concentration)=0.51, solvent: chloroform)

Example 2

Synthesis of
(2S,5R,6R)-tetrahydro-6-trifluoromethyl-2-hexyloxy-5-(4″-hexyloxybiphenyl-4′-carbonyloxy)pyrane
(Compound 16)

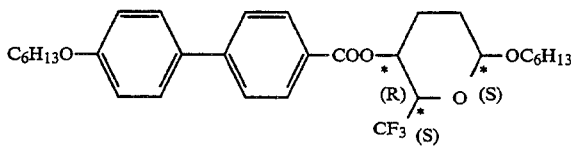

By using 0.49 g (1.6 mmol) of 4′-hexyloxy-4-biphenyl carboxylic acid chloride and 0.35 g (0.8 mmol) of (2S,5R,6R)-tetrahydro-6-trifluoromethyl-2-hexyloxy-5-hydroxypyrane obtained in Reference example 1, the same procedures as in Example 1 were carried out to obtain 0.44 g (0.8 mmol) of a desired compound (2S,5R,6R)-tetrahydro-6-trifluoromethyl-2-hexyloxy-5-(4″-hexyloxybiphenyl-4′-carboxyloxy)pyrane.

Physical properties of the resulting compound are shown below.

Molecular formula: $C_{31}H_{41}F_3O_5$ $^1$H-NMR; δ (ppm) 0.86~0.99 (m, 6H) 1.23~2.07 (m, 19H) 2.39~2.48 (m, 1H) 3.49 (dt, J=9.4, 6.8 Hz, 1H) 3.92 (dt, J=9.5, 6.7 Hz, 1H) 4.00 (t, J=6.6 Hz, 2H) 4.07 (dq, J=8.8, 6.3 Hz, 1H) 4.65 (dd, J=2.1, 8.2 Hz, 1H) 5.22 (ddd, J=5.0, 9.0, 9.5 Hz, 1H) 6.98 (d, J =8.8 Hz, 2H) 7.55 (d, J=8.7 Hz, 2H) 7.62 (d, J=8.5 Hz, 2H) 8.04 (d, J=8.4 Hz, 2H)

$^{19}$F-NMR (standard: $CFCl_3$); δ (ppm) −75.79 (d, J=6.3 Hz)

IR ($cm^{-1}$) 1720, 1610, 1500, 1260, 1190, 1060

Mass analysis m/e ($M^+$)
Calculated 550.2906
Found 550.2899

$[α]_D^{25}$=−13.0° (C (concentration)=1.10, solvent: chloroform)

Example 3

Synthesis of (2R,5R,6R)-tetrahydro-6-trifluoromethyl-2-hexyloxy-5-(4″-hexyloxybiphenyl-4′-methyleneoxy)pyrane

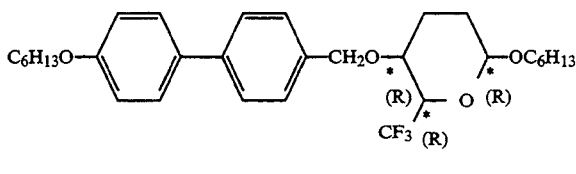

To a tetrahydrofuran solution (4 ml) containing 0.04 g (1.0 mmol) of 60% sodium hydride was added dropwise a tetrahydrofuran solution (3 ml) containing 0.23 g (0.8 mmol) of (2R,5R,6R)-tetrahydro-6-trifluoromethyl-2-hexyloxy-5-hydroxypyrane obtained by the same manner as in Reference example 1 under nitrogen atmosphere at 0° C., and the mixture was stirred for 30 minutes. Then, to the mixture was added dropwise a mixed solution of tetrahydrofuran (5 ml) and dimethylsulfoxide (5 ml) containing 0.31 g (1.0 mmol) of 4′-chloromethyl-4-hexyloxybiphenyl at room temperature and the mixture was reacted for 22 hours. To the reaction mixture was added distilled water to stop the reaction and the mixture was extracted with ether. Then, the extract was washed with brine and dried over anhydrous magnesium sulfate. After removing ether under reduced pressure, the residue was purified by silica gel column chromatography to obtain 0.44 g (0.8 mmol) of a desired compound (2R,5R,6R)-tetrahydro-6-trifluoromethyl-2-hexyloxy-5-(4″-hexyloxybiphenyl-4′-methyleneoxy)pyrane.

Physical properties of the resulting compound are shown below.

Molecular formula: $C_{31}H_{43}F_3O_4$ $^1$H-NMR; δ (ppm) 0.85~0.98 (m, 6H) 1.22~2.11 (m, 20H) 3.41 (dt, J=9.6, 6.4 Hz, 1H) 3.60~3.74 (m, 2H) 3.99 (t, J =6.6 Hz, 2H) 4.01~4.12 (m, 1H) 4.56 (d, J=11.3 Hz, 1H) 4.63 (d, J=11.3 Hz, 1H) 4.86 (m, 1H) 6.96 (d, J=8.7 Hz, 2H) 7.38 (d, J=8.1 Hz, 2H) 7.50 (d, J=8.6 Hz, 2H) 7.52 (d, J=8.1 Hz, 2H)

$^{19}$F-NMR (standard: $CFCl_3$); δ (ppm) −75.14 (d, J=6.6 Hz)

IR ($cm^{-1}$) 1610, 1500, 1245, 1175, 1060

Mass analysis m/e ($M^+$)
Calculated 536.3114
Found 536.3107

$[α]_D^{26}$=−63.0° (C (concentration)=0.78, solvent: chloroform)

Example 4

Synthesis of (2S,5R,6R)-tetrahydro-6-trifluoromethyl-2-hexyloxy-5-(4″-hexyloxybiphenyl-4′-methyleneoxy)pyrane

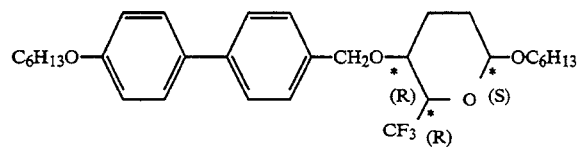

By using 0.39 g (1.5 mmol) of (2S,5R,6R)-tetrahydro-6-trifluoromethyl-2-hexyloxy-5-hydroxypyrane obtained by the same manner as in Reference example 1 and 0.53 g (1.8 mmol) of 4′-chloromethyl-4-hexyloxybiphenyl, the same procedures as in Example 3 were carried out to obtain 0.67 g (1.2 mmol) of a desired compound (2S,5R,6R)-tetrahydro-6-trifluoromethyl-2-hexyloxy-5-(4″-hexyloxybiphenyl-4′-methyleneoxy)pyrane.

Physical properties of the resulting compound are shown below.

Molecular formula: $C_{31}H_{43}F_3O_4$ $^1$H-NMR; δ (ppm) 0.83~1.00 (m, 6H) 1.25~1.69 (m, 16H) 1.75~1.88 (m, 2H) 1.89~1.99 (m, 1H) 2.22~2.33 (m, 1H) 3.45 (dt, J=9.5, 6.9 Hz, 1H) 3.60~3.69 (m, 1H) 3.75~3.92 (m, 2H) 3.99 (t, J=6.6 Hz, 2H) 4.53 (dd, J=2.3, 8.3 Hz, 1H) 4.56 (d, J=12.0 Hz, 1H) 4.61 (d, J=11.9 Hz, 1H) 6.96 (d, J=8.7 Hz, 2H) 7.36 (d, J=8.2 Hz, 2H) 7.50 (d, J=8.6 Hz, 2H) 7.53 (d, J=8.2 Hz, 2H)

$^{19}$F-NMR (standard: $CFCl_3$); δ (ppm) −74.95 (d, J=6.4 Hz)

IR ($cm^{-1}$) 1610, 1505, 1250, 1180, 1065

Mass analysis m/e ($M^+$)
Calculated 536.3114
Found 536.3099

$[α]_D^{27}$=+18.9° (C (concentration)=0.80, solvent: chloroform)

Example 5

Synthesis of (2S,5R,6R)-tetrahydro-2-butoxy-6-trifluoromethyl-5-(4″-hexyloxybiphenyl-4′-carbonyloxy) pyrane

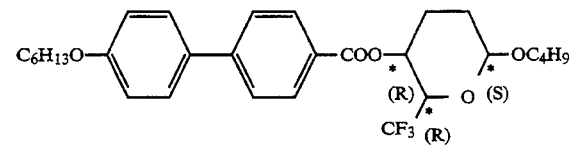

By using 0.46 g (1.5 mmol) of 4′-hexyloxy-4-biphenylcarboxylic acid chloride and 0.30 g (1.2 mmol) of (2S,5R,6R)-tetrahydro-2-butoxy-6-trifluoromethyl-5-hydroxypyrane obtained by the same manner as in Reference example 2, the same procedures as in Example 1 were carried out to obtain 0.2 g (0.3 mmol) of a desired compound (2S,5R,6R)-tetrahydro-2-butoxy-6-trifluoromethyl-5-(4″-hexyloxybiphenyl-4′-carbonyloxy) pyrane.

Physical properties of the resulting compound are shown below.

Molecular formula: $C_{29}H_{37}F_3O_5$ $^1$H-NMR; δ (ppm) 0.83~1.07 (m, 6H) 1.19~2.08 (m, 15H) 2.39~2.50 (m, 1H) 3.50 (dt, J=9.3, 6.3 Hz, 1H) 3.93 (dt, J=9.4, 6.7 Hz, 1H) 4.00 (t, J=6.6 Hz, 2H) 4.08 (dq, J=8.7, 6.4 Hz, 1H) 4.65 (dd, J=1.9, 8.1 Hz, 1H) 5.22 (ddd, J=5.1, 8.8, 9.2 Hz, 1H) 6.98 (d, J=8.6 Hz, 2H) 7.55 (d, J=8.6 Hz, 2H) 7.62 (d, J=8.3 Hz, 2H) 8.04 (d, J=8.3 Hz, 2H)

$^{19}$F-NMR (standard: CFCl$_3$); δ (ppm) −75.78 (d, J=6.2 Hz)

IR (cm$^{-1}$) 1720, 1605, 1500, 1180, 1055

Mass analysis m/e (M$^+$)
Calculated 522.2593
Found 522.2562

$[α]_D^{28}$=+16.9° (C (concentration)=0.76, solvent: chloroform)

Example 6

Synthesis of (2R,5R,6R)-tetrahydro-2-butoxy-6-trifluoromethyl-5-(4″-hexyloxybiphenyl-4′-methyleneoxy)pyrane

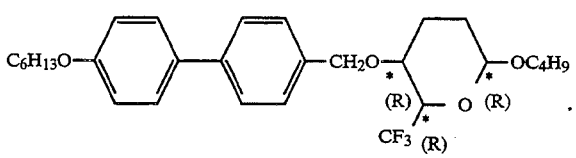

By using 0.29 g (0.29 mmol) of (2R,5R,6R)-tetrahydro-2-butoxy-6-trifluoromethyl-5-hydroxypyrane obtained by the same manner as in Reference example 2 and 0.43 g (1.4 mmol) of 4′-chloromethyl-4-hexyloxybiphenyl, the same procedures as in Example 3 were carried out to obtain 0.58 g (1.1 mmol) of a desired compound (2R,5R,6R)-tetrahydro-2-butoxy-6-trifluoromethyl-5-(4″-hexyloxybiphenyl-4′-methyleneoxy)propane.

Physical properties of the resulting compound are shown below.

Molecular formula: $C_{29}H_{39}F_3O_4$ $^1$H-NMR; δ (ppm) 0.85~0.99 (m, 6H) 1.26~1.70 (m, 12H) 1.75~1.87 (m, 2H) 1.89~1.98 (m, 1H) 2.22~2.34 (m, 1H) 3.46 (dt, J=9.5, 6.8 Hz, 1H) 3.60~3.69 (m, 1H) 3.76~3.92 (m, 2H) 3.99 (t, J=6.5 Hz, 2H) 4.53 (dd, J=2.3, 8.2 Hz, 1H) 4.55 (d, J=11.9 Hz, 1H) 4.60 (d, J=11.9 Hz, 1H) 6.96 (d, J=8.7 Hz, 2H) 7.36 (d, J=8.1 Hz, 2H) 7.50 (d, J=8.6 Hz, 2H) 7.52 (d, J=8.1 Hz, 2H)

$^{19}$F-NMR (standard: CFCl$_3$); δ (ppm) −74.97 (d, J=6.5 Hz)

IR (cm$^{-1}$) 1610, 1500, 1255, 1170, 1060

Mass analysis m/e (M$^+$)
Calculated 508.2801
Found 508.2792

$[α]_D^{28}$=−63.7° (C (concentration)=1.03, solvent: chloroform)

Example 7

Synthesis of (2R,5S,6S)-tetrahydro-6-trifluoromethyl-2-hexyloxy-5-(4″-heptylbiphenyl-4′-carbonyloxy)pyrane

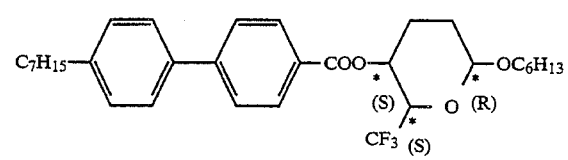

By using 0.38 g (1.2 mmol) of 4′-heptyl-4-biphenyl carboxylic acid chloride and 0.27 g (1.0 sol) of (2R,5S,6S)-tetrahydro-6-trifluoromethyl-2-hexyloxy-5-hydroxypyrane obtained Reference example 1, the same procedures as in Example 1 ere carried out to obtain 0.36 g (0.7 mmol) of a desired compound (2R,5S,6S)-tetrahydro-6-trifluoromethyl-2-hexyloxy-5-(4′-heptylbiphenyl-4′-carbonyloxy)pyrane.

Physical properties of the resulting compound are shown below.

Molecular formula: $C_{32}H_{43}F_3O_4$ $^1$H-NMR; δ (ppm) 0.83~0.98 (m, 6H) 1.22~2.08 (m, 21H) 2.39~2.50 (m, 1H) 2.66 (t, J=7.7 Hz, 1H) 3.50 (dt, J=9.4, 6.9 Hz, 1H) 3.92 (dt, J=9.4, 6.7 Hz, 1H) 4.08 (dq, J=8.8, 6.3 Hz, 1H) 4.65 (dd, J=2.0, 8.1 Hz, 1H) 5.23 (ddd, J=5.0, 9.0, 9.3 Hz, 1H) 7.28 (d, J=8.1 Hz, 2H) 7.54 (d, J=8.1 Hz, 2H) 7.65 (d, J=8.4 Hz, 2H) 8.06 (d, J=8.4 Hz, 2H)

$^{19}$F-NMR (standard: CFCl$_3$); δ (ppm) −75.76 (d, J=6.3 Hz)

IR (cm$^{-1}$) 1710, 1610, 1495, 1260, 1180, 1050

Mass analysis m/e (M$^+$)
Calculated 548.3114
Found 548.3086

$[α]_D^{27}$=−14.5° (C (concentration)=1.02, solvent: chloroform)

Example 8

Synthesis of (2S,5S,6S)-tetrahydro-6-trifluoromethyl-2-hexyloxy-5-(4-(5′-heptyl-2′-pyrimidinyl)phenyl-1-carbonyloxy)pyrane

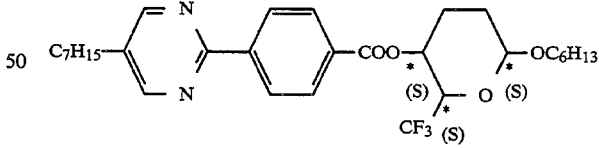

By using 0.38 g (1.2 mmol) of 4-(5′-heptyl-2′-pyrimidinyl)benzoic acid chloride and 0.27 g (1.0 mmol) of (2S,5S,6S)-tetrahydro-6-trifluoromethyl-2-hexyloxy-5-hydroxypyrane obtained in Reference example 1, the same procedures as in Example 1 were carried out to obtain 0.40 g (0.7 mmol) of a desired compound (2S,5S,6S)-tetrahydro-6-trifluoromethyl-2-hexyloxy-5-(4-(5′-heptyl-2′-pyrimidinyl) phenyl-1-carbonyloxy)pyrane.

Physical properties of the resulting compound are shown below.

Molecular formula: $C_{30}H_{41}F_3O_4N_2$ $^1$H-NMR; δ (ppm) 0.85~0.99 (m, 6H) 1.22~2.25 (m, 22H) 2.65 (t, J=7.6 Hz, 2H) 3.49 (dt, J=9.7, 6.5 Hz, 1H)

3.76 (dt, J=9.7, 6.8 Hz, 1H) 4.31 (dq, J=9.7, 6.3 Hz, 1H) 4.95 (m, 1H) 5.27 (ddd, J =5.2, 9.7, 9.9 Hz, 1H) 8.13 (d, J=8.7 Hz, 2H) 8.50 (d, J=8.6 Hz, 2H) 8.66 (s, 2H)

19F-NMR (standard: CFCl3); δ (ppm) −75.98 (d, J=6.3 Hz)

IR (cm−1) 1725, 1610, 1540, 1430, 1260, 1170, 1080

Mass analysis m/e (M+)
Calculated 550.3018
Found 550.3044

$[\alpha]_D^{26}$ = +70.4° (C (concentration)=1.02, solvent: chloroform)

Example 9

Synthesis of (2S,5S,6S)-tetrahydro-6-trifluoromethyl-2-hexyloxy-5-[trans-4-(4′-octyloxy-1′-phenyl)cyclohexane-1-carbonyloxy]pyrane

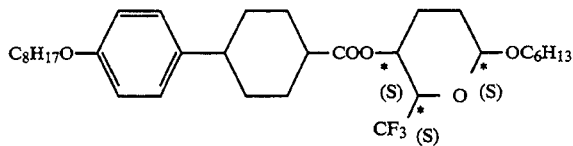

By using 0.42 g (1.2 mmol) of trans-4-(4′-octyloxy-1′-phenyl)cyclohexane-1-carboxylic acid chloride and 0.27 g (1.0 mmol) of (2S,5S,6S)-tetrahydro-6-trifluoromethyl-2-hexyloxy-5-hydroxypyrane obtained in Reference example 1, the same procedures as in Example 1 were carried out to obtain 0.40 g (0.7 mmol) of a desired compound (2S,5S,6S)-tetrahydro-6-trifluoromethyl-2-hexyloxy-5-[trans-4-(4′-octyloxy-1′-phenyl) cyclohexan-1-carbonyloxy]pyrane.

Physical properties of the resulting compound are shown below.

Molecular formula: C33H51F3O5

1H-NMR; δ (ppm) 0.81∼1.02 (m, 6H) 1.20∼2.16 (m, 32H) 2.24∼2.52 (m, 2H) 3.45 (dt, J=9.7, 6.5 Hz, 1H) 3.70 (dt, J=9.7, 6.7 Hz, 1H) 3.92 (t, J =6.5 Hz, 2H) 4.11 (dq, J=9.7, 6.3 Hz, 1H) 4.90 (m, 1H) 5.03 (ddd, J =5.3, 9.5, 9.7 Hz, 1H) 6.83 (d, J=8.7 Hz, 2H) 7.09 (d, J=8.7 Hz, 2H)

19F-NMR (standard: CFCl3); δ (ppm) −76.02 (d, J=6.3 Hz)

IR (infrared absorption: cm−1) 1740, 1610, 1515, 1245, 1170, 1040

Mass analysis m/e (M+)
Calculated 584.3689
Found 584.3702

$[\alpha]_D^{24}$ = +63.5° (C (concentration)=1.02, solvent: chloroform)

Example 10

Synthesis of (2R,5S,6S)-tetrahydro-6-trifluoromethyl-2-hexyloxy-5-(6-octyloxynaphthalene-2-carbonyloxy)pyrane

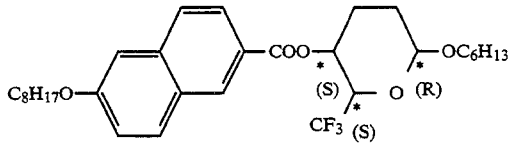

By using 0.38 g (1.2 mmol) of 6-octyloxynaphthalene-2-carboxylic acid chloride and 0.27 g (1.0 mmol) of (2R,5S,6S)-tetrahydro-6-trifluoromethyl-2-hexyloxy-5-hydroxypyrane obtained in Reference example 1, the same procedures as in Example 1 were carried out to obtain 0.19 g (0.3 mmol) of a desired compound (2R,5S,6S)-tetrahydro-6-trifluoromethyl-2-hexyloxy-5-(6-octyloxynaphthalene-2-carbonyloxy)pyrane.

Physical properties of the resulting compound are shown below.

Molecular formula: C31H43F3O5

1H-NMR; δ (ppm) 0.84∼0.98 (m, 6H) 1.21∼2.08 (m, 23H) 2.39∼2.52 (m, 1H) 3.50 (dt, J=9.4, 6.9 Hz, 1H) 3.92 (dt, J=9.4, 6.7 Hz, 1H) 4.09 (t, J=6.6 Hz, 2H) 4.06∼4.18 (m, 1H) 4.66 (dd, J=2.0, 7.9 Hz, 1H) 5.26 (ddd, J=5.0, 9.0, 9.3 Hz, 1H) 7.13∼7.22 (m, 2H) 7.73 (d, J=8.6 Hz, 1H) 7.83 (d, J=8.6 Hz, 1H) 7.97 (dd, J=1.4, 8.6 Hz, 1H) 8.47 (s, 1H)

19F-NMR (standard: CFCl3); δ (ppm) −75.76 (d, J=6.2 Hz)

IR (cm−1) 1720, 1625, 1275, 1195, 1060

Mass analysis m/e (M+)
Calculated 552.3063
Found 552.3065

$[\alpha]_D^{26}$ = −17.6° (C (concentration)=1.03, solvent: chloroform)

Example 11

Synthesis of (2S,5R,6R)-tetrahydro-2-butoxy-6-trifluoromethyl-5-[4-(4′-biphenyl-4-carbonyloxy)phenyl-1-carbonyloxy]pyrane

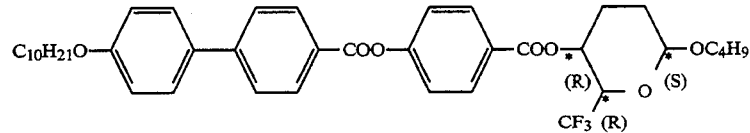

a) By using 0.59 g (2.4 mmol) of 4-benzyloxybenzoic acid chloride and 0.48 g (2.0 mmol) of (2S,5R,6R)-tetrahydro-2-butoxy-6-trifluoromethyl-5-hydroxypyrane obtained in Reference example 2, the same procedures as in Example 1 were carried out to obtain 0.41 g (0.9 mmol) of an ester compound.

b) To a mixed solution of toluene (5 ml) and acetic acid (1 ml) containing the compound obtained in the aforesaid a) was added 0.1 g of a 10% Pd/C, and under hydrogen atmosphere, hydrogenolysis was carried out at room temperature for 115 hours. Thereafter, the reaction mixture was filtered and the solvent was removed under reduced pressure, the residue was purified by silica gel column chromatography to obtain 0.30 g (0.8 mmol) of an alcohol compound.

c) By using 0.30 g (0.8 mmol) of the compound obtained in the aforesaid b) and 0.37 g (1.0 mmol) of 4'-decyloxy-4-biphenylcarboxylic acid chloride, the same procedures as in Example 1 were carried out to obtain 0.50 g (0.72 mmol) of a desired compound (2S,5R,6R)-tetrahydro-2-butoxy-6-trifluoromethyl-5-[4-(4'-decyloxybiphenyl-4-carbonyloxy)phenyl-1-carbonyloxy]pyrane.

Physical properties of the resulting compound are shown below.

Molecular formula: $C_{40}H_{49}F_3O_7$ $^1$H-NMR; δ (ppm) 0.85~1.02 (m, 6H) 1.22~2.09 (m, 23H) 2.40~2.52 (m, 1H) 3.51 (dt, J=9.4, 6.8 Hz, 1H) 3.93 (dt, J=9.4, 6.7 Hz, 1H) 4.02 (t, J=6.5 Hz, 2H) 4.00~4.12 (m, 1H) 4.65 (dd, J=2.0, 8.5 Hz, 1H) 5.18~5.30 (m, 1H) 7.01 (d, J=8.7 Hz, 2H) 7.33 (d, J=8.6 Hz, 2H) 60 (d, J =8.6 Hz, 2H) 70 (d, J=8.3 Hz, 2H) 8.10 (d, J=8.4 Hz, 2H) 8.23 (d, J=8.4 Hz, 2H)

$^{19}$F-NMR (standard: CFCl$_3$); δ (ppm) −75.79 (d, J=6.2 Hz)

IR (cm$^{-1}$) 1735, 1720, 1605, 1505, 1260, 1165, 1075

Mass analysis m/e (M$^+$)

Calculated 698.3431

Found 698.3442

$[α]_D^{26}$= +6.8° (C (concentration)=0.90, solvent: chloroform)

Example 12

Synthesis of (2S,5R,6R)-tetrahydro-6-trifluoromethyl-2-hexanoyloxy-5-(4"-heptylbiphenyl-4'-carbonyloxy)pyrane

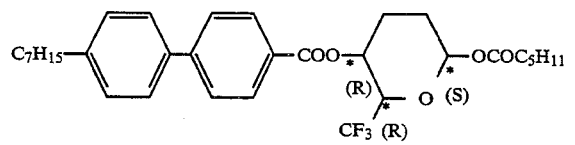

By using 0.47 g (1.5 mmol) of 4'-heptyl-4-biphenylcarboxylic acid chloride and 0.34 g (1.2 mmol) of (2S,5R,6R)-tetrahydro-6-trifluoromethyl-2-hexanoyloxy-5-hydroxypyrane, the same procedures as in Example 1 were carried out to obtain 0.33 g (0.6 mmol) of a desired compound (2S,5R,6R)-tetrahydro-6-trifluoromethyl-2-hexanoyloxy-5-(4"-heptylbiphenyl-4'-carbonyloxy)pyrane. Physical properties of the resulting compound are shown below.

Molecular formula: $C_{32}H_{41}F_3O_5$ $^1$H-NMR; δ (ppm) 0.80~1.03 (m, 6H) 1.19~1.46 (m, 12H) 1.54~1.79 (m, 4H) 1.86~2.17 (m, 3H) 2.24~2.47 (m, 3H) 2.66 (t, J=7.7 Hz, 2H) 4.36 (dq, J=9.8, 6.0 Hz, 1H) 5.25~5.36 (m, 1H) 6.30 (m, 1H) 7.28 (d, J=8.2 Hz, 2H) 7.54 (d, J=8.1 Hz, 2H) 7.66 (d, J=8.5 Hz, 2H) 8.08 (d, J=8.5 Hz, 2H)

$^{19}$F-NMR (standard: CFCl$_3$); δ (ppm) −75.98 (d, J=6.0 Hz)

IR (cm$^{-1}$) 1760, 1725, 1610, 1495, 1260, 1175, 1080

$[α]_D^{26}$= −49.2° (C (concentration)=1.11, solvent: chloroform)

Example 13

Synthesis of (2S,4S,5S,6S)-tetrahydro-6-trifluoromethyl-2-hexyloxy-4-methyl-5-(4"-hexyloxybiphenyl-4'-carbonyloxy)pyrane

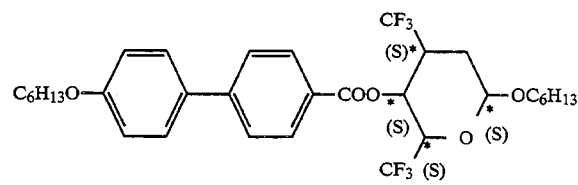

By using 0.25 g (0.8 mmol) of 4'-hexyloxy-4biphenylcarboxylic acid chloride and 0.15 g (0.5 mmol) of (2S,4S,5S,6S)-tetrahydro-6-trifluoromethyl-2-hexyloxy-4-methyl-5-hydroxypyrane, the same procedures as in Example 1 were carried out to obtain 0.18 g (0.3 mmol) of a desired combed (2S,4S,5S,6S)-tetrahydro-6-trifluoromethyl-2-hexyloxy-4-methyl-5-(4"-hexyloxybiphenyl-4'-carbonyloxy) pyrane.

Physical properties of the resulting compound are shown below.

Molecular formula: $C_{32}H_{43}F_3O_5$ $^1$H-NMR; δ (ppm) 0.79~1.03 (m, 6H) 1.11 (d, J=7.0 Hz, 3H) 1.16~2.42 (m, 19H) 3.45 (dt, J=9.7, 6.5 Hz, 1H) 3.89 (dt, J=9.7, 6.8 Hz, 1H) 4.01 (t, J=6.5 Hz, 2H) 4.30~4.44 (m, 1H) 4.96~5.02 (m, 1H) 5.48 (dd, J=4.9, 6.7 Hz, 1H) 6.99 (d, J=8.7 Hz, 2H) 7.56 (d, J=8.7 Hz, 2H) 7.63 (d, J=8.3 Hz, 2H) 8.09 (d, J=8.3 Hz, 2H)

$^{19}$F-NMR (standard: CFCl$_3$); δ (ppm) −75.61 (d, J=7.2 Hz)

IR (cm$^{-1}$) 1720, 1605, 1490, 1260, 1175

$[α]_D^{27}$= +62.9° (C (concentration)=0.94, solvent: chloroform)

Example 14

Synthesis of (2S,3R,5S,6S)-tetrahydro-6-trifluoromethyl-2-hexanoyloxy-3-methyl-5-(4"-hexyloxybiphenyl-4'-carbonyloxy) pyrane

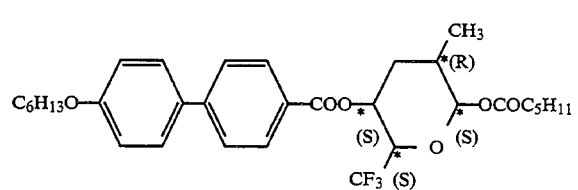

By using 0.43 g (1.4 mmol) of 4'-hexyloxy-4-biphenylcarboxylic acid chloride and 0.28 g (0.9 mmol) of (2S,3R,5S,6S)-tetrahydro-6-trifluoromethyl-2-hexanoyloxy-3-methyl- 5-hydroxypyrane, the same procedures as in Example 1 were carried out to obtain 0.38 g (0.7 mmol) of a desired compound (2S,3R,5S,6S)-tetrahydro-6-trifluoromethyl-2-hexanoyloxy-4-methyl-5-(4"-hexyloxybiphenyl-4'-carbonyloxy) pyrane.

Physical properties of the resulting compound are shown below.

Molecular formula: $C_{32}H_{41}F_3O_6$ $^1$H-NMR; δ (ppm) 0.86~0.97 (m, 6H) 0.96 (d, J=6.7 Hz, 3H) 1.23~1.88 (m, 18H) 1.99~2.16 (m, 1H) 2.41 (t, J=7.4 Hz, 2H) 2.45~2.57 (m, 1H) 4.01 (t, J=6.5 Hz, 2H) 4.19 (dq, J=9.6, 5.9 Hz, 1H) 5.21~5.32 (m, 1H)

5.51 (d, J=9.0 Hz, 1H) 6.99 (d, J=8.8 Hz, 2H) 7.56 (d, J=8.7 Hz, 2H) 7.62 (d, J=8.4 Hz, 2H) 8.03 (d, J=8.4 Hz, 2H)

19F-NMR (standard: CFCl₃); δ (ppm) −75.95 (d, J=5.9 Hz)

IR (cm⁻¹) 1760, 1720, 1605, 1500, 1250, 1160

$[\alpha]_D^{27} = -6.4°$ (C (concentration)=0.99, solvent: chloroform)

Example 15

An achiral host mixture A comprising compounds:

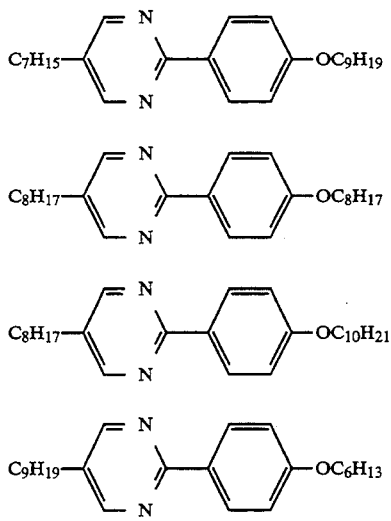

with each 25% by weight was prepared. To the achiral host mixture A was added the optically active tetrahydropyrane derivative obtained in Example 1 in an amount of 2% by weight to prepare a liquid crystal composition.

Phase transition temperatures of the resulting liquid crystal composition are as shown below.

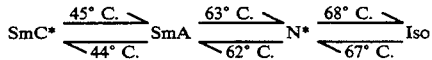

SmC*: Ferroelectric chiral smectic C phase
SmA: Smectic A phase
N*: Chiral nematic phase
ISO: Isotropic liquid state In the isotropic phase, this liquid crystal composition was injected in a liquid crystal device having a polyimide alignment layer to which a parallel rubbing treatment was carried out and having a cell distance of 1.5 μm. When it was oriented by gradually cooling and a rectangular wave voltage with Vpp=15 V was applied to it, a response time ($\tau_{0-90}$) of 103 μ sec was obtained at 30° C. The response time was defined by a time wherein a transmitted light intensity under crossed Nicols changed from 0 to 90%. Also, a spontaneous polarization value measured by a triangular wave method was 2.7 nC/cm².

Example 16

To the achiral host mixture A obtained in Example 15 was added the optically active tetrahydropyrane derivative obtained in Example 2 in an amount of 5% by weight to prepare a liquid crystal composition.

Phase transition temperatures of the resulting liquid crystal composition are as shown below.

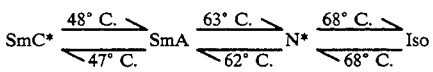

In the isotropic phase, this liquid crystal composition was injected in a liquid crystal device having a polyimide alignment layer to which a parallel rubbing treatment was carried out and having a cell distance of 1.4 μm. When it was oriented by gradually cooling and a rectangular wave voltage with Vpp=14 V was applied to it, a response time ($\tau_{0-90}$) of 62 μ sec was obtained at 30° C. The response time was defined by a time wherein a transmitted light intensity under crossed Nicols changed from 0 to 90%. Also, a spontaneous polarization value measured by a triangular wave method was 9.9 nC/cm2.

Reference Example 3

Synthesis of (5S,6S)-tetrahydro-5-t-butyldimethylsiloxy-6-trifluoromethyl-2-hydroxypyrane

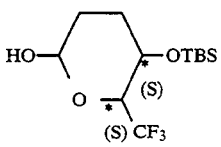

wherein TBS and * are the same as defined above.

(a) Under nitrogen atmosphere, 13.6 g (200 mmol) of furan was added to 150 ml of tetrahydrofuran, and 133 ml (200 mmol) of a 1.5 mol/liter n-butyl lithium-hexane solution was added dropwise at −20° C. to the mixture and the mixture was reacted for one hour. Then, 21.7 g (200 mmol) of trimethylsilyl chloride was added dropwise and the mixture was stirred at −20° C. for one hour. After reaction was carried out at −20° C. for one hour by adding 133 ml (200 mmol) of a 1.5 mol/liter n-butyl lithium-hexane solution, 28.4 g (200 mmol) of ethyl trifluoroacetate was added dropwise at −78° C., and the mixture was reacted at −78° C. for one hour and at room temperature for further one hour. To the reaction mixture was added 3N hydrochloric acid to stop the reaction and the mixture was extracted with ethyl acetate. Then, the extract was washed successively with a saturated sodium hydrogen carbonate solution and brine, and dried over anhydrous magnesium sulfate. Ethyl acetate was removed under reduced pressure to obtain a crude product of a furan derivative.

(b) To 100 ml of dried ethanol was added 2.3 g (60 mmol) of sodium borohydride, and the crude product of the furan derivative obtained by the above reaction was added dropwise at 0° C. over 30 minutes. After reaction was carried out at room temperature for 2 hours, ethanol was removed under reduced pressure, the reaction was stopped by adding 3N hydrochloric acid and the reaction mixture was extracted with ethyl acetate. Then, the extract was washed successively with a saturated sodium hydrogen carbonate solution and brine, and dried over anhydrous magnesium sulfate. After ethyl acetate was removed under reduced pressure, distillation was carried out under reduced pressure to obtain 40.5 g (170 mmol) of an alcohol compound.

(c) In 200 ml of methylene chloride were added 64.2 g (269 mmol) of the alcohol compound obtained by the reaction as mentioned above (b) and 27.7 ml (350 mmol) of pyridine, and then 27.5 g (350 mmol) of acetyl chloride was added dropwise to the mixture at 0° C. and reacted at room temperature for 2 hours.

Then, the reaction was stopped by adding 3N hydrochloric acid and the reaction mixture was extracted with methylene chloride. Then, the extract was washed successively with a saturated sodium hydrogen carbonate solution and distilled water, and dried over anhydrous magnesium sulfate. After methylene chloride was removed under reduced pressure, distillation was carried out under reduced pressure to obtain 75.1 g (268 mmol) of an ester compound.

(d) To 1800 ml of distilled water was added 58.5 g (209 mmol) of the ester compound obtained in the aforesaid reaction, and the mixture was stirred in a mini-jar fermentor at 40° C. To the mixture was added 30 g of Lipase PS and the mixture was reacted for 10 hours. The reaction was stopped by adding 3N hydrochloric acid, and the reaction mixture was cooled to 0° C. and filtered by using Celite. The filtrate was extracted with ethyl acetate, the extract was washed with brine, dried over anhydrous magnesium sulfate and ethyl acetate was removed under reduced pressure. Then, the residue was separated and purified by silica gel column chromatography to obtain 23.2 g (97.4 mmol) of an optically active alcohol compound and 25.6 g (91.4 mmol) of an optically active ester compound. Incidentally, the resulting alcohol compound had an optical purity of 98.0% e.e. (e) In 200 ml of methylene chloride was dissolved 25.8 g (108 mmol) of the optically active alcohol compound obtained in the aforesaid reaction, and 10.5 g (151 mmol) of imidazole and 23.0 g (151 mmol) of t-butyldimethylsilyl chloride were added to the solution at 0° C. and the mixture was stirred for 15 minutes and reacted at room temperature for 16 hours. The reaction was stopped by adding distilled water and the reaction mixture was extracted with methylene chloride. Then, the extract was washed with distilled water and dried over anhydrous magnesium sulfate. After removing methylene chloride under reduced pressure, the residue was separated and purified by column chromatography to obtain 37.2 g (106 mmol) of a silyl ether compound.

(f) Under nitrogen atmosphere, to 120 ml of acetic acid were added 14.1 g (40 mmol) of the silyl ether compound obtained in the aforesaid reaction and 23.2 g (60 mmol) of magnesium monoperoxyphthalate, and the mixture was reacted at 80° C. for 12 hours. After removing acetic acid under reduced pressure, a saturated sodium hydrogen carbonate solution was added to the residue and the mixture was extracted with ethyl acetate. After removing ethyl acetate under reduced pressure, the residue was separated and purified by column chromatography to obtain 4.7 g (16 mmol) of a (4S,1'S)butenoride compound and 3.0 g (10 mmol) of a (4R,1'S)butenoride compound. Incidentally, 4.2 g (12 mmol) of the starting material was also recovered.

(g) In 40 ml of ethanol were dissolved 13.7 g (46 mmol) of the (4S,1'S) and (4R,1'S)butenoride compounds without separation, and 1.4 g of a 10% Pd/C (containing 10% by weight of Pd) was added to the solution and under hydrogen atmosphere, the mixture was reacted at room temperature for 15 hours. After the reaction mixture was filtered and the solvent was removed under reduced pressure, the residue was separated and purified by silica gel column chromatography to obtain 8.2 g (29 mmol) of a (4S,1'S)butanoride compound and 3.6 g (12 mmol) of a (4R,1'S) butanoride compound.

(h) Under nitrogen atmosphere, to 40 ml of diethyl ether was added 7.5 g (25 mmol) of (4S,1'S)butanoride compound obtained in the aforesaid reaction, and then 32 ml (30 mmol) of a 0.93 mol/liter diisobutyl aluminum hydride dissolved in n-hexane solution was added dropwise to the mixture at −78° C. and reacted For 3 hours. The reaction was stopped by adding distilled water, and the reaction mixture was neutralized by adding 1N hydrochloric acid and extracted with diethyl ether. The extract was washed with brine and then dried over anhydrous magnesium sulfate, and diethyl ether was removed under reduced pressure. Then, the residue was purified by silica gel column chromatography to obtain 7.3 g (24 mmol) of a lactol compound.

(i) Under nitrogen atmosphere, to 50 ml of tetrahydrofuran was added 7.3 g (24 mmol) of the lactol compound obtained in the aforesaid reaction, and 10 ml of tetrahydrofuran solution containing 3.0 g (27 mmol) of potassium t-butoxide was added dropwise to the mixture at −78 ° C. and reacted for 3 hours. The reaction was stopped by adding distilled water, and the reaction mixture was neutralized by adding 1N hydrochloric acid and extracted with diethyl ether. The extract was washed with brine and then dried over anhydrous magnesium sulfate, and diethyl ether was removed under reduced pressure. Then, the residue was purified by silica gel column chromatography to obtain 6.4 g (21 mmol) of a desired (5S,6S)-tetrahydro-5-t-butyldimethylsiloxy-6-trifluoromethyl-2-hydroxypyrane. The resulting compound was a mixture of diastereomers with a molar ratio of 82:18 by a nuclear magnetic resonance method of an isotope fluorine.

Physical properties of the resulting compounds are shown below.

(1) (2R,5S,6S) isomer

Molecular formula: $C_{12}H_{23}F_3O_3Si$ $^1$H-NMR (proton nuclear magnetic resonance method); δ (ppm) 0.03 (s, 6H) 0.85 (s, 9H) 1.40∼2.10 (m, 4H) 2.90∼3.10 (m, 1H) 3.78 (dt, J=5.6, 8.9 Hz, 1H) 4.11 (dq, J =9.2, 6.9 Hz, 1H) 5.20∼5.40 (m, 1H)

$^{19}$F-NMR (nuclear magnetic resonance method using isotope fluorine, standard: $CF_3COOH$); δ (ppm) 4.90 (d, J=6.1 Hz)

(2) (2S,5S,6S) isomer

Molecular formula: $C_{12}H_{23}F_3O_3Si$ $^1$H-NMR; d (ppm) 0.05 (s, 6H) 0.85 (s, 9H) 1.40∼2.10 (m, 4H) 3.20∼3.40 (m, 1H) 3.67 (dq, J=8.8, 6.2 Hz, 1H) 3.70∼3.90 (m, 1H) 4.80∼5.00 (m, 1H)

$^{19}$F-NMR (standard: $CF_3COOH$); δ (ppm) 4.80 (d, J=7.6 Hz)

Example 17

Synthesis of (2S,5R,6R)-tetrahydro-6-trifluoromethyl-5-hexanoyloxy-2-(4″-hexyloxybiphenyl-4′-carbonyloxy)pyrane (Compound 51)

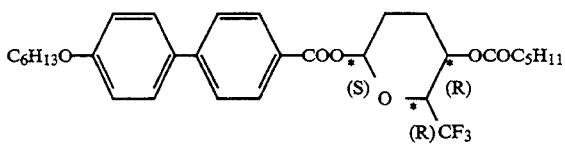

(a) Two ml of anhydrous pyridine was added to 5 ml of a toluene solution containing 1.14 g (3.6 mmol) of 4′-hexyloxy-4-biphenyl carboxylic acid chloride and 0.90 g (3.0 mmol) of (5R,6R)-tetrahydro-5-t-butyl-dimethylsiloxy-6-trifluoromethyl-2-hydroxypyrane obtained by the same manner as in Reference example 3, and the mixture was reacted at room temperature for 20 hours. To the reaction mixture was added distilled water to stop the reaction and the mixture was extracted with ether. Then, the extract was washed with brine and dried over anhydrous magnesium sulfate. After removing ether under reduced pressure, the residue was purified by silica gel column chromatography to obtain 1.12 g (1.9 mmol) of an ester compound.

(b) In 10 ml of tetrahydrofuran was dissolved 1.12 g of the ester compound obtained in the aforesaid (a), and 1.0 ml of a tetrahydrofuran solution containing 1.0 mol/liter of tetra-n-butyl ammonium fluoride and the mixture was reacted at 0° C. for one hour and at room temperature for 6 hours. To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 0.08 g (0.2 mmol) of an alcohol compound having asymmetric carbons (2R,5R,6R) and 0.74 g (1.6 mmol) of an alcohol compound having asymmetric carbons (2S,5R,6R).

(c) In 3 ml of toluene was dissolved 0.08 g of the alcohol compound having the asymmetric carbons (2R,5R,6R) obtained in the aforesaid (b), and 0.5 ml of pyridine and 0.03 ml (0.2 mmol) of hexanoyl chloride were successively added and the mixture was reacted at room temperature for 20 hours. To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 0.09 g (0.2 mmol) of a desired compound (2S,5R,6R)-tetrahydro-6-trifluoromethyl-5-hexanoyloxy-2-(4″-hexyloxybiphenyl-4′-carbonyloxy)pyrane. Physical properties of the resulting compound are shown below.

Molecular formula: $C_{31}H_{39}F_3O_6$ $^1$H-NMR; δ (ppm) 0.82~1.01 (m, 6H) 1.20~2.31 (m, 18H) 2.33 (t, J=7.5 Hz, 2H) 4.02 (t, J=6.6 Hz, 2H) 4.29 (dq, J=9.8, 5.9 Hz, 1H) 5.10~5.22 (m, 1H) 6.48 (m, 1H) 7.00 (d, J=8.8 Hz, 2H) 7.59 (d, J=8.8 Hz, 2H) 7.67 (d, J=8.4 Hz, 2H) 8.11 (d, J=8.5 Hz, 2H)

$^{19}$F-NMR (standard: $CFCl_3$); δ (ppm) −76.05 (d, J=5.9 Hz)

IR (cm$^{-1}$) 1740, 1730, 1605, 1500, 1265, 1170, 1070

Mass analysis m/e (M+)
Calculated 564.2699
Found 564.2704

$[α]_D^{27}$=−51.6° (C (concentration)=0.92, solvent: chloroform)

Example 18

Synthesis of (2S,5R,6R)-tetrahydro-6-trifluoromethyl-5-hexanoyloxy-2-(4″-heptylbiphenyl-4′-carbonyloxy)pyrane (Compound 54)

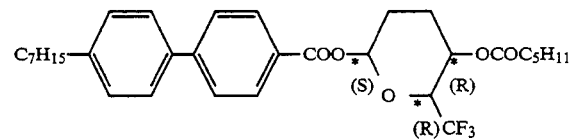

The same procedures were carried out as in Example 17 except for using 0.74 g (2.4 mmol) of 4′-heptyl-4-biphenylcarboxylic acid chloride, 0.15 g (0.3 mmol) of a desired compound (2S,5R,6R)-tetrahydro-6-trifluoromethyl-5-hexanoyloxy-2-(4″-heptylbiphenyl-4′-carbonyloxy) pyrane was obtained.

Physical properties of the resulting compound are shown below.

Molecular formula: $C_{32}H_{41}F_3O_5$ $^1$H-NMR; δ (ppm) 0.82~0.97 (m, 6H) 1.18~1.45 (m, 11H) 1.53~1.76 (m, 5H) 1.94~2.29 (m, 4H) 2.33 (t, J=7.6 Hz, 2H) 2.67 (t, J=7.7 Hz, 2H) 4.29 (dq, J=9.8, 5.9 Hz, 1H) 5.10~5.23 (m, 1H) 6.49 (m, 1H) 7.30 (d, J=8.1 Hz, 2H) 7.56 (d, J=8.2 Hz, 2H) 7.70 (d, J=8.5 Hz, 2H) 8.13 (d, J=8.5 Hz, 2H)

$^{19}$F-NMR (standard: $CFCl_3$); δ (ppm) −76.07 (d, J=5.9 Hz)

IR (cm$^{-1}$) 1735, 1610, 1490, 1265, 1170, 1070

Mass analysis m/e (M+)
Calculated 562.2906
Found 562.2934

$[α]_D^{25}$=−50.3° (C (concentration)=0.68, solvent: chloroform)

Example 19

Synthesis of (2R,5R,6R)-tetrahydro-6-trifluoromethyl-5-hexanoyloxy-2-(4″-hexyloxybiphenyl-4′-carbonyloxy)pyrane

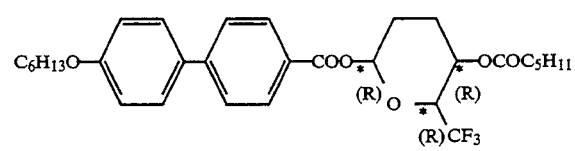

The same procedures were carried out as in Example 17 (c) except for using 0.37 g (0.8 mmol) of the alcohol compound having the asymmetric carbons (2S,5R,6R) obtained by the procedure in Example 17 (b) and 0.13 ml (1.0 mmol) of hexanoyl chloride to obtain 0.41 g (0.7 mmol) of a desired compound (2R,5R,6R)-tetrahydro- 6-trifluoromethyl-5-hexanoyloxy-2-(4″-hexyloxybiphenyl-4′-carbonyloxy)pyrane was obtained.

Physical properties of the resulting compound are shown below.

Molecular formula: $C_{31}H_{39}F_3O_6$ $^1$H-NMR; δ (ppm) 0.82~1.00 (m, 6H) 1.21~2.48 (m, 18H) 2.34 (t, J=7.5 Hz, 2H) 4.01 (t, J=6.5 Hz, 2H) 4.14 (dq, J=6.8, 6.8 Hz, 1H) 5.09~5.20 (m, 1H) 6.18 (dd, J=2.7, 7.0 Hz, 1H) 6.99 (d, J=8.8 Hz, 2H) 7.56 (d, J=8.8 Hz, 2H) 7.63 (d, J=8.5 Hz, 2H) 8.11 (d, J=8.4 Hz, 2H)

$^{19}$F-NMR (standard: $CFCl_3$); δ (ppm) −75.39 (d, J=6.8 Hz)

IR ($cm^{-1}$) 1740, 1605, 1500, 1270, 1180, 1080

Mass analysis m/e ($M^+$)
Calculated 564.2699
Found 564.2681

$[α]_D^{25}$ = −15.3° (C (concentration)=1.20, solvent: chloroform)

Example 20

Synthesis of (2R,5R,6R)-tetrahydro-6-trifluoromethyl-5-hexanoyloxy-2-(4″-heptylbiphenyl-4′-methyleneoxy)pyrane

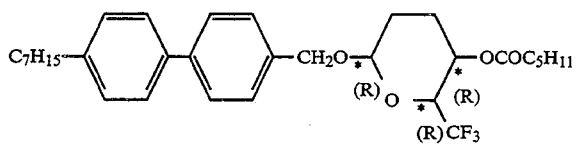

(a) To 8 ml of a tetrahydrofuran solution containing 0.85 g (3.0 mmol) of 4′-heptyl-4-hydroxymethylbiphenyl and 0.60 g (2.0 mmol) of (5R,6R)-tetrahydro-5-t-butyldimethylsiloxy-6-trifluoromethyl-2-hydroxypyrane obtained by the same manner as in Reference example 3 was added 0.1 g of paratoluene sulfonic acid as an acid catalyst, and the mixture was refluxed at room temperature for 50 hours. To the reaction mixture was added distilled water to stop the reaction and the mixture was extracted with ether. Then, the resulting extract was washed with brine and dried over anhydrous magnesium sulfate. After removing ether in the dried material under reduced pressure, the residue was purified by silica gel column chromatography to obtain 0.69 g (1.2 mmol) of an acetal compound.

(b) In 10 ml of tetrahydrofuran was dissolved 0.69 g of the acetal compound obtained in the aforesaid (a), and 1.2 ml of a tetrahydrofuran solution containing 1.0 mol/liter of tetra-n-butyl ammonium fluoride and the mixture was reacted at 0° C. for one hour and at room temperature for 14 hours. To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 0.39 g (0.9 mmol) of an alcohol compound having asymmetric carbons (2R,5R,6R) and 0.13 g (0.3 mmol) of an alcohol compound having asymmetric carbons (2S,5R,6R).

(c) In 5 ml of toluene was dissolved 0.39 g of the alcohol compound having the asymmetric carbons (2R,5R,6R) obtained in the aforesaid (b), and 1.0 ml of pyridine and 0.14 ml (1.0 mmol) of hexanoyl chloride were successively added and the mixture was reacted at room temperature for 20 hours. To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 0.43 g (0.8 mmol) of a desired compound (2R,5R,6R)-tetrahydro-6-trifluoromethyl-5-hexanoyloxy2-(4″-heptylbiphenyl-4′-methyleneoxy)pyrane.

Physical properties of the resulting compound are shown below.

Molecular formula: $C_{32}H_{43}F_3O_4$ $^1$H-NMR; δ (ppm) 0.82~0.96 (m, 6H) 1.20~1.42 (m, 11H) 1.51~1.73 (m, 5H) 1.84~2.07 (m, 4H) 2.29 (t, J=7.5 Hz, 2H) 2.65 (t, J=7.7 Hz, 2H) 4.19 (dq, J=9.7, 6.2 Hz, 1H) 4.57 (d, J=11.9 Hz, 1H) 4.78 (d, J=11.9 Hz, 1H) 5.01~5.13 (m, 2H) 7.26 (d, J=8.1 Hz, 2H) 7.41 (d, J=8.2 Hz, 2H) 7.51 (d, J=8.2 Hz, 2H) 7.59 (d, J=8.2 Hz, 2H)

$^{19}$F-NMR (standard: $CFCl_3$); δ (ppm) −76.09 (d, J=6.3 Hz)

IR ($cm^{-1}$) 1740, 1610, 1500, 1270, 1170, 1090

Mass analysis m/e ($M^+$)
Calculated 548.3114
Found 548.3130

$[α]_D^{25}$ = −71.1° (C (concentration)=1.00, solvent: chloroform)

Example 21

Synthesis of (2S,5R,6R)-tetrahydro-6-trifluoromethyl-5-hexanoyloxy-2-(4″-heptylbiphenyl-4′-methyleneoxy)pyrane

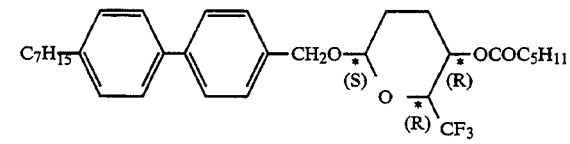

The same procedures were carried out as in Example 20 (c) except for using 0.13 g (0.3 mol) of the alcohol compound having the asymmetric carbons (2S,5R,6R) obtained by the procedure in Example 20 (b) to obtain 0.13 g (0.2 mmol) of a desired compound (2S,5R,6R)-tetrahydro-6-trifluoromethyl-5-hexanoyloxy-2-(4″-heptylbiphenyl-4′-methyleneoxy)pyrane.

Physical properties of the resulting compound are shown below.

Molecular formula: $C_{32}H_{43}F_3O_4$ $^1$H-NMR; δ (ppm) 0.80~0.98 (m, 6H) 1.14~1.43 (m, 13H) 1.49~2.02 (m, 6H) 2.18~2.32 (m, 1H) 2.29 (t, J=7.5 Hz, 2H) 2.64 (t, J=7.7 Hz, 2H) 3.89 (dq, J=8.8, 6.3 Hz, 1H) 4.64 (d, J=12.0 Hz, 1H) 4.65 (dd, J=2.4, 8.1 Hz, 1H) 4.92 (d, J=11.9 Hz, 1H) 4.97~5.11 (m, 1H) 7.25 (d, J=8.1 Hz, 2H) 7.40 (d, J=8.2 Hz, 2H) 7.50 (d, J=8.1 Hz, 2H) 7.57 (d, J=8.2 Hz, 2H)

$^{19}$F-NMR (standard: $CFCl_3$); δ (ppm) −75.83 (d, J=6.3 Hz)

IR ($cm^{-1}$) 1730, 1600, 1500, 1270, 1165, 1060

Mass analysis m/e ($M^+$)
Calculated 548.3114

Example 22

Synthesis of (2S,5S,6S)-tetrahydro-6-trifluoromethyl-5-hexyloxy-2-(4″-hexyloxybiphenyl-4′-methyleneoxy)pyrane

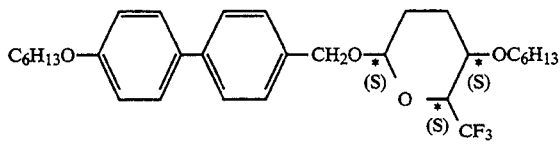

(a) By using 0.85 g (3.0 mmol) of 4′-hexyloxy-4-hydroxymethylbiphenyl and 0.60 g (2.0 mmol) of (5S,6S)-tetrahydro-5-t-butyldimethylsiloxy-6-trifluoromethyl-2-hydroxypyrane obtained in Reference example 3, the same procedures as in Example 20 (a) and (b) were carried out to obtain 0.37 g (0.8 mmol) of an alcohol compound having asymmetric carbons (2S,5S,6S) and 0.12 g (0.3 mmol) of an alcohol compound having asymmetric carbons (2R,5S,6S).

(b) A tetrahydrofuran (4 ml) solution containing 0.37 g of the alcohol compound having the asymmetric carbons (2S,5S,6S) obtained in the aforesaid (a) was added dropwise to a tetrahydrofuran (4 ml) solution containing 0.04 g (1.0 mmol) of 60% sodium hydride under nitrogen atmosphere at 0° C., and the mixture was stirred for 30 minutes. Then, 0.15 ml (1.1 mmol) of 1-bromohexane and 3 ml of dimethylsulfoxide were added at room temperature and the mixture was reacted for 14 hours.

To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 0.27 g (0.5 mmol) of a desired compound (2S,5S,6S)-tetrahydro-6-trifluoromethyl-5-hexyloxy-2-(4″-hexyloxybiphenyl-4′-methyleneoxy)pyrane.

Physical properties of the resulting compound are shown below.

Molecular formula: $C_{31}H_{43}F_3O_4$ $^1$H-NMR; δ (ppm) 0.79~0.98 (m, 6H) 1.18~2.09 (m, 20H) 3.35~3.64 (m, 3H) 4.00 (t, J=6.6 Hz, 2H) 3.98~4.12 (m, 1H) 4.52 (d, J=11.8 Hz, 1H) 4.75 (d, J=11.8 Hz, 1H) 4.97 (m, 1H) 6.96 (d, J=8.8 Hz, 2H) 7.38 (d, J=8.2 Hz, 2H) 7.51 (d, J=8.8 Hz, 2H) 7.53 (d, J=8.2 Hz, 2H)

$^1$F-NMR (standard: $CFCl_3$); δ (ppm) −75.32 (d, J=6.7 Hz)

IR $(cm^{-1})$ 1610, 1500, 1245, 1170, 1080

Mass analysis m/e (M+)
Calculated 536.3114
Found 536.3125

$[α]_D^{25} = +76.7°$ (C (concentration)=1.22, solvent: chloroform)

Example 23

Synthesis of (2R,5R,6R)-tetrahydro-5-acetoxy-6-trifluoromethyl-2-(4″-hexyloxybiphenyl-4′-carbonyloxy)pyrane

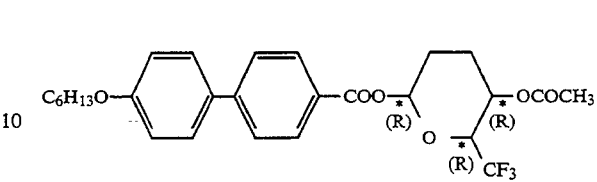

The same procedures were carried out as in Example (c) except for using 0.37 g (0.8 mmol) of the alcohol compound having the asymmetric carbons (2S,5R,6R) obtained by the procedure in Example ]7 (b) and 0.07 ml (1.0 mmol) of acetyl chloride to obtain 0.39 g (0.8 mmol) of a desired compound (2R,5R,6R)-tetrahydro-5-acetoxy-6-trifluoromethyl-2-(4″-hexyloxybiphenyl-4′-carbonyloxy)pyrane.

Physical properties of the resulting compound are shown below.

Molecular formula: $C_{27}H_{31}F_3O_6$ $^1$H-NMR; δ (ppm) 0.91 (t, J=6.9 Hz, 3H) 1.22~1.56 (m, 6H) 1.70~2.13 (m, 8H) 2.33~2.26 (m, 1H) 4.00 (t, J=6.6 Hz, 2H) 4.14 (dq, J=6.8, 6.8 Hz, 1H) 5.09~5.19 (m, 1H) 6.18 (dd, J=2.7, 7.0 Hz, 1H) 6.98 (d, J=8.8 Hz, 2H) 7.56 (d, J=8.7 Hz, 2H) 7.63 (d, J=8.5 Hz, 2H) 8.10 (d, J=8.4 Hz, 2H)

$^{19}$F-NMR (standard: $CFCl_3$); δ (ppm) −75.50 (d, J=6.8 Hz)

IR $(cm^{-1})$ 1740, 1610, 1500, 1240, 1175, 1080

Mass analysis m/e (M+)
Calculated 508.2073
Found 508.2077

$[α]_D^{23} = -14.9°$ (C (concentration)=1.03, solvent: chloroform)

Example 24

Synthesis of (2S,5S,6S)-tetrahydro-6-trifluoromethyl-5-hexyloxy-2-(4″-hexyloxybiphenyl-4′-carbonyloxy)pyrane

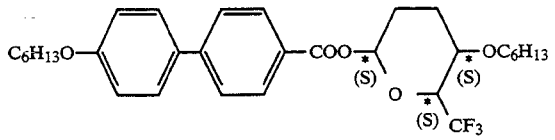

(a) In 40 ml of hexanol was dissolved 6.4 g (21 mmol) of (5S,6S)-tetrahydro-5-t-butyldimethylsiloxy-6-trifluoromethyl-2-hydroxypyrane, and 0.1 g of paratoluene sulfonic acid was added to the solution and the mixture was reacted at room temperature for 18 hours. The reaction mixture without by treatment was purified by silica gel column chromatography to obtain 8.0 g (21 mmol) of an acetal combed.

(b) In 20 ml of tetrahydrofuran was dissolved 8.0 g of the acetal compound obtained in the aforesaid (a), and 10 ml of a tetrahydrofuran solution containing 1.0 mol/liter of tetra-n-butyl ammonium fluoride and the mixture was reacted at 0° C. for one hour and at room temperature for 40 hours. To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 3.0 g (11 mmol) of an alcohol compound having asymmetric carbons (2R,5S,6S) and 2.3 g (8.0 mmol) of an alcohol compound having asymmetric carbons (2S,5S,6S).

(c) A tetrahydrofuran (5 ml) solution containing 0.56 g (2.1 mmol) of the alcohol compound having the asymmetric carbons (2S,5S,6S) obtained in the aforesaid (b) was added dropwise to a tetrahydrofuran (3 ml) solution containing 0.10 g (2.5 mmol) of 60% sodium hydride under nitrogen atmosphere at 0° C., and the mixture was stirred for 30 minutes. Then, 0.35 ml (2.5 mmol) of 1-bromohexane and 2 ml of dimethylsulfoxide were added at room temperature and the mixture was reacted for 18 hours. To the reaction mixture was added distilled water to stop the reaction, and the reaction mixture was extracted with ether. Then, the extract was washed with brine and dried over anhydrous magnesium sulfate. After removing ether under reduced pressure, the residue was separated and purified by silica gel column chromatography to obtain 0.72 g (2.0 mmol) of an ether compound.

(d) In 10 ml of tetrahydrofuran was dissolved 0.52 g (1.5 mmol) of the ether compound obtained in the aforesaid (c), and 10 ml of distilled water and 2 ml of conc. sulfuric acid were added and the mixture was refluxed for 50 hours. A 1N potassium hydroxide aqueous solution was added distilled water to the mixture to stop the reaction, and the reaction mixture was extracted with ether. Then, the extract was washed with a saturated saline solution and dried over anhydrous magnesium sulfate. After removing ether under reduced pressure, the residue was separated and purified by silica gel column chromatography to obtain 0.37 g (1.4 mmol) of a hemiacetal compound.

(e) By using 0.29 g (1.1 mmol) of the hemiacetal compound obtained in the aforesaid (d) and 0.49 g (1.6 mmol) of 4′-hexyloxy-4-biphenylcarboxylic acid chloride, the same procedures as in Example 1 (a) were carried out to obtain 0.34 g (0.6 mmol) of a desired compound (2S,5S,6S)-tetrahydro-6-trifluoromethyl-5-hexyloxy-2-(4″-hexyloxybiphenyl-4′-carbonyloxy)pyrane.

Physical properties of the resulting compound are shown below.

Molecular formula: $C_{31}H_{41}F_3O_5$ $^1$H-NMR; δ (ppm) 0.81~0.99 (m, 6H) 1.19~1.68 (m, 15H) 1.70~1.93 (m, 4H) 2.12~2.25 (m, 1H) 2.29~2.42 (m, 1H) 3.40~3.65 (m, 3H) 4.01 (t, J=6.6 Hz, 2H) 6.14 (dd, J=2.7, 6.6 Hz, 1H) 6.98 (d, J=8.8 Hz, 2H) 7.56 (d, J=8.8 Hz, 2H) 7.62 (d, J=8.5 Hz, 2H) 8.10 (d, J=8.4 Hz, 2H)

$^{19}$F-NMR (standard: $CFCl_3$); δ (ppm) −74.98 (d, J=7.4 Hz)

IR (cm$^{-1}$) 1730, 1605, 1495, 1265, 1180, 1080
Mass analysis m/e (M+)
Calculated 550.2906
Found 550.2914

$[\alpha]_D^{26} = +10.7°$ (C (concentration)=1.03, solvent: chloroform)

Example 25

To the achiral host mixture A obtained in Example 15 was added the optically active tetrahydropyrane derivative obtained in Example 18 in an amount of 2% by weight to prepare a liquid crystal composition.

Phase transition temperatures of the liquid crystal composition are as shown below.

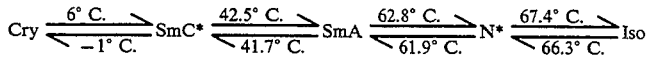

Cry: Crystalline phase
SmC*: Ferroelectric chiral smectic C phase
SmA: Smectic A phase
N*: Cholesteric phase
Iso: Isotropic state In the isotropic phase, this liquid crystal composition was injected in a liquid crystal device having a polyimide alignment layer to which a parallel rubbing treatment was carried out and having a cell distance of 1.6 μm. When it was oriented by gradually cooling and a rectangular wave voltage with Vpp=16 V was applied to it, a response time ($\tau_{0-90}$) of 57 μsec was obtained at 30° C. The response time was defined by a time wherein a transmitted light intensity under crossed Nicols changed from 0 to 90%. Also, a spontaneous polarization value measured by a triangular wave method was 5.0 nC/cm$^2$.

Example 26

To the achiral host mixture A obtained in Example 15 was added the optically active tetrahydropyrane derivative obtained in Example 17 in an amount of 2% by weight to prepare a liquid crystal composition.

Phase transition temperatures of the resulting liquid crystal composition are as shown below.

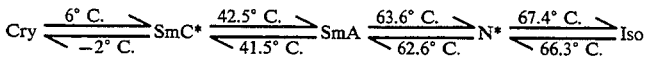

In the isotropic phase, this liquid crystal composition was injected in a liquid crystal device having a polyimide alignment layer to which a parallel rubbing treatment was carried out and having a cell distance of 1.6 μm. When it was oriented by gradually cooling and a rectangular wave voltage with Vpp=16 V was applied to it, a response speed ($\tau_{0-90}$) of 71 μsec was obtained at 30° C. Also, a spontaneous polarization value measured by a triangular wave method was 4.9 nC/cm$^2$.

Example 27

In the same manner as in the above Examples, compounds 1 to 59 (1 to 44: specific examples of the formula (I), 45 to 59: specific examples of the formula (I′)) shown in Table 2a and Table 2b were synthesized.

The obtained compounds were added to the achiral host mixture A prepared in Example 15 in an amount of 2% by weight to prepare liquid crystal compositions. In the isotropic phase, these liquid crystal compositions were each injected in a liquid crystal device having a polyimide alignment layer to which a parallel rubbing treatment was carried out and having a cell distance of about 2 μm.

After the liquid crystal device was oriented by gradually cooling, a response time ($\tau_{0-90}$) was measured by applying a rectangular wave voltage with Vpp=20 V at 30° C. The results obtained are also shown in Table 2a and Table 2b.

TABLE 2a

| Compound No. | $R^1$ | $R^2$ | $R^3$ | $R^4$ | Rf | $X^1$ | $X^2$ | $X^3$ | $X^4$ | A | B | n | Optically active position (2,5,6) | Response time (μsec) | Corresponding Example No. |
|---|---|---|---|---|---|---|---|---|---|---|---|---|---|---|---|
| 1 | $C_6H_{13}$ | H | H | $C_6H_{13}$ | $CF_3$ | O | — | COO | O | — | phenyl | 0 | (R,R,R) | 159 | — |
| 2 | $C_6H_{13}$ | H | H | $C_6H_{13}$ | $CF_3$ | O | — | COO | O | — | phenyl | 0 | (R,S,S) | 229 | — |
| 3 | $C_{10}H_{21}$ | H | H | $C_6H_{13}$ | $CF_3$ | O | — | COO | O | — | phenyl | 0 | (R,R,R) | 135 | — |
| 4 | $C_{10}H_{21}$ | H | H | $C_6H_{13}$ | $CF_3$ | O | — | COO | O | — | phenyl | 0 | (R,S,S) | 256 | — |
| 5 | $C_4H_9$ | H | H | $C_4H_9$ | $CF_3$ | O | — | COO | O | — | biphenyl | 0 | (R,R,R) | 132 | — |
| 6 | $C_4H_9$ | H | H | $C_4H_9$ | $CF_3$ | O | — | COO | O | — | biphenyl | 0 | (S,R,R) | 140 | — |
| 7 | $C_{10}H_{21}$ | H | H | $C_4H_9$ | $CF_3$ | O | — | COO | O | — | biphenyl | 0 | (R,R,R) | 179 | — |
| 8 | $C_{10}H_{21}$ | H | H | $C_4H_9$ | $CF_3$ | O | — | COO | O | — | biphenyl | 0 | (S,R,R) | 147 | — |

TABLE 2a-continued

| Compound No. | R$^1$ | R$^2$ | R$^3$ | R$^4$ | Rf | X$^1$ | X$^2$ | X$^3$ | X$^4$ | A | B | n | Optically active position (2,5,6) | Response time (μsec) | Corresponding Example No. |
|---|---|---|---|---|---|---|---|---|---|---|---|---|---|---|---|
| 9  | C$_6$H$_{13}$ | H | H | C$_3$H$_7$    | CF$_3$ | O | — | COO | O | — | 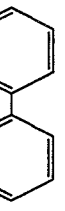 | 0 | (S,S,S) | 124 | — |
| 10 | C$_6$H$_{13}$ | H | H | C$_3$H$_7$    | CF$_3$ | O | — | COO | O | — | 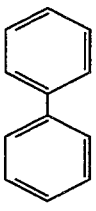 | 0 | (R,S,S) | 139 | — |
| 11 | C$_6$H$_{13}$ | H | H | C$_4$H$_9$    | CF$_3$ | O | — | COO | O | — | 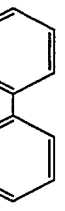 | 0 | (R,R,R) | 146 | — |
| 12 | C$_6$H$_{13}$ | H | H | C$_4$H$_9$    | CF$_3$ | O | — | COO | O | — |  | 0 | (S,R,R) | 157 | 5 |
| 13 | C$_6$H$_{13}$ | H | H | C$_5$H$_{11}$ | CF$_3$ | O | — | COO | O | — | 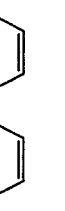 | 0 | (S,S,S) | 112 | — |
| 14 | C$_6$H$_{13}$ | H | H | C$_5$H$_{11}$ | CF$_3$ | O | — | COO | O | — |  | 0 | (S,R,R) | 120 | — |
| 17 | C$_6$H$_{13}$ | H | H | C$_{10}$H$_{21}$ | CF$_3$ | O | — | COO | O | — | 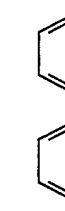 | 0 | (S,S,S) | 149 | — |
| 18 | C$_6$H$_{13}$ | H | H | C$_{10}$H$_{21}$ | CF$_3$ | O | — | COO | O | — | 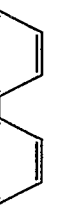 | 0 | (R,S,S) | 180 | — |

TABLE 2a-continued
| Compound No. | R¹ | R² | R³ | R⁴ | Rf | X¹ | X² | X³ | X⁴ | A | B | n | Optically active position (2,5,6) | Response time (μsec) | Corresponding Example No. |
|---|---|---|---|---|---|---|---|---|---|---|---|---|---|---|---|
| 19 | C₆H₁₃ | H | H | C(CH₃)₃ | CF₃ | O | — | COO | O | — | 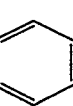 | 0 | (S,S,S) | 148 | — |
| 20 | C₆H₁₃ | H | H | C(CH₃)₃ | CF₃ | O | — | COO | O | — |  | 0 | (R,S,S) | 132 | — |
| 21 | C₇H₁₅ | H | H | C₆H₁₃ | CF₃ | — | — | COO | O | — | 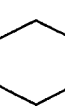 | 0 | (S,S,S) | 150 | — |
| 22 | C₇H₁₅ | H | H | C₆H₁₃ | CF₃ | — | — | COO | O | — | 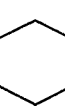 | 0 | (R,S,S) | 134 | 7 |
| 23 | C₇H₁₅ | H | H | C₆H₁₃ | CF₃ | — | — | COO | O | — | 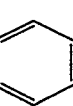 | 0 | (S,S,S) | 166 | 8 |
| 24 | C₇H₁₅ | H | H | C₆H₁₃ | CF₃ | — | — | COO | O | — | 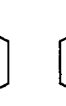 | 0 | (R,S,S) | 220 | — |
| 25 | C₈H₁₇ | H | H | C₆H₁₃ | CF₃ | O | — | COO | O | — | 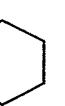 | 0 | (S,S,S) | 176 | 9 |
| 26 | C₈H₁₇ | H | H | C₆H₁₃ | CF₃ | O | — | COO | O | — | 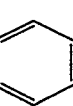 | 0 | (R,S,S) | 234 | — |

TABLE 2a-continued
| Compound No. | R¹ | R² | R³ | R⁴ | Rf | X¹ | X² | X³ | X⁴ | A | B | n | Optically active position (2,5,6) | Response time (μsec) | Corresponding Example No. |
|---|---|---|---|---|---|---|---|---|---|---|---|---|---|---|---|
| 27 | $C_8H_{17}$ | H | H | $C_6H_{13}$ | $CF_3$ | O | — | COO | O | — | 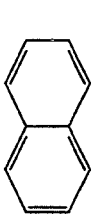 | 0 | (S,S,S) | 179 | — |
| 28 | $C_8H_{17}$ | H | H | $C_6H_{13}$ | $CF_3$ | O | — | COO | O | — | 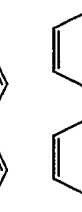 | 0 | (R,S,S) | 194 | 10 |
| 29 | $C_8H_{17}$ | H | H | $C_6H_{13}$ | $CF_3$ | O | — | COO | O | — | 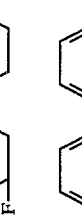 | 0 | (S,R,R) | 139 | — |
| 30 | $C_6H_{13}$ | H | H | $C_4H_9$ | $CF_3$ | O | — | $CH_2O$ | O | — | 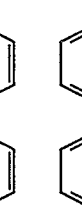 | 0 | (R,R,R) | 292 | 6 |
| 31 | $C_6H_{13}$ | H | H | $C_4H_9$ | $CF_3$ | O | — | $CH_2O$ | O | — | 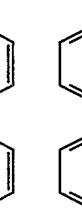 | 0 | (S,R,R) | 467 | — |
| 32 | $C_6H_{13}$ | H | H | $C_6H_{13}$ | $CF_3$ | O | — | $CH_2O$ | O | — | 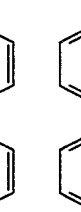 | 0 | (R,R,R) | 252 | 3 |
| 33 | $C_6H_{13}$ | H | H | $C_6H_{13}$ | $CF_3$ | O | — | $CH_2O$ | O | — | 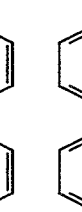 | 0 | (S,R,R) | 562 | 4 |
| 34 | $C_6H_{13}$ | H | H | $C_5H_{11}$ | $CF_3$ | O | — | COO | OCO | — |  | 0 | (S,R,R) | 142 | — |

TABLE 2a-continued

| Compound No. | R¹ | R² | R³ | R⁴ | Rf | X¹ | X² | X³ | X⁴ | A | B | n | Optically active position (2,5,6) | Response time (μsec) | Corresponding Example No. |
|---|---|---|---|---|---|---|---|---|---|---|---|---|---|---|---|
| 35 | C₇H₁₅ | H | H | C₅H₁₁ | CF₃ | — | — | COO | OCO | — | 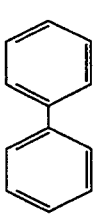 | 0 | (S,R,R) | 109 | 12 |
| 36 | C₆H₁₃ | CH₃ | H | C₆H₁₃ | CF₃ | O | — | COO | O | — | 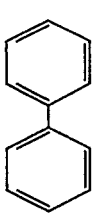 | 0 | (S,S,S,S) | 176 | 13 |
| 37 | C₆H₁₃ | CH₃ | H | C₆H₁₃ | CF₃ | O | — | COO | O | — | 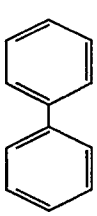 | 0 | (R,S,S,S) | 396 | — |
| 38 | C₆H₁₃ | H | CH₃ | C₆H₁₃ | CF₃ | — | — | COO | O | — | 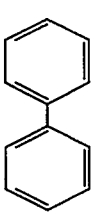 | 0 | (S,R,S,S) | 167 | — |
| 39 | C₆H₁₃ | H | CH₃ | C₅H₁₁ | CF₃ | O | — | COO | O | — | 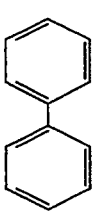 | 0 | (S,R,S,S) | 259 | 14 |
| 40 | C₆H₁₃ | H | H | C₅H₁₁ | CF₃ | O | — | COO | OCO | — | 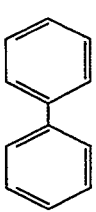 | 0 | (S,R,S,S) | 885 | — |
| 41 | C₇H₁₅ | H | H | C₅H₁₁ | CF₃ | — | — | COO | OCO | — | 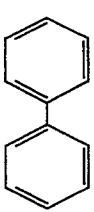 | 0 | (R,S,R) | 381 | — |
| 42 | C₇H₁₅ | H | H | C₅H₁₁ | CF₃ | — | — | COO | OCO | — | 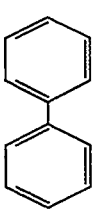 | 0 | (S,S,R) | 105 | — |

TABLE 2a-continued
| Compound No. | R¹ | R² | R³ | R⁴ | Rf | X¹ | X² | X³ | X⁴ | A | B | n | Optically active position (2,5,6) | Response time (μsec) | Corresponding Example No. |
|---|---|---|---|---|---|---|---|---|---|---|---|---|---|---|---|
| 43 | $C_{10}H_{21}$ | H | H | $C_4H_9$ | $CF_3$ | O | — | COO | O | 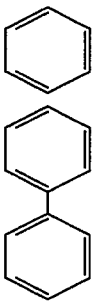 |  | 1 | (R,R,R) | 426 | — |
| 44 | $C_{10}H_{21}$ | H | H | $C_4H_9$ | $CF_3$ | O | COO | COO | O | 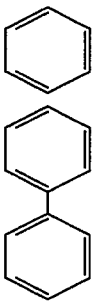 |  | 1 | (S,R,R,) | 372 | 11 |

TABLE 2b

| Compound No. | $R^1$ | $R^2$ | $R^3$ | $R^4$ | Rf | $X^1$ | $X^2$ | $X^3$ | $X^4$ | A | B | n | Optically active position (2,5,6) | Response time (μsec) | Corresponding Example No. |
|---|---|---|---|---|---|---|---|---|---|---|---|---|---|---|---|
| 45 | $C_6H_{13}$ | H | H | $C_6H_{13}$ | $CF_3$ | O | — | COO | O | — | 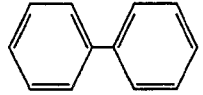 | 0 | (S,R,R) | 66 | — |
| 46 | $C_6H_{13}$ | H | H | $C_6H_{13}$ | $CF_3$ | O | — | COO | O | — | 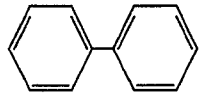 | 0 | (S,S,S) | 102 | 24 |
| 47 | $C_7H_{15}$ | H | H | $C_6H_{13}$ | $CF_3$ | — | — | COO | O | — | 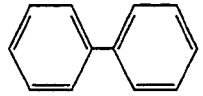 | 0 | (R,S,S) | 64 | — |
| 48 | $C_7H_{15}$ | H | H | $C_6H_{13}$ | $CF_3$ | — | — | COO | O | — | 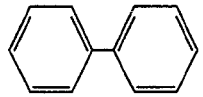 | 0 | (S,S,S) | 128 | — |
| 49 | $C_6H_{13}$ | H | H | $C_6H_{13}$ | $CF_3$ | O | — | $CH_2O$ | O | — | 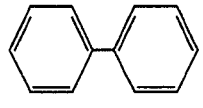 | 0 | (S,S,S) | 578 | 22 |
| 50 | $C_6H_{13}$ | H | H | $C_6H_{13}$ | $CF_3$ | O | — | $CH_2O$ | O | — | 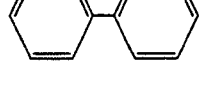 | 0 | (R,S,S) | 295 | — |
| 52 | $C_6H_{13}$ | H | H | $C_5H_{11}$ | $CF_3$ | O | — | COO | OCO | — | 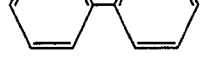 | 0 | (R,R,R) | 232 | 19 |
| 53 | $C_6H_{13}$ | H | H | $CH_3$ | $CF_3$ | O | — | COO | OCO | — | 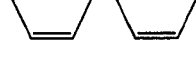 | 0 | (R,R,R) | 262 | 23 |
| 55 | $C_7H_{15}$ | H | H | $C_5H_{11}$ | $CF_3$ | — | — | COO | OCO | — | 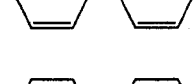 | 0 | (R,R,R) | 233 | — |
| 56 | $C_6H_{13}$ | H | H | $C_5H_{11}$ | $CF_3$ | O | — | $CH_2O$ | OCO | — |  | 0 | (R,R,R) | 344 | — |
| 57 | $C_6H_{13}$ | H | H | $C_5H_{11}$ | $CF_3$ | O | — | $CH_2O$ | OCO | — |  | 0 | (S,R,R) | 342 | — |
| 58 | $C_7H_{15}$ | H | H | $C_5H_{11}$ | $CF_3$ | — | — | $CH_2O$ | OCO | — |  | 0 | (R,R,R) | 473 | 20 |

TABLE 2b-continued

| Compound No. | R¹ | R² | R³ | R⁴ | Rf | X¹ | X² | X³ | X⁴ | A | B | n | Optically active position (2,5,6) | Response time (μsec) | Corresponding Example No. |
|---|---|---|---|---|---|---|---|---|---|---|---|---|---|---|---|
| 59 | C₇H₁₅ | H | H | C₅H₁₁ | CF₃ | — | — | CH₂O | OCO | — |  | 0 | (S,R,R) | 329 | 21 |

Example 28

To the achiral host mixture A obtained in Example 15 was added each compound (J5, 16, 21, 22, 34, 46, 51 and 54) shown in Table 3 in an amount of 2% by weight to prepare liquid crystal compositions A to H. All these compositions showed phase sequence of Iso phase→N* phase→SmA phase→SmC* phase. Resulting compositions were each sealed in a wedge cell and helical pitches were measured at a temperature 1° C. higher than the lower limit of the N* phase. The results are shown in Table 3 with spontaneous polarization of the composition. The helical pitch was determined by measuring a distance (W) of line defect by using a polarizing microscope and calculated from the theoretical equation (P=2 W Tan θ) when an oblique angle of the wedge cell is θ.

As to a sense of helix, it has been confirmed that the helical sense of the compound (XXXVIII):

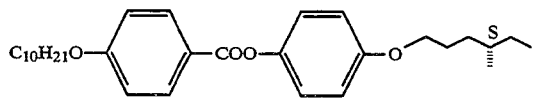

induced in the N* phase is L(−). Accordingly, helical sense of the compositions A to H were obtained by a contact method using the above as the standard compound and shown in Table 3.

TABLE 3

| Composition | Compound No. | Polarity of spontaneous polarization (nC/cm²) | Helical sense and pitch of N* (μm) | Corresponding Example No. |
|---|---|---|---|---|
| A | 15 | −3.7 | −14 | 1 |
| B | 16 | −3.7 | +8 | 2 |
| C | 21 | +3.3 | +20 | — |
| D | 22 | +4.6 | −7 | 7 |
| E | 46 | +5.9 | +18 | 24 |
| F | 51 | +5.4 | +22 | 17 |
| G | 54 | +5.4 | +27 | 18 |
| H | 34 | −3.7 | +10 | — |

Example 29

To the achiral host mixture A obtained in Example 15 were added the compound 15 obtained in Example 1 as shown in Table 3 in an amount of 1.3% by weight and the compound 16 obtained in Example 2 in an amount of 0.7% by weight to prepare a liquid composition. Phase transition temperatures of the resulting liquid crystal composition are as shown below.

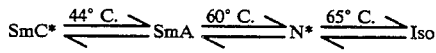

In the isotropic phase, this liquid crystal composition was injected in a liquid crystal device having a polyimide alignment layer to which a parallel rubbing treatment was carried out and having a cell distance of 1.8 μm. It was oriented by gradually cooling and when a rectangular wave voltage with Vpp=18 V was applied to it, a response time (τ₀₋₉₀) of 114 μsec was obtained at 30° C. and a spontaneous polarization value was 3.8 nC/cm².

Also, helical pitch of the N* phase was 100 μm or more and alignment quality was extremely good.

Example 30

To archiral host mixture A obtained in Example 15 were added the compound 22 and the compound 46 each having the same polarity of the spontaneous polarization but different helical sense of the N* phase as shown in Table 3 in amounts of 0.5% by weight and 1.5% by weight, respectively, to prepare a liquid crystal composition. Phase transition temperatures of the resulting liquid crystal composition are as shown below.

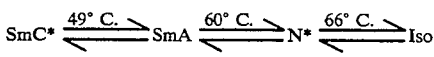

In the isotropic phase, this liquid crystal composition was injected in into a liquid crystal device having a polyimide alignment layer to which a parallel rubbing treatment was carried out and having a cell distance of 1.7 μm. It was oriented by gradually cooling and when a rectangular wave voltage with Vpp=17 V was applied to it, a response time (τ₀₋₉₀) of 113 μsec was obtained at 30° C. and a spontaneous polarization value was 3.6 nC/cm².

Also, helical pitch in the N* phase was 100μm or more and alignment quality was extremely good.

Example 31

To the achiral host mixture A obtained in Example 15 were added 1% by weight of the compound 15 obtained in Example 1 and 1% by weight of the compound 34 each having the same polarity of the spontaneous polarization but different helical sense of the N* phase as shown in Table 3, to prepare a liquid crystal composition. Phase transition temperatures of the resulting liquid crystal composition are as shown below.

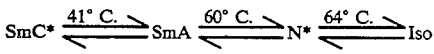

In the isotropic phase, this liquid crystal composition was injected in a liquid crystal device having a polyimide alignment layer to which a parallel rubbing treatment was carried out and having a cell distance of 2.6 μm. The resulting liquid crystal device was oriented by gradually cooling and when a rectangular wave voltage with Vpp=26 V was applied to it, a response time ($\tau_{0-90}$) of 111 μsec was obtained at 30° C. and a spontaneous polarization value was 4.7 nC/cm².

Also, helical pitch in the N* phase was 100 μm or more and alignment quality was extremely good.

Industrial Applicability

As mentioned above, the optically active tetrahydropyrane derivative of the present invention is a novel compound which is chemically stable, has no color and excellent in light stability, and has a high speed response.

Accordingly, the optically active tetrahydropyrane derivative of the present invention can be effectively utilized for a display device and an electro-optic device.

We claim:

1. An optically active tetrahydropyrane derivative represented by the formula (I):

$$R^1-X^1-(A-X^2)_n-B-X^3-\overset{R^2\quad R^3}{\underset{Rf}{\diagup\!\!\!\diagdown}}-X^4-R^4$$

or $$R^1-X^1-(A-X^2)_n-B-X^3-\overset{R^2\quad R^3}{\underset{O-Rf}{\diagup\!\!\!\diagdown}}-X^4-R^4$$

wherein,
Rf is —CF$_3$;
R$^1$ is a straight chain alkyl group having from 4–10 carbon atoms;
R$^2$ is a hydrogen atom or a methyl group;
R$^3$ is a hydrogen atom or a methyl group;
R$^4$ is a straight or branched chain alkyl group having from 1 to 10 carbon atoms;
X$^1$ is —O—, or a single bond;
X$^2$ is —COO—, or a single bond;
X$^3$ is —COO— or —CHO$_2$—;
X$^4$ is —O— or —OCO—;
n is 0 or 1;
A is

[structure: biphenyl]

B is

[structures: phenyl-naphthyl, and others]

-continued

[structures: biphenyl; phenyl-cyclohexyl; pyrimidine-phenyl; fluoro-biphenyl]

2. A liquid crystal composition which comprises
   (a) at least one kind of the compound represented by the formula (I) or (I') as claimed in claim 1,
   (b) a compound having a chiral smectic C phase (SmC* phase) other than (a) or a mixture thereof and/or
   (c) a compound having a smectic C phase (SmC phase) other than (a) or a mixture thereof.

3. A liquid crystal composition which comprises
   (a) at least two kinds of the optically active tetrahydropyrane derivatives having the same polarity of spontaneous polarization and different helical sense of a cholesteric phase (N* phase) according to claim 1,
   (b) a compound having a chiral smectic C phase (SmC* phase) other than (a) or a mixture thereof and/or
   (c) a compound having a smectic C phase (SmC phase) other than (a) or a mixture thereof.

4. A liquid crystal composition which comprises at least two kinds of optically active tetrahydropyrane derivatives according to claim 1.

5. A liquid crystal device which comprises the optically active tetrahydropyrane derivative according to claim 1 interposed between a pair of electrode substrates.

6. A liquid crystal device which comprises the liquid crystal composition according to any one of claims 2, 3 or 4 interposed between a pair of electrode substrates.

7. An optically active tetrahydropyrane derivative as claimed in claim 1 wherein R$^1$ is a straight chain alkyl group having 6–7 carbon atoms, R$^2$ is a hydrogen atom, R$^{39}$ is a hydrogen atom, R$^4$ is a straight chain alkyl group having from 5–6 carbon atoms, X$^2$ is a single bond, X$^3$ is —COO—, X$^4$ is —O— or —OCO—, n is 0 and B is:

[structure: biphenyl]

* * * * *